United States Patent
Remaley et al.

(10) Patent No.: US 11,136,372 B2
(45) Date of Patent: Oct. 5, 2021

(54) APOC-II MIMETIC PEPTIDES

(71) Applicants: The United States of America, as Represented by the Secretary, Dept. of Health & Human Services, Rockville, MD (US); Novo Nordisk A/S, Bagsvaerd (DK)

(72) Inventors: Alan Thomas Remaley, Bethesda, MD (US); Soumitra Shanker Ghosh, San Diego, CA (US); Madhav N. Devalaraja, Acton, MA (US); Chih-Hung Lo, Rockville, MD (US); Denis O. Sviridov, Rockville, MD (US); Anna Wolska, Washington, DC (US)

(73) Assignees: The United States of America, as represented by the Secretary, Dept. of Health & Human Services, Rockville, MD (US); Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/479,183

(22) PCT Filed: Jan. 19, 2018

(86) PCT No.: PCT/US2018/014532
§ 371 (c)(1),
(2) Date: Jul. 18, 2019

(87) PCT Pub. No.: WO2018/136803
PCT Pub. Date: Jul. 26, 2018

(65) Prior Publication Data
US 2020/0140522 A1 May 7, 2020

Related U.S. Application Data

(60) Provisional application No. 62/448,358, filed on Jan. 19, 2017, provisional application No. 62/476,535, filed on Mar. 24, 2017, provisional application No. 62/476,531, filed on Mar. 24, 2017.

(51) Int. Cl.
| | | |
|---|---|---|
| *A61K 38/17* | (2006.01) | |
| *C07K 14/775* | (2006.01) | |
| *A61K 9/00* | (2006.01) | |
| *A61K 38/00* | (2006.01) | |

(52) U.S. Cl.
CPC ........ *C07K 14/775* (2013.01); *A61K 38/1709* (2013.01); *A61K 38/1722* (2013.01); *A61K 9/0019* (2013.01); *A61K 38/00* (2013.01); *C07K 2317/53* (2013.01); *C07K 2319/21* (2013.01); *C07K 2319/41* (2013.01); *C07K 2319/42* (2013.01)

(58) Field of Classification Search
CPC .............. C07K 14/775; A61K 38/1709; A61K 38/1722
See application file for complete search history.

(56) References Cited

U.S. PATENT DOCUMENTS

| | | | | |
|---|---|---|---|---|
| 6,156,727 A * | 12/2000 | Garber | ................. | C07K 14/775 514/1.9 |
| 8,119,590 B2 | 2/2012 | Bisgaier et al. | | |
| 2004/0018591 A1* | 1/2004 | Butt | ....................... | C12N 15/62 435/69.1 |
| 2005/0202532 A1* | 9/2005 | Bielicki | ............... | C07K 14/775 435/69.1 |
| 2010/0016173 A1 | 1/2010 | Nagalla et al. | | |
| 2011/0033518 A1 | 2/2011 | Remaley et al. | | |
| 2020/0140522 A1 | 5/2020 | Remaley et al. | | |

FOREIGN PATENT DOCUMENTS

| | | |
|---|---|---|
| AU | 2018210404 A1 | 8/2019 |
| CA | 3050106 A1 | 7/2018 |
| CN | 110831957 A | 2/2020 |
| EA | 201991491 A1 | 12/2019 |
| EP | 3571216 A1 | 11/2019 |
| IN | 201917032726 A | 9/2019 |
| KR | 20190121305 A | 10/2019 |
| SG | 11201906422 A | 8/2019 |
| TW | 201835097 A | 10/2018 |

OTHER PUBLICATIONS

Amar et al. A Novel Apolipoprotein C-II Mimetic Peptide That Activates Lipoprotein Lipase and Decreases Serum Triglycerides in Apolipoprotein E-Knockout Mice. The Journal of Pharmacology and Experimental Therapeutics. Feb. 2015, vol. 352, pp. 227-235. (Year: 2015).*
Bagio et al. Apolipoprotein C-II Deficiency Syndrome. The Journal of Clinical Investigation. 1986, vol. 77, No. 2, pp. 520-527. (Year: 1986).*
Kinnunen et al. Activation of lipoprotein lipase by native and synthetic fragments of human plasma apolipoprotein C-II. Proceedings of the National Academy of Sciences USA. Nov. 1977, vol. 74, No. 11, pp. 4848-4851. (Year: 1977).*
PCT International Search Report and Written Opinion, PCT Application No. PCT/US18/14532, dated Jun. 14, 2018, 19 pages.
Abe, C. et al., "Triton WR1339, an inhibitor of lipoprotein lipase, decreases vitamin E concentration in some tissues of rats by inhibiting its transport to liver," The Journal of Nutrition, 2007, vol. 137, No. 2, pp. 345-350.
Amar, M. J. A. et al. "A Novel Apolipoprotein C-II Mimetic Peptide That Activates Lipoprotein Lipase and Decreases Serum Triglycerides in Apolipoprotein E-Knockout Mice." Journal of Pharmacology and Experimental Therapeutics, vol. 352, Iss. 2, Feb. 2015, pp. 227-235.
Anantharamaiah, G. M. et al. "Studies of Synthetic Peptide Analogs of the Amphipathic Helix." The Journal of Biological Chemistry, vol. 260, Iss. 18, Aug. 25, 1985, pp. 10248-10255.

(Continued)

*Primary Examiner* — Jeffrey E. Russel
(74) *Attorney, Agent, or Firm* — Fenwick & West LLP

(57) ABSTRACT

The disclosure provides apolipoprotein C-II (apoC-II) mimetic peptides and methods for treating hypertriglyceridemia in a patient with an effective amount of an apoC-II mimetic peptide.

30 Claims, 58 Drawing Sheets

Specification includes a Sequence Listing.

(56) References Cited

OTHER PUBLICATIONS

Anderson, F. et al. "Dyslipidaemic Pancreatitis Clinical Assessment and Analysis of Disease Severity and Outcomes." Pancreatology, vol. 9, 2009, pp. 252-257.
Baca, M. et al. "Chemical Ligation of Cysteine-Containing Peptides: Synthesis of a 22 kDa Tethered Dimer of HIV-1 Protease." J. Am. Chem. Soc., vol. 117, Iss. 7, 1995, pp. 1881-1887.
Berglund, L. et al., "Evaluation and treatment of hypertriglyceridemia: an Endocrine Society clinical practice guideline," The Journal of Clinical Endocrinology & Metabolism, 2012, vol. 97, No. 9, pp. 2969-2989.
Breckenridge, W. C. et al. "Hypertriglyceridemia Associated with Deficiency of Apolipoprotein C-II." The New England Journal of Medicine, vol. 298, Jun. 8, 1978, pp. 1265-1273.
Brouillette, C.G. et al., "Structural models of human apolipoprotein AI," Biochimica et Biophysica Acta (BBA)—Lipids and Lipid Metabolism, 1995, vol. 1256, No. 2, pp. 103-129.
Budoff, M., "Triglycerides and triglyceride-rich lipoproteins in the causal pathway of cardiovascular disease," The American Journal of Cardiology, 2016, vol. 118, No. 1, pp. 138-145.
Chan, D. C. et al. "Postprandial Hypertriglyceridemia and Cardiovascular Disease: Current and Future Therapies." Current Atherosclerosis Reports, vol. 15, Iss. 3, Feb. 28, 2013, pp. 309-318.
Dominguez-Munoz, J. E. et al. "Hyperlipidemia in Acute Pancreatitis: Relationship with Etiology, Onset, and Severity of the Disease." International Journal of Pancreatology, vol. 10, 1991, pp. 261-267.
Fojo, S.S. et al., "Hypertriglyceridaemia due to genetic defects in lipoprotein lipase and apolipoprotein C-II," Journal of Internal Medicine, 1992, vol. 231, No. 6, pp. 669-677.
Friedan, C. et al. "Concerning the Structure of apoE." Protein Science, vol. 22, Iss. 12, Dec. 2013, pp. 1820-1825.
Huang, Y. et al. "Apolipoprotein E: Structure and Function in Lipid Metabolism, Neurobiology, and Alzheimer's Diseases." Neurobiology of Disease, vol. 72, Part A, Dec. 2014, pp. 3-12.
Kei, A. A. et al. "A Review of the Role of Apolipoprotein C-II in a Lipoprotein Metabolism and Cardiovascular Disease." Metabolism, vol. 61, Iss. 7, Jul. 2012, pp. 906-921.
Kritchevsky. D. et al., "Fatty acids, triglyceride structure, and lipid metabolism," The Journal of Nutritional Biochemistry, 1995, vol. 6, No. 4, pp. 172-178.
Kusminski, C.M. et al., "MitoNEET-driven alterations in adipocyte mitochondrial activity reveal a crucial adaptive process that preserves insulin sensitivity in obesity," Nature Medicine, 2012, vol. 18, No. 10, pp. 1539-1551.
Liu, C-F. et al. "Acyl Disulfide-Mediated Intramolecular Acylation for Orthogonal Coupling Between Unprotected Peptide Segments. Mechanism and Application." Tetrahedron Letters, vol. 37, Iss. 7, 1996, pp. 933-936.
Liu, C-F. et al. "Chemical Ligation Approach to Form a Peptide Bond Between Unprotected Peptide Segments. Concept and Model Study." Journal of the American Chemical Society, vol. 116, Iss. 10, 1994, pp. 4149-4153.
Liu, C-F. et al. "Peptide Segment Ligation Strategy Without use of Protecting Groups." Proc. Natl. Acad. Sci. USA, vol. 91, Jul. 5, 1994, pp. 6584-6588.
Mahadero et al., "Absorption of Intralipid and Interferences from Nutrients Infused into the Peritoneal Cavity of the Rat." American Journal of Surgery, Jul. 1992, vol. 164, pp. 45-50.
Mishra, V.K. et al., "Effect of the Arrangement of Tandem Repeating Units of Class A Amphipathic-Helixes on Lipid Interaction," Journal of Biological Chemistry, 1995, vol. 270, No. 4, pp. 1602-1611.
Mishra, V.K. et al., "Interactions of synthetic peptide analogs of the class A amphipathic helix with lipids. Evidence for the snorkel hypothesis," Journal of Biological Chemistry, 1994, vol. 269, No. 10, pp. 7185-7191.
Nakagawa, S. H. et al. "The Use of Polymer-Bound Oximes for the Synthesis of Large Peptides Usable in Segment Condensation: Synthesis of a 44 Amino Acid Amphiphilic Peptide Model of Apolipoprotein A-1." Journal of the American Chemical Society, vol. 107, Iss. 24, 1985, pp. 4087-7092.
Olivecrona, G. et al. "Lipid Binding of Apolipoprotein CII is Required for Stimulation of Lipoprotein Lipase Activity Against Apolipoprotein Cii-Deficient Chylomicrons." Arteriosclerosis, Thrombosis, and Vascular Biology, vol. 19, Iss. 8, Aug. 1997, pp. 1545-1549.
Qu, S. et al., "Effects of apoA-V on HDL and VLDL metabolism in APOC3 transgenic mice," Journal of Lipid Research, 2007, vol. 48, No. 7, pp. 1476-1487.
Rasouli, H. et al., "The long term kinetic of plasma lipids and lipoproteins in tyloxapol injected rats," Journal of Clinical and Diagnostic Research, 2016, vol. 10, No. 6, pp. BF01-BF05.
Remaley, A. T. et al. "Synthetic Amphipathic Helical Peptides Promote Lipid Efflux from Cells by an ABCA1-Dependent and an ABCA1-Independent Pathway." Journal of Lipid Research, vol. 44, 2003, pp. 828-836.
Sakurai, T. et al., "Creation of apolipoprotein C-II (ApoC-II) mutant mice and correction of their hypertriglyceridemia with an ApoC-II mimetic peptide," Journal of Pharmacology and Experimental Therapeutics, 2016, vol. 356, No. 2, pp. 341-353.
Schnolzer, M. et al. "Constructing Proteins by Dovetailing Unprotected Synthetic Peptides: Backbone-Engineered HIV Protease." Science, vol. 256, Iss. 5054, Apr. 10, 1992, pp. 221-225.
Shen, Y. et al., "Apolipoprotein CII from rainbow trout (Oncorhynchus mykiss) is functionally active but structurally very different from mammalian apolipoprotein CII," Gene, 2000, vol. 254, pp. 189-198.
Tam, J. P. et al. "Specificity and Formation of Unusual Amino Acids of an Amide Ligation Strategy for Unprotected Peptides." International Journal of Peptide & Protein Research, vol. 45, Iss. 3, Mar. 1995, pp. 209-216.
Tuzcu, K. et al., "Oral intralipid emulsion use: a novel therapeutic approach to pancreatic β-cell injury caused by malathion toxicity in rats," Drug and Chemical Toxicology, 2014, vol. 37, No. 3, pp. 261-267.
Venkatachalapathi, Y.V. et al., "Effect of end group blockage on the properties of a class A amphipathic helical peptide," Proteins: Structure, Function, and Bioinformatics, 1993, vol. 15, No. 4, pp. 349-359.
Viljoen, A. et al. "Diagnosis and Treatment of Severe Hypertriglyceridemia." Expert Review of Cardiovascular Therapy, vol. 10, Iss. 4, 2012, pp. 505-514.
Yamashiro, D. et al. "New Segment Synthesis of α-inhibin-92 by the Acyl Disulfide Method." International Journal of Peptide and Protein Research, vol. 31, Iss. 3, Mar. 1988, pp. 322-334.
Yancey, P.G. et al., "Efflux of cellular cholesterol and phospholipid to lipid-free apolipoproteins and class A amphipathic peptides," Biochemistry, 1995, vol. 34, No. 24, pp. 7955-7965.
Zdunek. J. et al., "Global structure and dynamics of human apolipoprotein CII in complex with micelles: evidence for increased mobility of the helix involved in the activation of lipoprotein lipase," Biochemistry, 2003, vol. 42, No. 7, pp. 1872-1889.
Zhang, Y.L. et al., "Regulation of hepatic apolipoprotein B-lipoprotein assembly and secretion by the availability of fatty acids I. Differential response to the delivery of fatty acids via albumin or remnant-like emulsion particles," Journal of Biological Chemistry, 2004, vol. 279, No. 18, pp. 19362-19374.
Storjohann, R. et al. "Structure of a Biologically Active Fragment of Human Serum Apolipoprotein C-II in the Presence of Sodium Dodecyl Sulfate and Dodecylphosphocholine." Biochimica et Biophysica Acta (BBA)—Molecular and Cell Biology of Lipids, vol. 1486, Iss. 2-3, Jul. 19, 2000, pp. 253-264.
Wolska, A. et al. "A Dual Apolipoprotein C-II Mimetic-Apolipoprotein C-III Antagonist Peptide Lowers Plasma Triglycerides." Science Translational Medicine, vol. 12, Iss. 528, Jan. 29, 2020, pp. 1-14.
Wolska, A. et al. "Apolipoprotein C-II: New Findings Related to Genetics, Biochemistry, and Role in Triglyceride Metabolism." Atherosclerosis, vol. 267, Dec. 2017, pp. 49-60.

* cited by examiner

| Species | | | | | | | | | | | | | | | | |
|---|---|---|---|---|---|---|---|---|---|---|---|---|---|---|---|---|
| Homo sapiens | T | Y | L | P | A | V | D | E | K | L | R | D | L | Y | S | K | S | T | A |
| Pan troglodytes | T | Y | L | P | A | V | D | E | K | L | R | D | L | Y | S | K | S | T | A |
| Macaca fascicularis | T | Y | L | P | A | V | D | E | K | L | R | D | L | Y | S | K | S | T | A |
| Macaca mulatta | T | Y | L | P | A | V | D | E | K | L | R | D | L | Y | S | K | S | T | A |
| Papio hamadryas | T | Y | L | P | A | V | D | E | K | L | R | D | L | Y | S | K | S | T | A |
| Callithrix jacchus | T | Y | L | H | T | V | D | E | K | L | R | D | M | Y | S | K | S | T | A |
| Mus musculus | T | Y | P | I | S | M | D | E | K | L | R | D | M | Y | S | K | S | S | A |
| Rattus norvegicus | T | Y | L | T | S | V | D | E | K | L | R | D | M | Y | S | K | S | S | A |
| Canis lupus familiaris | A | Y | P | T | T | M | D | E | K | I | R | D | I | Y | S | K | S | T | A |
| Bos taurus | T | Y | L | P | A | V | D | E | K | I | R | D | I | Y | S | K | S | T | A |
| Sus scrofa | T | Y | L | P | T | V | D | E | K | I | R | D | M | Y | S | K | S | T | A |
| Cavia porcellus | T | Y | L | P | A | V | D | E | T | I | R | D | I | Y | S | K | G | S | A |

FIG. 1

Delta4': DYLDAVWEKLRDLYSKFT mono-acyl-Delta4': DYLDAVWEKLRDLYSKFT
                          |
                        (C18)

di-acyl-Delta4': DYLDAVWEKLRDLYSKFT
                      |         |
                    (C18)     (C18)

FIG. 5

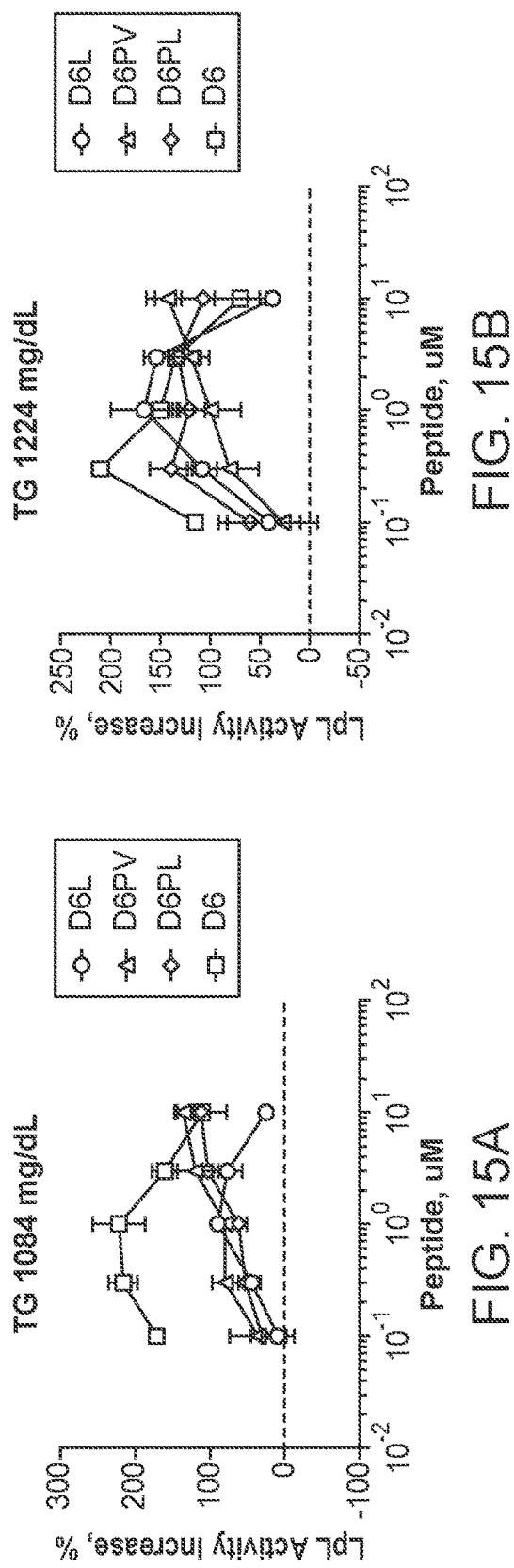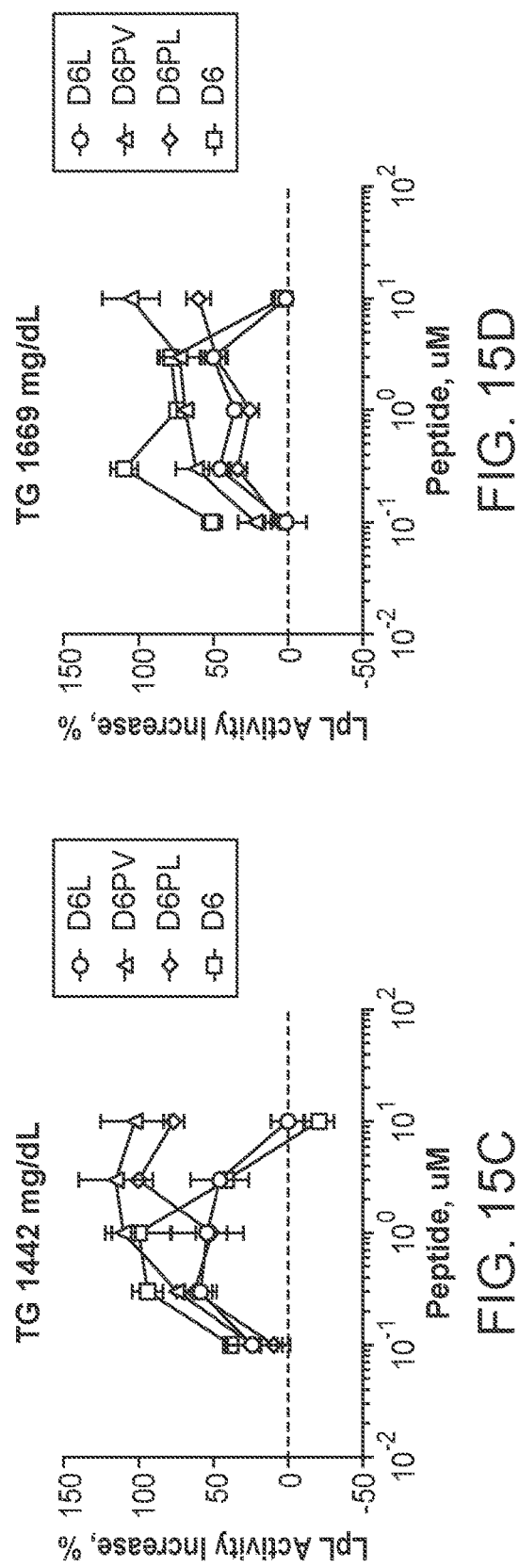

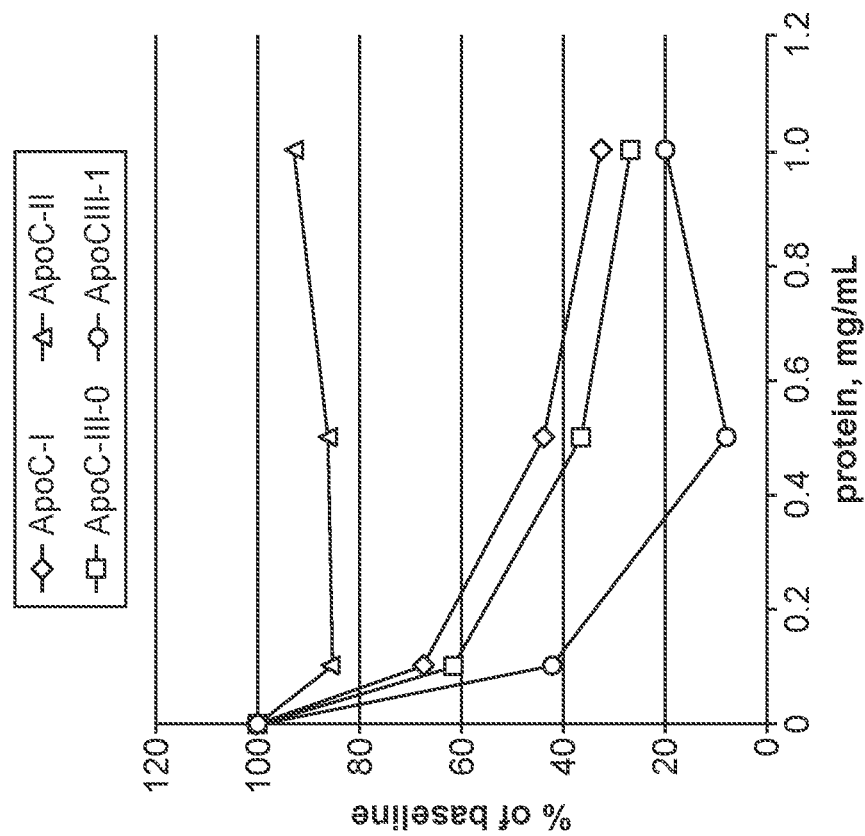
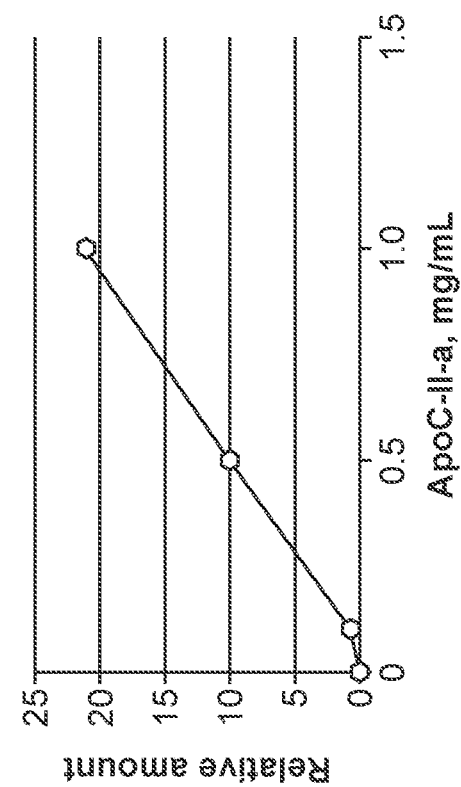
FIG. 29A
FIG. 29B

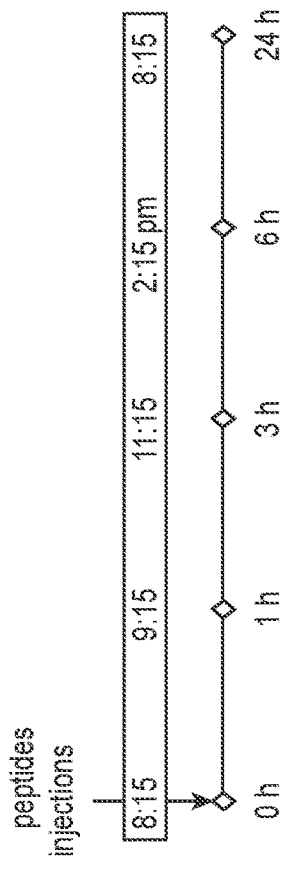
FIG. 36A
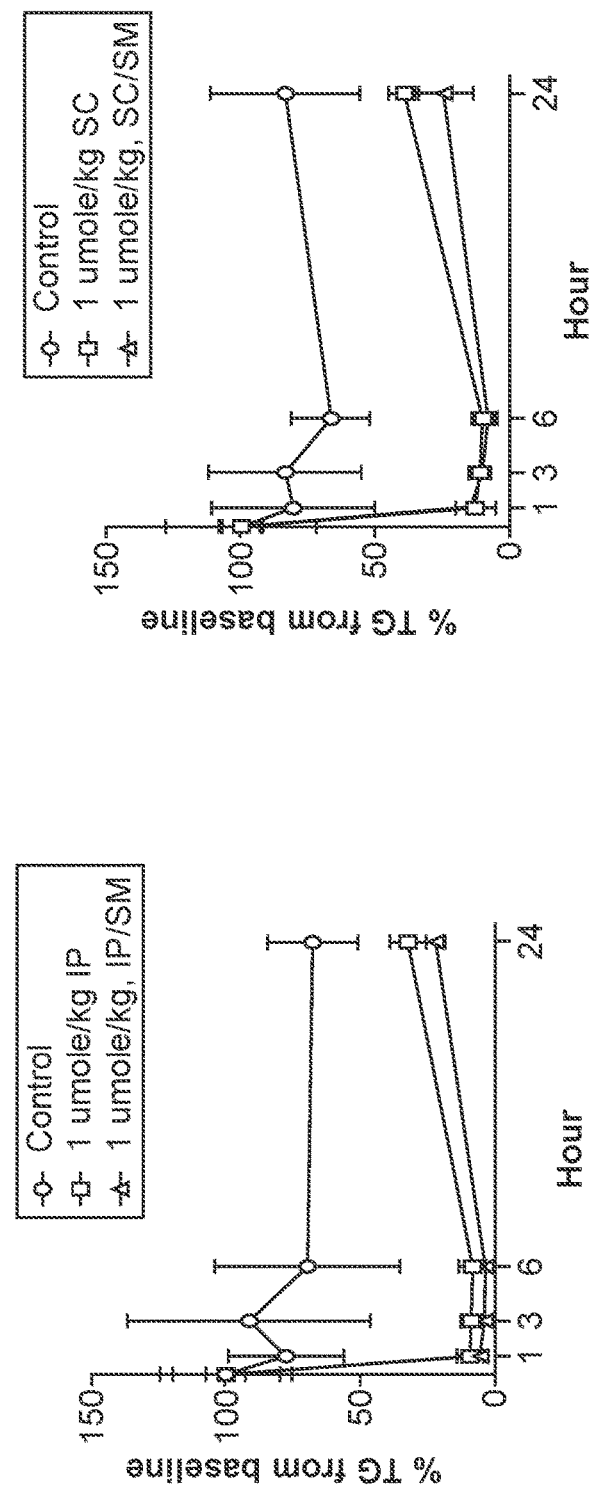
FIG. 36C
FIG. 36B

FIG. 52

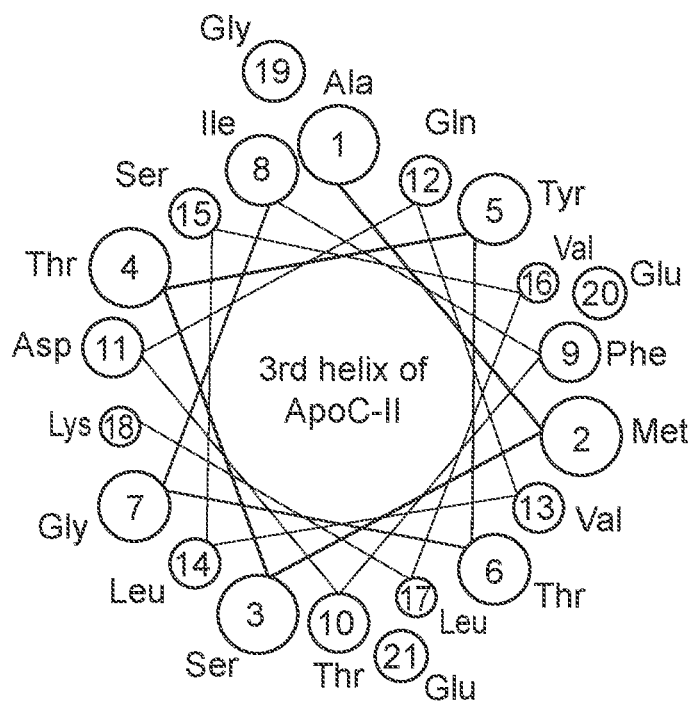
FIG. 54B
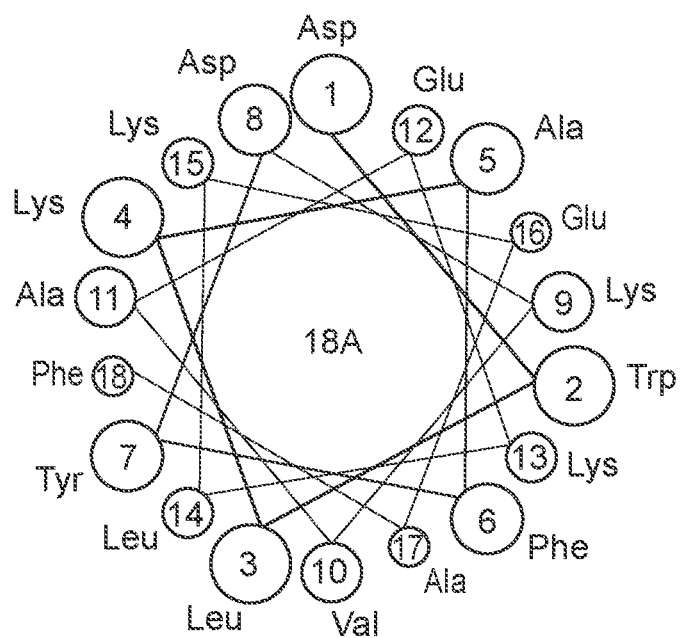
FIG. 54A
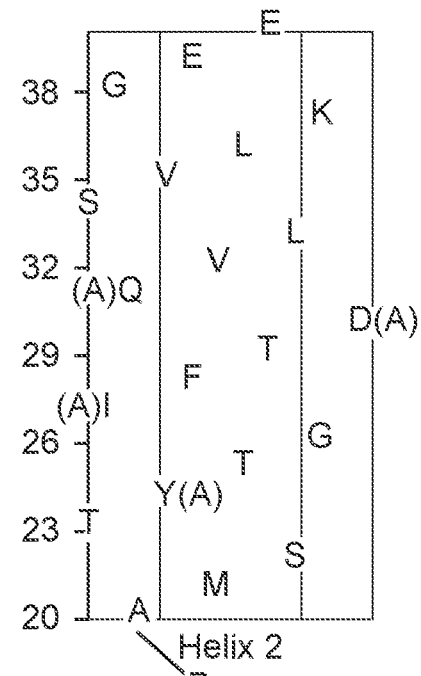
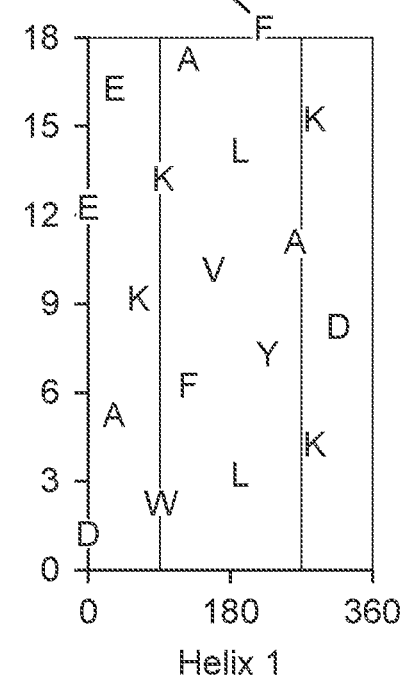
FIG. 54C

SEQUENCE LISTING

```
<160> NUMBER OF SEQ ID NOS: 81

<210> SEQ ID NO 1
<211> LENGTH: 79
<212> TYPE: PRT
<213> ORGANISM: Homo sapiens

<400> SEQUENCE: 1

Thr Gln Gln Pro Gln Gln Asp Glu Met Pro Ser Pro Thr Phe Leu Thr
1               5                   10                  15

Gln Val Lys Glu Ser Leu Ser Ser Tyr Trp Glu Ser Ala Lys Thr Ala
            20                  25                  30

Ala Gln Asn Leu Tyr Glu Lys Thr Tyr Leu Pro Ala Val Asp Glu Lys
        35                  40                  45

Leu Arg Asp Leu Tyr Ser Lys Ser Thr Ala Ala Met Ser Thr Tyr Thr
    50                  55                  60

Gly Ile Phe Thr Asp Gln Val Leu Ser Val Leu Lys Gly Glu Glu
65                  70                  75

<210> SEQ ID NO 2
<211> LENGTH: 40
<212> TYPE: PRT
<213> ORGANISM: Homo sapiens

<400> SEQUENCE: 2

Thr Tyr Leu Pro Ala Val Asp Glu Lys Leu Arg Asp Leu Tyr Ser Lys
```

```
1               5                   10                  15

Ser Thr Ala Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 3
<211> LENGTH: 22
<212> TYPE: PRT
<213> ORGANISM: Homo sapiens

<400> SEQUENCE: 3

Gln Val Lys Glu Ser Leu Ser Ser Tyr Trp Glu Ser Ala Lys Thr Ala
1               5                   10                  15

Ala Gln Asn Leu Tyr Glu
            20

<210> SEQ ID NO 4
<211> LENGTH: 13
<212> TYPE: PRT
<213> ORGANISM: Homo sapiens

<400> SEQUENCE: 4

Val Asp Glu Lys Leu Arg Asp Leu Tyr Ser Lys Ser Thr
1               5                   10

<210> SEQ ID NO 5
<211> LENGTH: 11
<212> TYPE: PRT
<213> ORGANISM: Homo sapiens

<400> SEQUENCE: 5

Gly Ile Phe Thr Asp Gln Val Leu Ser Val Leu
1               5                   10

<210> SEQ ID NO 6
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 6

Asp Tyr Leu Lys Glu Val Phe Glu Lys Leu Arg Asp Leu Tyr Glu Lys
1               5                   10                  15

Phe Thr Ala Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 7
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

Asp Tyr Leu Lys Glu Val Phe Glu Lys Leu Arg Asp Leu Tyr Glu Lys
1               5                   10                  15

Phe Thr Ala Ala Val Ser Thr Tyr Thr Gly Ile Phe Thr Asp Gln Val
            20                  25                  30

Leu Ser Val Leu Lys Gly Glu Glu
        35                  40

<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Tyr Leu Lys Glu Val Phe Glu Lys Leu Arg Asp Leu Tyr Glu Lys
1               5                   10                  15

Phe Thr Ala Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 9
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Tyr Leu Lys Glu Val Phe Glu Lys Leu Arg Asp Leu Tyr Glu Lys
1               5                   10                  15

Phe Thr Pro Ala Val Ser Thr Tyr Thr Gly Ile Phe Thr Asp Gln Val
            20                  25                  30

Leu Ser Val Leu Lys Gly Glu Glu
        35                  40

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Tyr Leu Lys Glu Val Phe Glu Lys Leu Arg Asp Leu Tyr Glu Lys
1               5                   10                  15

Phe Thr Pro Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 11
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

-continued

```
Asp Tyr Leu Lys Glu Val Phe Glu Lys Leu Arg Asp Leu Tyr Glu Lys
1               5                   10                  15

Phe Thr Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 12
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Tyr Leu Arg Glu Val Phe Glu Arg Leu Arg Asp Leu Tyr Glu Arg
1               5                   10                  15

Lys Thr Pro Ala Met Ser Thr Tyr Thr Gly Ile Phe Thr Asp Gln Val
            20                  25                  30

Leu Ser Val Leu Arg Gly Glu Glu
        35                  40

<210> SEQ ID NO 13
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 13

Asp Tyr Leu Lys Glu Val Phe Glu Lys Leu Arg Asp Leu Tyr Glu Lys
1               5                   10                  15

Phe Thr Ala Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 14
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 14

Asp Tyr Leu Lys Glu Val Phe Glu Lys Leu Arg Asp Leu Tyr Glu Lys
1               5                   10                  15

Lys Thr Pro Ala Leu Ser Thr Tyr Thr Gly Ile Phe Thr Asp Gln Val
            20                  25                  30

Leu Ser Val Leu Lys Gly Glu Glu
        35                  40
```

```
<210> SEQ ID NO 15
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 15

Asp Tyr Leu Lys Glu Val Phe Glu Lys Leu Arg Asp Leu Tyr Glu Lys
1               5                   10                  15

Lys Thr Ala Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 16
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 16

Asp Tyr Leu Lys Ala Val Phe Glu Lys Leu Arg Asp Leu Tyr Ser Lys
1               5                   10                  15

Phe Thr Ala Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 17
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 17

Asp Tyr Leu Lys Ala Val Phe Glu Lys Leu Arg Asp Leu Tyr Glu Lys
1               5                   10                  15

Phe Thr Ala Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 18
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (21)..(21)
<223> OTHER INFORMATION: Norleucine

<400> SEQUENCE: 18

Asp Tyr Leu Lys Ala Val Phe Glu Lys Leu Arg Asp Leu Tyr Ser Lys
1               5                   10                  15

Phe Phe Ala Ala Leu Ser Thr Tyr Thr Gly Ile Phe Thr Asp Gln Val
            20                  25                  30

Leu Ser Val Leu Lys Gly Glu Glu
            35                  40

<210> SEQ ID NO 19
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 19

Asp Tyr Leu Lys Ala Val Phe Glu Lys Leu Arg Asp Leu Tyr Ser Lys
1               5                   10                  15

Phe Thr Ala Ala Leu Ser Thr Ser Thr Gly Ile Phe Thr Asp Gln Val
            20                  25                  30

Leu Ser Val Leu Lys Gly Glu Glu
            35                  40

<210> SEQ ID NO 20
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 20

Asp Tyr Leu Lys Ala Val Phe Glu Lys Leu Arg Asp Leu Tyr Ser Lys
1               5                   10                  15

Phe Thr Ala Ala Leu Ser Thr Tyr Thr Gly Ile Phe Thr Asp Arg Val
            20                  25                  30

Leu Ser Val Leu Lys Gly Glu Glu
            35                  40

<210> SEQ ID NO 21
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 21
```

Asp Tyr Leu Lys Ala Val Phe Glu Lys Leu Arg Asp Leu Tyr Ser Lys
1               5                   10                  15

Phe Thr Ala Ala Leu Ser Thr Tyr Thr Gly Ile Phe Thr Asp Lys Val
                20                  25                  30

Leu Ser Val Leu Lys Gly Glu Glu
            35                  40

<210> SEQ ID NO 22
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Norleucine

<400> SEQUENCE: 22

Lys Arg Asp Leu Tyr Glu Lys Lys Phe Ala Ala Leu Ser Thr Tyr Thr
1               5                   10                  15

Gly Ile Phe Thr Asp Gln Val Leu Ser Val Leu Lys Gly Glu Glu
                20                  25                  30

<210> SEQ ID NO 23
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 23

Asp Tyr Leu Lys Ala Val Phe Glu Lys Leu Arg Asp Leu Tyr Ser Lys
1               5                   10                  15

Phe Thr Ala Ala Leu Ser Thr Tyr Thr Gly Ile Phe Thr Asp Gln Val
                20                  25                  30

Leu Ser Val Leu Lys Gly Glu Glu
            35                  40

<210> SEQ ID NO 24
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 24

Asp Tyr Leu Lys Ala Val Phe Glu Lys Lys Arg Asp Leu Tyr Ser Lys
1               5                   10                  15

Phe Thr Ala Ala Leu Ser Thr Tyr Thr Gly Ile Phe Thr Asp Gln Val
                20                  25                  30

Leu Ser Val Leu Lys Gly Glu Glu
            35                  40

```
<210> SEQ ID NO 25
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Tyr Leu Lys Ala Val Phe Glu Lys Leu Arg Asp Leu Tyr Ser Lys
1               5                   10                  15

Phe Thr Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 26
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Tyr Leu Lys Ala Val Phe Glu Lys Leu Arg Asp Leu Tyr Glu Lys
1               5                   10                  15

Phe Thr Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 27
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Tyr Leu Lys Ala Val Phe Glu Lys Leu Arg Asp Leu Tyr Lys Lys
1               5                   10                  15

Phe Thr Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 28
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Tyr Leu Lys Ala Val Phe Glu Lys Leu Lys Asp Leu Tyr Ser Lys
1               5                   10                  15

Phe Thr Pro Ala Met Ser Thr Tyr Thr Gly Ile Phe Thr Asp Gln Val
            20                  25                  30

Leu Ser Val Leu Lys Gly Glu Glu
        35                  40
```

<210> SEQ ID NO 29
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Trp Leu Lys Ala Val Phe Glu Lys Leu Arg Asp Leu Tyr Ser Lys
1               5                   10                  15

Phe Thr Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 30
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Tyr Leu Lys Ala Val Phe Glu Lys Leu Arg Asp Leu Tyr Ser Lys
1               5                   10                  15

Phe Phe Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 31
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Tyr Leu Lys Ala Phe Tyr Glu Lys Leu Arg Asp Leu Leu Ser Lys
1               5                   10                  15

Ala Phe Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 32
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Tyr Leu Lys Ala Val Lys Glu Lys Leu Arg Asp Leu Tyr Ser Lys
1               5                   10                  15

Phe Thr Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 33
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Tyr Leu Lys Ala Val Phe Glu Lys Lys Arg Asp Leu Tyr Ser Lys
1               5                   10                  15

Phe Thr Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 34
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Tyr Leu Lys Ala Val Phe Glu Lys Leu Arg Asp Leu Tyr Ser Lys
1               5                   10                  15

Lys Thr Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 35
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Tyr Leu Lys Ala Val Phe Glu Lys Leu Arg Asp Leu Tyr Ser Lys
1               5                   10                  15

Phe Thr Ala Ala Lys Ser Thr Tyr Thr Gly Ile Phe Thr Asp Gln Val
            20                  25                  30

Leu Ser Val Leu Lys Gly Glu Glu
        35                  40

<210> SEQ ID NO 36
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Lys Ala Val Phe Glu Lys Leu Arg Asp Leu Tyr Ser Lys Phe Thr Ala
1               5                   10                  15

Ala Lys Ser Thr Tyr Thr Gly Ile Phe Thr Asp Gln Val Leu Ser Val
            20                  25                  30

Leu Lys Gly Glu Glu

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Val Phe Glu Lys Leu Arg Asp Leu Tyr Ser Lys Phe Thr Ala Ala
1               5                   10                  15

Lys Ser Thr Tyr Thr Gly Ile Phe Thr Asp Gln Val Leu Ser Val Leu
            20                  25                  30

Lys Gly Glu Glu
        35

<210> SEQ ID NO 38
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Lys Leu Arg Asp Leu Tyr Ser Lys Phe Thr Ala Ala Lys Ser Thr
1               5                   10                  15

Tyr Thr Gly Ile Phe Thr Asp Gln Val Leu Ser Val Leu Lys Gly Glu
            20                  25                  30

Glu

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Arg Asp Leu Tyr Ser Lys Phe Thr Ala Ala Lys Ser Thr Tyr Thr Gly
1               5                   10                  15

Ile Phe Thr Asp Gln Val Leu Ser Val Leu Lys Gly Glu Glu
            20                  25                  30

<210> SEQ ID NO 40
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Leu Tyr Ser Lys Phe Thr Ala Ala Lys Ser Thr Tyr Thr Gly Ile
1               5                   10                  15

Phe Thr Asp Gln Val Leu Ser Val Leu Lys Gly Glu Glu
            20                  25

<210> SEQ ID NO 41
<211> LENGTH: 26
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 41

Asp Lys Phe Thr Ala Ala Lys Ser Thr Tyr Thr Gly Ile Phe Thr Asp
1               5                   10                  15

Gln Val Leu Ser Val Leu Lys Gly Glu Glu
            20                  25

<210> SEQ ID NO 42
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 42

Asp Tyr Leu Lys Glu Val Phe Glu Lys Leu Arg Asp Leu Tyr Ser Lys
1               5                   10                  15

Phe Thr Ala Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 43
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Trp Leu Lys Ala Val Phe Glu Lys Leu Arg Asp Leu Tyr Glu Lys
1               5                   10                  15

Phe Thr Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 44
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Tyr Leu Lys Ala Val Phe Glu Lys Leu Arg Asp Leu Tyr Glu Lys
1               5                   10                  15

Phe Phe Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 45
```

```
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Trp Leu Lys Ala Val Phe Glu Lys Leu Arg Asp Leu Tyr Glu Lys
1               5                   10                  15

Phe Phe Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 46
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 46

Asp Trp Leu Lys Ala Val Phe Glu Lys Leu Arg Asp Leu Tyr Glu Lys
1               5                   10                  15

Phe Thr Pro Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 47
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine

<400> SEQUENCE: 47

Asp Tyr Leu Lys Ala Val Phe Glu Lys Leu Arg Asp Leu Tyr Glu Lys
1               5                   10                  15

Phe Phe Pro Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 48
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Norleucine
```

```
<400> SEQUENCE: 48

Asp Trp Leu Lys Ala Val Phe Glu Lys Leu Arg Asp Leu Tyr Glu Lys
1               5                   10                  15

Phe Phe Pro Ala Leu Ser Thr Tyr Thr Gly Ile Phe Thr Asp Gln Val
            20                  25                  30

Leu Ser Val Leu Lys Gly Glu Glu
        35                  40

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Met Ser Thr Tyr Thr Gly Ile Phe Thr Asp Gln Val Leu Ser Val
1               5                   10                  15

Leu Lys Gly Glu Glu
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Met Ser Thr Tyr Thr Gly Ile Phe Thr Asp Gln Val Leu Ser Val
1               5                   10                  15

Leu Lys Gly Glu Glu
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Lys Ser Thr Tyr Thr Gly Ile Phe Thr Asp Gln Val Leu Ser Val
1               5                   10                  15

Leu Lys Gly Glu Glu
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Met Ser Thr Tyr Thr Gly Ile Phe Thr Asp Gln Val Leu Ser Val
1               5                   10                  15

Leu Lys Gly Glu Glu
            20
```

```
<210> SEQ ID NO 53
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Tyr Leu Lys Glu Val Phe Glu Lys Leu Arg Asp Leu Tyr Glu Lys
1               5                   10                  15

Phe Phe Pro Ala Val Ser Thr Tyr Thr Gly Ile Phe Thr Asp Gln Val
            20                  25                  30

Leu Ser Val Leu Lys Gly Glu Glu
            35                  40

<210> SEQ ID NO 54
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Aib
<220> FEATURE:
<221> NAME/KEY: MOD_RES
<222> LOCATION: (17)..(17)
<223> OTHER INFORMATION: Aib

<400> SEQUENCE: 54

Asp Tyr Leu Lys Glu Val Xaa Glu Lys Leu Arg Asp Leu Tyr Glu Lys
1               5                   10                  15

Xaa Phe Pro Ala Val Ser Thr Tyr Thr Gly Ile Phe Thr Asp Gln Val
            20                  25                  30

Leu Ser Val Leu Lys Gly Glu Glu
            35                  40

<210> SEQ ID NO 55
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Lys Val Lys Glu Phe Leu Ser Glu Tyr Trp Glu Lys Ala Lys Glu
1               5                   10                  15

Phe Ala Pro Ala Val Ser Thr Tyr Thr Gly Ile Phe Thr Asp Gln Val
            20                  25                  30

Leu Ser Val Leu Lys Gly Glu Glu
            35                  40

<210> SEQ ID NO 56
<211> LENGTH: 40
<212> TYPE: PRT
<213> ORGANISM: Homo sapiens

<400> SEQUENCE: 56

Asp Trp Leu Lys Ala Phe Tyr Asp Lys Val Ala Glu Lys Leu Lys Glu
1               5                   10                  15
```

Ala Phe Pro Ala Met Ser Thr Tyr Thr Gly Ile Phe Thr Asp Gln Val
            20                  25                  30

Leu Ser Val Leu Lys Gly Glu Glu
        35                  40

<210> SEQ ID NO 57
<211> LENGTH: 19
<212> TYPE: PRT
<213> ORGANISM: Homo sapiens

<400> SEQUENCE: 57

Thr Tyr Leu Pro Ala Val Asp Glu Lys Leu Arg Asp Leu Tyr Ser Lys
1               5                   10                  15

Ser Thr Ala

<210> SEQ ID NO 58
<211> LENGTH: 19
<212> TYPE: PRT
<213> ORGANISM: Pan troglodytes

<400> SEQUENCE: 58

Thr Tyr Leu Pro Ala Val Asp Glu Lys Leu Arg Asp Leu Tyr Ser Lys
1               5                   10                  15

Ser Thr Ala

<210> SEQ ID NO 59
<211> LENGTH: 19
<212> TYPE: PRT
<213> ORGANISM: Macaca fascicularis

<400> SEQUENCE: 59

Thr Tyr Leu Pro Ala Val Asp Glu Lys Leu Arg Asp Leu Tyr Ser Lys
1               5                   10                  15

Ser Thr Ala

<210> SEQ ID NO 60
<211> LENGTH: 19
<212> TYPE: PRT
<213> ORGANISM: Macaca mulatta

<400> SEQUENCE: 60

Thr Tyr Leu Pro Ala Val Asp Glu Lys Leu Arg Asp Leu Tyr Ser Lys
1               5                   10                  15

Ser Thr Ala

<210> SEQ ID NO 61
<211> LENGTH: 19
<212> TYPE: PRT
<213> ORGANISM: Papio hamadryas

<400> SEQUENCE: 61

Thr Tyr Leu Pro Ala Val Asp Glu Lys Leu Arg Asp Leu Tyr Ser Lys
1               5                   10                  15

Ser Thr Ala

<210> SEQ ID NO 62
<211> LENGTH: 19
<212> TYPE: PRT
<213> ORGANISM: Callithrix jacchus

<400> SEQUENCE: 62

-continued

Thr Tyr Leu His Thr Val Asp Glu Lys Leu Arg Asp Met Tyr Ser Lys
1               5                   10                  15

Ser Thr Ala

<210> SEQ ID NO 63
<211> LENGTH: 19
<212> TYPE: PRT
<213> ORGANISM: Mus musculus

<400> SEQUENCE: 63

Thr Tyr Pro Ile Ser Met Asp Glu Lys Leu Arg Asp Met Tyr Ser Lys
1               5                   10                  15

Ser Ser Ala

<210> SEQ ID NO 64
<211> LENGTH: 19
<212> TYPE: PRT
<213> ORGANISM: Rattus norvegicus

<400> SEQUENCE: 64

Thr Tyr Leu Thr Ser Val Asp Glu Lys Leu Arg Asp Met Tyr Ser Lys
1               5                   10                  15

Ser Ser Ala

<210> SEQ ID NO 65
<211> LENGTH: 19
<212> TYPE: PRT
<213> ORGANISM: Canis lupus familiaris

<400> SEQUENCE: 65

Ala Tyr Pro Thr Thr Met Asp Glu Lys Ile Arg Asp Ile Tyr Ser Lys
1               5                   10                  15

Ser Thr Ala

<210> SEQ ID NO 66
<211> LENGTH: 19
<212> TYPE: PRT
<213> ORGANISM: Bos taurus

<400> SEQUENCE: 66

Thr Tyr Leu Pro Ala Val Asp Glu Lys Ile Arg Asp Ile Tyr Ser Lys
1               5                   10                  15

Ser Thr Ala

<210> SEQ ID NO 67
<211> LENGTH: 19
<212> TYPE: PRT
<213> ORGANISM: Sus scrofa

<400> SEQUENCE: 67

Thr Tyr Leu Pro Thr Val Asp Glu Lys Ile Arg Asp Met Tyr Ser Lys
1               5                   10                  15

Ser Thr Ala

<210> SEQ ID NO 68
<211> LENGTH: 19
<212> TYPE: PRT
<213> ORGANISM: Cavia porcellus

<400> SEQUENCE: 68

Thr Tyr Leu Pro Ala Val Asp Glu Thr Ile Arg Asp Ile Tyr Ser Lys

```
1               5                   10                  15
Gly Ser Ala

<210> SEQ ID NO 69
<211> LENGTH: 18
<212> TYPE: PRT
<213> ORGANISM: Homo sapiens

<400> SEQUENCE: 69

Thr Tyr Leu Pro Ala Val Asp Glu Lys Leu Arg Asp Leu Tyr Ser Lys
1               5                   10                  15

Ser Thr

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Tyr Leu Lys Ala Val Phe Glu Lys Leu Arg Asp Leu Tyr Ser Lys
1               5                   10                  15

Phe Thr

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Tyr Leu Lys Glu Val Phe Glu Lys Leu Arg Asp Leu Tyr Ser Lys
1               5                   10                  15

Phe Thr

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Tyr Leu Lys Glu Val Phe Glu Lys Leu Arg Asp Leu Tyr Glu Lys
1               5                   10                  15

Phe Thr

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Tyr Leu Asp Ala Val Trp Glu Lys Leu Arg Asp Leu Tyr Ser Lys
1               5                   10                  15
```

```
Phe Thr

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Tyr Leu Lys Glu
1               5

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Gly Glu Glu
1

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Met Ser Thr Tyr Thr Gly Ile Phe Thr Asp Gln Val Leu Ser Val
1               5                   10                  15

Leu Lys Gly Glu Glu
            20

<210> SEQ ID NO 77
<211> LENGTH: 18
<212> TYPE: PRT
<213> ORGANISM: Homo sapiens

<400> SEQUENCE: 77

Asp Trp Leu Lys Ala Phe Tyr Asp Lys Val Ala Glu Lys Leu Lys Glu
1               5                   10                  15

Ala Phe

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Tyr Leu Lys Ala
1               5

<210> SEQ ID NO 79
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 79

Arg Gly Glu Glu
1

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Met Ser Thr Tyr Thr
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Lys Ser Thr Tyr Thr
1               5
```

APOC-II MIMETIC PEPTIDES

CROSS REFERENCE TO RELATED APPLICATIONS

This application is the National Stage of International Application No. PCT/US2018/014532, filed Jan. 19, 2018, which claims the benefit of U.S. Provisional Application Nos. 62/476,531, filed Mar. 24, 2017, 62/476,535, filed Mar. 24, 2017, and 62/448,358, filed Jan. 19, 2017.

STATEMENT REGARDING FEDERALLY SPONSORED RESEARCH OR DEVELOPMENT

This invention was created in the performance of Cooperative Research and Development Agreement No. HL-CR-16-005 with the National Institutes of Health, an Agency of the Department of Health and Human Services. The Government of the United States has certain rights in this invention.

SEQUENCE LISTING

The instant application contains a Sequence Listing which has been submitted via EFS-Web and is hereby incorporated herein by reference in its entirety. Said ASCII copy, created on Jan. 13, 2021, is named 36431US_CRF_sequencelisting.txt, and is 32,768 bytes in size.

BACKGROUND

Hypertriglyceridemia is typically defined as serum triglyceride levels over 150 mg/dL (Berglund et al., *J. Clin. Endocrinol. Metab.* 97:2969-2989, 2012). Patients with moderate increases in triglycerides are at risk for cardiovascular disease (Budoff, *Am J Cardiol* 118:138-45, 2016). Patients with severe hypertriglyceridemia are additionally at risk for acute pancreatitis (Viljoen and Wierzbicki, *Expert Rev Cardiovasc Ther* 10:505-514, 2012).

Hypertriglyceridemia is most commonly secondary to obesity, diabetes mellitus, pregnancy, alcohol and a wide variety of drugs (Anderson et al., *Pancreatology* 9:252-257, 2009; Dominguez-Munoz et al., *Int. J. Pancreatol.* 10:261-267, 1991). Triglycerides are enriched in chylomicrons and very low density lipoprotein (VLDL), and lipolysis by lipoprotein lipase (LPL) is a critical step in the catabolism of these triglyceride-rich lipoprotein particles. Rarely, hypertriglyceridemia is the result of genetic defects in LPL or apoC-II, an obligate activator of LPL (Fojo et al., *J. Intern. Med.* 231:669-677, 1992) or in other genes.

Fibrates and supplements rich in omega-3 polyunsaturated fatty acids, such as fish oils, are the main treatment for hypertriglyceridemia (Berglund et al., *J. Clin. Endocrinol. Metab.* 97:2969-2989, 2012). However, it has not been clearly demonstrated that these agents are efficacious in lowering the risks associated with elevated triglycerides, such as cardiovascular disease (Budoff, *Am J Cardiol* 118:138-45, 2016).

There is, therefore, a need for new therapeutic agents for treatment of hypertriglyceridemia, both common forms of hypertriglyceridemia and hypertriglyceridemia caused by genetic defects.

SUMMARY

We have designed and produced apoC-II mimetic peptides that possess the ability to lower the triglyceride level both in vitro and in vivo. These peptides can be used for treating hypertriglyceridemia.

In typical embodiments, the apoC-II mimetic peptide is a multihelical peptide in which one or more of the helical domains is amphipathic, conferring on the peptide the ability to bind to lipids and/or to the surface of lipoproteins, and another of the helical domains activates LPL. In certain embodiments, the apoC-II mimetic peptide is a bihelical peptide comprising a first helical domain, a hinge region, and a second helical domain in order from N-terminus to C-terminus, in which the first helical domain is amphipathic and the second helical domain activates LPL. We have found that a variety of amphipathic helices are suitable, with some modeled on amphipathic helices of known apolipoproteins, such as apoC-II. We have also found that the peptides' ability to lower triglyceride is not limited to activation of LPL, allowing their use in disorders in which LPL is diminished or absent, and that they can displace apoC-III from the surface of lipoproteins, allowing their use in disorders in which apoC-III levels are elevated.

Accordingly, in a first aspect, provided herein is an isolated apoC-II mimetic peptide of no more than 50 amino acids, comprising from N-terminus to C-terminus: a first helical domain, a hinge region, and a second helical domain, wherein the first helical domain is amphipathic, wherein the apoC-II mimetic peptide is not a peptide of SEQ ID NO: 56.

In some embodiments, the first domain of the isolated apoC-II mimetic peptide is native helix 1 of apoC-II. In some other embodiments, the first domain of the isolated apoC-II mimetic peptide is a variant of helix 1 of apoC-II. In some embodiments, the first domain of the isolated apoC-II mimetic peptide is native helix 2 of apoC-II In some other embodiments, the first domain of the isolated apoC-II mimetic peptide is a variant of helix 2 of apoC-II.

In some embodiments, the variant of helix 2 of apoC-II comprises elongation of helix 2 of ApoC-II. In various embodiments, the helix 2 of apoC-II is elongated by 1-10 amino acids at the N-terminus. In certain embodiments, the helix 2 of apoC-II is elongated by 1 amino acid at the N-terminus. In some of these embodiments, the amino acid is aspartic acid. In certain embodiments, the helix 2 of apoC-II is elongated by 2 amino acids at the N-terminus. In some of these embodiments, the amino acids are lysine and alanine from N-terminus to C-terminus. In certain embodiments, the helix 2 of apoC-II is elongated by 5 amino acids at the N-terminus. In some of these embodiments, the helix 2 of apoC-II is elongated by the native upstream amino acid sequence of human apoC-II, or a mutant of native upstream amino acid sequence of human apoC-II. In specific embodiments, the variant of helix 2 of apoC-II comprises an aspartic acid at position 40. In specific embodiments, the variant of helix 2 of apoC-II comprises a tyrosine or a tryptophan at position 41. In specific embodiments, the variant of helix 2 of apoC-II comprises a leucine at position 42. In specific embodiments, the variant of helix 2 of apoC-II comprises a lysine or an arginine at position 43. In specific embodiments, the variant of helix 2 of apoC-II comprises an alanine or a glutamic acid at position 44. In particular embodiments, the variant of helix 2 of apoC-II comprises an aspartic acid at position 40, a tyrosine at position 41, a leucine at position 42, a lysine at position 43, and a glutamic acid at position 44 (SED ID NO: 75).

In some embodiments, the variant of helix 2 of apoC-II comprises truncation of helix 2 of apoC-II. In some of these embodiments, the amino acid residues 45-46 of native helix 2 of apoC-II are deleted. In some of these embodiments, the amino acid residues 45-48 of native helix 2 of apoC-II are deleted. In some of these embodiments, the amino acid residues 45-49 of native helix 2 of apoC-II are deleted. In some of these embodiments, the amino acid residues 45-50 of native helix 2 of apoC-II are deleted. In some of these embodiments, the amino acid residues 45-53 of native helix 2 of apoC-II are deleted.

In some embodiments, the variant of helix 2 of apoC-II comprises at least one mutation of helix 2 of apoC-II. In some of these embodiments, the mutation is an amino acid substitution. In certain embodiments, an original amino acid of helix 2 of apoC-II is substituted by a natural amino acid. In certain embodiments, an original amino acid of helix 2 of apoC-II is substituted by an unnatural amino acid. In certain embodiments, an original amino acid of helix 2 of apoC-II is substituted by an amino acid analog. In specific embodiments, the amino acid substitution is at position 45. In some of these embodiments, the valine at position 45 is substituted by phenylalanine. In specific embodiments, the amino acid substitution is at position 46. In some of these embodiments, the aspartic acid at position 46 is substituted by a phenylalanine. In some of these embodiments, the aspartic acid at position 46 is substituted by a lysine. In some of these embodiments, the aspartic acid at position 46 is substituted by an aminoisobutyric acid. In specific embodiments, the amino acid substitution is at position 48. In some of these embodiments, the lysine at position 48 is substituted by an arginine. In specific embodiments, the amino acid substitution is at position 49. In some of these embodiments, the leucine at position 49 is substituted by a lysine. In specific embodiments, the amino acid substitution is at position 50. In some of these embodiments, the arginine at position 50 is substituted by a lysine. In specific embodiments, the amino acid substitution is at position 53. In some of these embodiments, the tyrosine at position 53 is substituted by a leucine. In specific embodiments, the amino acid substitution is at position 54. In some of these embodiments, the serine at position 54 is substituted by a glutamic acid. In some of these embodiments, the serine at position 54 is substituted by a lysine. In some of these embodiments, the serine at position 54 is substituted by an aspartic acid. In specific embodiments, the amino acid substitution is at position 55. In some of these embodiments, the lysine at position 55 is substituted by an arginine. In specific embodiments, the amino acid substitution is at position 56. In some of these embodiments, the serine at position 56 is substituted by a phenylalanine. In some of these embodiments, the serine at position 56 is substituted by a lysine. In some of these embodiments, the serine at position 56 is substituted by an alanine. In some of these embodiments, the serine at position 56 is substituted by an aminoisobutyric acid. In specific embodiments, the amino acid substitution is at position 57. In some of these embodiments, the threonine at position 57 is substituted by a phenylalanine. In specific embodiments, the variant of helix 2 of apoC-II comprises three amino acid substitutions, wherein the amino acid substitutions are at position 46, position 54, and position 56. In some of these embodiments, the aspartic acid at position 46 is substituted by a phenylalanine, the serine at position 54 is substituted by a glutamic acid, and the serine at position 56 is substituted by a phenylalanine.

In some embodiments, the variant of helix 2 of apoC-II comprises at least one chemical modification. In certain embodiments, the chemical modification is a covalent linkage of a fatty acid. In various embodiments, the fatty acid comprises 4 to 26 carbons. In specific embodiments, the fatty acid comprises 10 carbons. In specific embodiments, the fatty acid comprises 12 carbons. In specific embodiments, the fatty acid comprises 14 carbons. In specific embodiments, the fatty acid comprises 16 carbons. In specific embodiments, the fatty acid comprises 18 carbons. In specific embodiments, the fatty acid comprises 20 carbons. In some embodiments, the fatty acid is saturated. In some other embodiments, the fatty acid is unsaturated. In certain embodiments, the fatty acid is linked to the N-terminal amino acid. In certain embodiments, the fatty acid is linked to an amino acid side group. In certain embodiments, the fatty acid is linked to the ε-amine of a lysine residue.

In some embodiments, the hinge region of the isolated apoC-II mimetic peptide comprises 5-10 amino acids. In certain embodiments, the hinge region comprises 7 amino acids. In specific embodiments, the hinge region comprises a proline. In some of these embodiments, the hinge region comprises a proline at position 58. In specific embodiments, the hinge region comprises an alanine. In some of these embodiments, the hinge region comprises an alanine at position 58. In specific embodiments, the hinge region comprises a norleucine. In some of these embodiments, the hinge region comprises a norleucine at position 60. In specific embodiments, the hinge region comprises a lysine. In some of these embodiments, the hinge region comprises a lysine at position 60. In specific embodiments, the hinge region comprises a valine. In some of these embodiments, the hinge region comprises a valine at position 60. In specific embodiments, the hinge region comprises a leucine. In some of these embodiments, the hinge region comprises a leucine at position 60. In specific embodiments, the hinge region comprises a methionine. In some of these embodiments, the hinge region comprises a methionine at position 60.

In some embodiments, the hinge region comprises at least one chemical modification. In certain embodiments, the chemical modification is a covalent linkage of a fatty acid. In various embodiments, the fatty acid comprises 4 to 26 carbons. In specific embodiments, the fatty acid comprises 10 carbons. In specific embodiments, the fatty acid comprises 12 carbons. In specific embodiments, the fatty acid comprises 14 carbons. In specific embodiments, the fatty acid comprises 16 carbons. In specific embodiments, the fatty acid comprises 18 carbons. In specific embodiments, the fatty acid comprises 20 carbons. In some embodiments, the fatty acid is saturated. In some other embodiments, the fatty acid is unsaturated. In certain embodiments, the fatty acid is linked to an amino acid side group. In certain embodiments, the fatty acid is linked to the ε-amine of a lysine residue.

In various embodiments, the hinge region allows the first helical domain and the second helical domain to retain a nearly straight conformation, wherein the second domain bends away from the first domain over an angle of no more than about 20°.

In some embodiments, the second domain of the isolated apoC-II mimetic peptide is native helix 3 of apoC-II. In some other embodiments, the second domain of the isolated apoC-II mimetic peptide is a variant of helix 3 of apoC-II.

In some embodiments, the variant of helix 3 of apoC-II comprises elongation of helix 3 of apoC-II. In various embodiments, the helix 3 of apoC-II is elongated by 1-10 amino acids at the C-terminus. In certain embodiments, the helix 3 of apoC-II is elongated by 4 amino acids at the C-terminus. In specific embodiments, the helix 3 of apoC-II is elongated by amino acids lysine, glycine, glutamic acid, and glutamic acid from N-terminus to C-terminus (SEQ ID NO: 75).

In some embodiments, the variant of helix 3 of apoC-II comprises at least one mutation of helix 3 of apoC-II. In some of these embodiments, the mutation is an amino acid substitution. In certain embodiments, an original amino acid of helix 3 of apoC-II is substituted by a natural amino acid. In certain embodiments, an original amino acid of helix 3 of apoC-II is substituted by an unnatural amino acid. In certain embodiments, an original amino acid of helix 3 of apoC-II is substituted by an amino acid analog. In specific embodiments, the amino acid substitution is at position 70. In some of these embodiments, the glutamine at position 70 is substituted by an arginine. In some of these embodiments, the glutamine at position 70 is substituted by a lysine.

In some embodiments, the variant of helix 3 of apoC-II comprises at least one chemical modification. In certain embodiments, the chemical modification is a covalent linkage of a fatty acid. In various embodiments, the fatty acid comprises 4 to 26 carbons. In specific embodiments, the fatty acid comprises 10 carbons. In specific embodiments, the fatty acid comprises 12 carbons. In specific embodiments, the fatty acid comprises 14 carbons. In specific embodiments, the fatty acid comprises 16 carbons. In specific embodiments, the fatty acid comprises 18 carbons. In specific embodiments, the fatty acid comprises 20 carbons. In some embodiments, the fatty acid is saturated. In some other embodiments, the fatty acid is unsaturated. In certain embodiments, the fatty acid is linked to the C-terminal amino acid. In certain embodiments, the fatty acid is linked to an amino acid side group. In certain embodiments, the fatty acid is linked to the ε-amine of a lysine residue. In certain embodiments, the C-terminal amino acid is modified by a C-terminal amide.

In various embodiments, the isolated apoC-II mimetic peptide further comprises a purification tag. In some of these embodiments, the purification tag is a polyhistidine-tag, a myc-tag, or an HA-tag.

In various embodiments, the first domain of the apoC-II mimetic peptide has an affinity for binding to lipoproteins. In various embodiments, the second domain is capable of activating lipoprotein lipase (LPL). In some embodiments, the peptide is capable of activating lipolysis by LPL. In some embodiments, the peptide is capable of displacing apoC-III in lipoproteins. In some embodiments, the peptide is capable of reducing triglyceride (TG) level in vivo. In some of these embodiments, the peptide is capable of reducing elevated TG level caused by LPL deficiency. In some of these embodiments, the peptide is capable of reducing elevated TG level caused by elevated apoC-III. In some of these embodiments, the peptide is capable of reducing elevated TG level caused by apoC-II deficiency. In some of these embodiments, the peptide is capable of reducing post-prandial elevated TG level.

In specific embodiments, the peptide has the sequence set forth in SEQ ID NO: 6.

In specific embodiments, the peptide has the sequence set forth in SEQ ID NO: 9.

In another aspect, provided herein is an isolated apoC-II mimetic peptide of no more than 30 amino acids, consisting of a variant of helix 3 of apoC-II.

In some embodiments, the variant of helix 3 of apoC-II comprises elongation of helix 3 of apoC-II In various embodiments, the helix 3 of apoC-II is elongated by 1-10 amino acids at the N-terminus. In certain embodiments, the helix 3 of apoC-II is elongated by 6 amino acids at the N-terminus. In specific embodiments, the variant of helix 3 of apoC-II comprises a lysine or methionine at position 60. In various embodiments, the helix 3 of apoC-II is elongated by 1-10 amino acids at the C-terminus. In certain embodiments, the helix 3 of apoC-II is elongated by 4 amino acids at the C-terminus. In specific embodiments, the helix 3 of apoC-II is elongated by amino acids lysine, glycine, glutamic acid, and glutamic acid from N-terminus to C-terminus (SEQ ID NO: 75).

In some embodiments, the variant of helix 3 of apoC-II comprises at least one mutation of helix 3 of apoC-II. In some of these embodiments, the mutation is an amino acid substitution. In certain embodiments, an original amino acid of helix 3 of apoC-II is substituted by a natural amino acid. In certain embodiments, an original amino acid of helix 3 of apoC-II is substituted by an unnatural amino acid. In certain embodiments, an original amino acid of helix 3 of apoC-II is substituted by an amino acid analog.

In some embodiments, the variant of helix 3 of apoC-II comprises at least one chemical modification. In certain embodiments, the chemical modification is a covalent linkage of a fatty acid. In various embodiments, the fatty acid comprises 4 to 26 carbons. In specific embodiments, the fatty acid comprises 10 carbons. In specific embodiments, the fatty acid comprises 12 carbons. In specific embodiments, the fatty acid comprises 14 carbons. In specific embodiments, the fatty acid comprises 16 carbons. In specific embodiments, the fatty acid comprises 18 carbons. In specific embodiments, the fatty acid comprises 20 carbons. In some embodiments, the fatty acid is saturated. In some other embodiments, the fatty acid is unsaturated. In certain embodiments, the fatty acid is linked to the N-terminal amino acid. In certain embodiments, the fatty acid is linked to the C-terminal amino acid. In certain embodiments, the fatty acid is linked to an amino acid side group. In certain embodiments, the fatty acid is linked to the ε-amine of a lysine residue.

In various embodiments, the isolated apoC-II mimetic peptide further comprises a purification tag. In some of these embodiments, the purification tag is a polyhistidine-tag, a myc-tag, or an HA-tag.

In various embodiments, the variant of helix 3 of apoC-III has an affinity for binding to lipoproteins. In various embodiments, the variant of helix 3 of apoC-II is capable of activating lipoprotein lipase (LPL). In some embodiments, the peptide is capable of activating lipolysis by LPL. In some embodiments, the peptide is capable of displacing apoC-III in lipoproteins. In some embodiments, the peptide is capable of reducing triglyceride (TG) level in vivo. In some of these embodiments, the peptide is capable of reducing elevated TG level caused by LPL deficiency. In some of these embodiments, the peptide is capable of reducing elevated TG level caused by elevated apoC-III. In some of these embodiments, the peptide is capable of reducing elevated TG level caused by apoC-II deficiency. In some of these embodiments, the peptide is capable of reducing post-prandial elevated TG level.

In another aspect, provided herein is a pharmaceutical composition comprising the apoC-III mimetic peptide and a pharmaceutically acceptable carrier. In some embodiments, the pharmaceutical composition is suitable for subcutaneous injection.

In another aspect, provided herein is a method of treating hypertriglyceridemia in a patient, comprising administering to the patient an effective amount of the apoC-II mimetic peptide or the pharmaceutical composition comprising the apoC-II mimetic peptide. In some embodiments, the hypertriglyceridemia is associated with obesity. In some embodiments, the hypertriglyceridemia is associated with diabetes mellitus. In some embodiments, the hypertriglyceridemia is associated with alcohol consumption. In some embodiments, the hypertriglyceridemia is associated with medication.

In some embodiments, the hypertriglyceridemia is caused by LPL deficiency. In certain embodiments, the hypertriglyceridemia is familial lipoprotein lipase deficiency. In some embodiments, the LPL deficiency is caused by a mutation the LPL gene. In certain embodiments, the mutation leads to reduced LPL enzyme activity. In certain embodiments, the mutation leads to absent LPL enzyme activity. In some embodiments, the LPL deficiency is diagnosed by the absence of LPL activity in serum of the patient. In some embodiments, the mutation is detected by DNA sequence analysis. In some embodiments, the hypertriglyceridemia is caused by apoC-II deficiency. In some embodiments, the hypertriglyceridemia is caused by elevated apoC-III.

In certain embodiments, the pre-treatment serum triglyceride (TG) concentration of the patient is between 150 mg/dL and 199 mg/dL. In certain embodiments, the pre-treatment serum triglyceride (TG) concentration of the patient is between 200 mg/dL to 499 mg/dL. In certain embodiments, the pre-treatment serum triglyceride (TG) concentration of the patient is between 500 mg/dL to 999 mg/dL. In certain embodiments, the pre-treatment serum triglyceride (TG) concentration of the patient is between 1000 mg/dL and 1999 mg/dL. In certain embodiments, the pre-treatment serum triglyceride (TG) concentration of the patient is equal to or higher than 2000 mg/dL.

In specific embodiments, the patient has developed or is at risk for acute pancreatitis. In specific embodiments, the patient has developed or is at risk for acute cardiovascular disease.

In another aspect, also provided herein is a method of making the apoC-II mimetic peptide, comprising producing the peptide recombinantly.

In yet another aspect, also provided herein is a method of making the apoC-II mimetic peptide, comprising producing the peptide by chemical synthesis.

BRIEF DESCRIPTION OF THE DRAWINGS

These and other features, aspects, and advantages of the present invention will become better understood with regard to the following description, and accompanying drawings, where:

FIG. 1 shows the homology of amino acid residues 40-58 of mature human apoC-II protein across various species (SEQ ID NOS 57-68, respectively, in order of appearance).

FIG. 5 shows examples of chemical modification of the variant Delta4' (SEQ ID NO: 73). Mono-acyl-Delta4' (SEQ ID NO: 73) includes a stearic acid modified N-terminus. Di-acyl-Delta4' (SEQ ID NO: 73) includes a stearic acid modified N-terminus and a stearic acid modified leucine residue at position 49.

FIG. 15A, FIG. 15B, FIG. 15C, and FIG. 15D show the percentage change of LPL activity in an in vitro LPL assay of exemplary apoC-II mimetic peptide Delta6 and its variants using hypertriglyceridemia patient sera as substrate. The triglyceride concentration of the patient sera in FIG. 15A, FIG. 15B, FIG. 15C, and FIG. 15D are 1084 mg/dL, 1224 mg/dL, 1442 mg/dL, and 1669 mg/dL respectively.

FIG. 29A and FIG. 29B show the dose-dependent displacement of apoC-III by apoC-II-a peptide analyzed by mass spectrometry (MALDI-TOF), with FIG. 29A showing that apoC-II-a selectively displaces apoC-III and apoC-I but not apoC-II, and FIG. 29B showing that the binding of apoC-II-a peptide to VLDL is approximately proportional to its concentration.

FIG. 36A, FIG. 36B, and FIG. 36C show the percentage change of serum TG level of apoC-II knockout mice after injection of apoC-II mimetic peptide Delta6PV, with FIG. 36A showing the timeline of injection, FIG. 36B showing the percentage change of serum TG level after intraperitoneal injection of Delta6PV, and FIG. 36C showing the percentage change of serum TG level after subcutaneous injection of the Delta6PV. Saline was used as control. SM represents the conditions where Delta6PV was mixed with sphingomyelin (SM), a component of cell membrane.

FIG. 52 represents the results of in vitro LPL assay of apoC-II mimetic peptides Delta6PV, Delta6-T18F-PV, Delta6-T18F-PV-AIB7, 17 and Delta13-31-PV using apoC-II deficient patient sera as substrate.

FIG. 54A, FIG. 54B, and FIG. 54C present helical wheel and net plots of the apoC II mimetic peptide, apoC-II-a. FIG. 54A is a helical wheel plot of the 18A helix (SEQ ID NO: 77). The size of balls indicate the degree of charge or hydrophobicity. FIG. 54B is a helical wheel plot of the third helix of apoC-II (SEQ ID NO: 76). FIG. 54C is a helical net plot of the apoC-II-a peptide. ApoC-II-a has the sequence of DWLKAFYDKVAEKLKEAFPAMSTYT-GIFTDQVLSVLKGEE (SEQ ID NO: 56). The central region indicates the position of the hydrophobic face.

DETAILED DESCRIPTION

Definitions

Figure 2A:
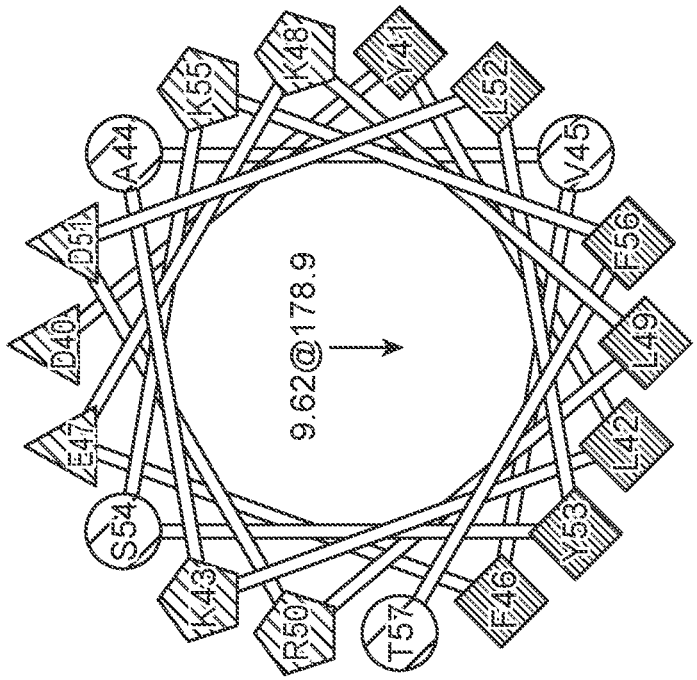
FIG. 2A and FIG. 2B present helical wheel plots of amino acid residues 40-57 of native apoC-II (SEQ ID NO: 69) and a variant Delta4' (SEQ ID NO: 70), with FIG. 2A representing the native apoC-II and FIG. 2B representing the variant, Delta4'. The shape and shade of the amino acid residue indicate the degree of charge and hydrophobicity. The first number in the center of the helical wheel indicates hydrophobic moment. The second number in the center of the helical wheel and the arrow indicate the angle of hydrophobic moment.

Unless defined otherwise, all technical and scientific terms used herein have the meaning commonly understood by one of ordinary skill in the art to which the invention pertains.

The term "amino acid" refers to natural amino acids, unnatural amino acids, and amino acid analogs. Unless otherwise indicated, the term "amino acid" includes both D and L stereoisomers if the respective structure allows such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids, or non-natural amino acid include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), Nalkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl) cysteine sulfoxide and S-(carboxymethyl)-cysteine sulfone.

As used herein, the term "peptide" refers a short polymer of amino acids linked together by peptide bonds. In contrast to other amino acid polymers (e.g., proteins, polypeptides, etc.), peptides are of about 75 amino acids or less in length. A peptide can comprise natural amino acids, non-natural amino acids, amino acid analogs, and/or modified amino acids. A peptide can be a subsequence of naturally occurring protein or a non-natural (synthetic) sequence.

As used herein, the term "mutant peptide" refers to a variant of a peptide having a distinct amino acid sequence from the most common variant occurring in nature, referred to as the "wild-type" sequence. A mutant peptide can comprise one or more amino acid substitution, deletion, or insertion as compared to the wild-type sequence. A mutant peptide can be a subsequence of a mutant protein or polypeptide (e.g., a subsequence of a naturally-occurring protein that is not the most common sequence in nature), or can be a peptide that is not a subsequence of a naturally occurring protein or polypeptide. For example, a "mutant apoC-II peptide" can be a subsequence of a mutant version of apoC-II or can be distinct sequence not found in naturally-occurring apoC-II proteins.

As used herein, the term "synthetic peptide" refers to a peptide having a distinct amino acid sequence from those found in natural peptides and/or proteins. A synthetic protein is not a subsequence of a naturally occurring protein, either the wild-type (i.e., most abundant) or mutant versions thereof. For example, a "synthetic apoC-II peptide" is not a subsequence of naturally occurring apoC-II. A "synthetic peptide," as used herein, can be produced or synthesized by any suitable method (e.g., recombinant expression, chemical synthesis, enzymatic synthesis, etc.).

The terms "peptide mimetic" or "peptidomimetic" refer to a peptide-like molecule that emulates a sequence derived from a protein or peptide. A peptide mimetic or peptidomimetic can contain amino acids and/or non-amino acid components. Examples of peptidomimetics include chemically modified peptides, peptoids (side groups are appended to the nitrogen atom of the peptide backbone, rather than to the α-carbons), β-peptides (amino group bonded to the β carbon rather than the α-carbon), etc. Chemical modification includes one or more modifications at amino acid side groups, α-carbon atoms, terminal amine group, or terminal carboxy group. A chemical modification can be adding chemical moieties, creating new bonds, or removing chemical moieties. Modifications at amino acid side groups include, without limitation, acylation of lysine ε-amino groups, N-alkylation of arginine, histidine, or lysine, alkylation of glutamic or aspartic carboxylic acid groups, lactam formation via cyclization of lysine ε-amino groups with glutamic or aspartic acid side group carboxyl groups, hydrocarbon "stapling" (e.g., to stabilize alpha-helix conformations), and deamidation of glutamine or asparagine. Modifications of the terminal amine group include, without limitation, the desamino, N-lower alkyl, N-di-lower alkyl, constrained alkyls (e.g. branched, cyclic, fused, adamantyl) and N-acyl modifications. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, can be protected by protective groups known to the ordinarily skilled peptide chemist. The α-carbon of an amino acid can be mono- or dimethylated.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues can be divided into classes based on common side group properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution can also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein include natural amino acids, non-natural amino acids, and amino acid analogs. For example, nor-leucine can be used to substitute methionine.

Non-conservative substitutions can involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "grouped residues" refers to a set of amino acids within a peptide, polypeptide, or protein that are physically positioned together in three dimensional space. The grouped residues may or may not be sequential in the primary sequence of the peptide, polypeptide, or protein. The residues can be grouped in a globular domain, can be present on the same surface, or can be presented on the same end or side of a secondary structure (e.g., alpha helix) or tertiary structure within a peptide, polypeptide, or protein. In some embodiments, in addition to being physically positioned together, the grouped residues also exhibit some degree of similarity in residue characteristics (e.g., size, polarity charge, etc.).

As used herein, "hydrophobic moment ($\mu_H$)" refers to a measure of the amphipathicity of a helix. The degree of amphipathicity (i.e., degree of asymmetry of hydrophobicity) in the multi-domain peptides or peptide analogs can be quantified by calculating the hydrophobic moment ($\mu_H$) of each of the amphipathic α-helical domains. Methods for calculating $\mu_H$ for a particular peptide sequence are well-known in the art, and are described, for example in Eisenberg et al., *Faraday Symp. Chem. Soc.* 17: 109-120, 1982; Eisenberg et al., *PNAS* 81:140-144, 1984; and Eisenberg et al., *J. Mal. Biol.* 179:125-142, 1984. The actual $\mu_H$ obtained for a particular peptide sequence will depend on the total number of amino acid residues composing the peptide. The amphipathicities of peptides of different lengths can be directly compared by way of the mean hydrophobic moment. The mean hydrophobic moment per residue can be obtained by dividing $\mu_H$ by the number of residues in the peptide.

Unless otherwise specified, "apoC-II" (synonymously, "apoC2") refers to human apolipoprotein C-II. Residues are numbered herein according to their position in the mature 79 amino acid form of human apoC-II protein following cleavage of the signal sequence. The mature apolipoprotein C-II protein is a 79 amino acid protein that includes three helices: helix 1, residues 17-38; helix 2, residues 45-57; and helix 3, residues 65-74/75 (Zdunek et al., *Biochemistry* 42: 1872-1889, 2003). The lipase-activating region of apoC-II has previously been localized to the C-terminal domain of the sequence, from about residue 56, whereas the N-terminal domain (residues 1-50) of the sequence is involved in lipid binding. Nucleic acid and protein sequences for apoC-II orthologues from a variety of species are publicly available. The GenBank NCBI accession number for the human apoC-II precursor is NP_000474. The amino acid sequences of mature human apoC-II, of amino acid residues 40-79 of human apoC-II, and of native helices 1-3 of human apoC-II are shown in Table 1 below.

As used herein, the term "effective amount" refers to the amount of a composition (e.g., a synthetic peptide) sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., synthetic peptide) to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal or lingual), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., multiple synthetic peptide or a synthetic peptide and another therapeutic agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used can vary. The appropriate dosage for co-administration can be readily determined by one skilled in the art. In some embodiments, when agents or therapies are coadministered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" means an approach to obtaining a beneficial or intended clinical result. The

TABLE 1

| Name | Sequence | SEQ ID NO |
|---|---|---|
| Native ApoC-II (full length) | TQQPQQDEMPSPTFLTQVKESLSSYWESAKTAAQN LYEKTYLPAVDEKLRDLYSKSTAAMSTYTGIFTDQ VLSVLKGEE | SEQ ID NO: 1 |
| Native ApoC-II (a.a.40-a.a.79) | TYLPAVDEKLRDLYSKSTAAMSTYTGIFTDQVLSVL KGEE | SEQ ID NO: 2 |
| Native ApoC-II (helix 1) | QVKESLSSYWESAKTAAQNLYE | SEQ ID NO: 3 |
| Native ApoC-II (helix 2) | VDEKLRDLYSKST | SEQ ID NO: 4 |
| Native ApoC-II (helix 3) | GIFTDQVLSVL | SEQ ID NO: 5 |

Unless otherwise specified, "LPL" refers to lipoprotein lipase. The GenBank NCBI accession number for human LPL protein is NP_000228.

As used herein, the term "subject" broadly refers to any animal, including but not limited to, human and non-human animals (e.g., dogs, cats, cows, horses, sheep, pigs, poultry, fish, crustaceans, etc.). As used herein, the term "patient" typically refers to a subject that is being treated for a disease or condition.

beneficial or intended clinical result can include alleviation of symptoms, a reduction in the severity of the disease, inhibiting an underlying cause of a disease or condition, steadying diseases in a non-advanced state, delaying the progress of a disease, and/or improvement or alleviation of disease conditions.

As used herein, the term "pharmaceutical composition" refers to the combination of an active agent (e.g., apoC-II mimetic peptide) with a carrier, inert or active, making the composition especially suitable for therapeutic or diagnostic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), glycerol, liquid polyethylene glycols, aprotic solvents such as dimethylsufoxide, N-methtylpyrrolidone and mixtures thereof, and various types of wetting agents, solubilizing agents, anti-oxidants, bulking agents, protein carriers such as albumins, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For examples of carriers, stabilizers and adjuvants, see, e.g., Martin, *Remington's Pharmaceutical Sciences*, 21th Ed., Mack Publ. Co., Easton, Pa. (2005), incorporated herein by reference in its entirety.

1.1. ApoC-II Mimetic Peptide

In a first aspect, disclosed herein is an isolated apoC-III mimetic peptide.

In some embodiments, the isolated apoC-III mimetic peptide is a multihelical peptide comprising a plurality of helical domains. In some multihelical embodiments, one or more of the helical domains are amphipathic and can bind to lipids and/or to the surface of lipoproteins. In certain embodiments, isolated the apoC-II mimetic peptide is a bihelical peptide comprising two helical domains. In some bihelical embodiments, at least one helical domain is amphipathic. In some bihelical embodiments, one helical domain is amphipathic, and the other helical domain is Type G helix found in globular proteins.

In some embodiments, the isolated apoC-III mimetic peptide is a single helical peptide. In some of these embodiments, the helical domain is amphipathic. In some other of these embodiments, the helical domain is Type G helix.

In various embodiments, the isolated apoC-III mimetic peptide is no more than 75 amino acids. In certain embodiments, the isolated apoC-III mimetic peptide is no more than 70 amino acids. In certain embodiments, the isolated apoC-III mimetic peptide is no more than 60 amino acids. In certain embodiments, the isolated apoC-III mimetic peptide is no more than 50 amino acids. In certain embodiments, the isolated apoC-III mimetic peptide is no more than 40 amino acids. In certain embodiments, the isolated apoC-III mimetic peptide is no more than 30 amino acids. In certain embodiments, the isolated apoC-III mimetic peptide is no more than 20 amino acids.

In typical embodiments, the isolated apoC-II mimetic peptide comprises a first helical domain, a hinge region, and a second helical domain.

In some embodiments, the isolated apoC-III mimetic peptide comprises a first helical domain, a hinge region, and a second helical domain in order from N-terminus to C-terminus. In some of these embodiments, the first helical domain is amphipathic. In some of these embodiments, the second helical domain forms a globular helix. In certain of these embodiments, the first helical domain is amphipathic and the second helical domain forms a globular helix.

In some embodiments, the first domain has an affinity for binding to lipoproteins. In some embodiments, the second domain is capable of activating lipoprotein lipase (LPL). In certain embodiments, the first domain has an affinity for binding to lipoproteins, and the second domain is capable of activating lipoprotein lipase (LPL).

In certain embodiments, the isolated apoC-II mimetic peptide is capable of activating lipolysis by LPL. In certain embodiments, the isolated apoC-II mimetic peptide is capable of displacing apoC-III from lipoproteins.

In various embodiments, the isolated apoC-II mimetic peptide is capable of reducing triglyceride (TG) level in vivo. In some of these embodiments, the peptide is capable of reducing elevated TG level caused by LPL deficiency. In some of these embodiments, the peptide is capable of reducing elevated TG level caused by elevated apoC-III. In some of these embodiments, the peptide is capable of reducing elevated TG level caused by apoC-II deficiency. In yet some of these embodiments, the peptide is capable of reducing post-prandial elevated TG level.

In various embodiments, the isolated apoC-II mimetic peptide has an amino acid sequence set forth in any one of SEQ ID NOs: 6-52 (Table 2). In some embodiments, the isolated apoC-II mimetic peptide has 90% sequence similarity to an amino acid sequence set forth in any one of SEQ ID NOs: 6-52. In some embodiments, the isolated apoC-II mimetic peptide has 91%, 92%, 93%, 94%, or 95% sequence similarity to an amino acid sequence set forth in any one of SEQ ID NOs: 6-52. In some embodiments, the isolated apoC-II mimetic peptide has 96%, 97%, 98% or 99% sequence similarity to an amino acid sequence set forth in any one of SEQ ID NOs: 6-52.

1.1.1. The First Helical Domain

In various embodiments, the first helical domain has an affinity for binding to lipoproteins. In some embodiments, the first helical domain is amphipathic. In certain of these embodiments, the helical domain has a hydrophobic moment score of about 6 to about 15, such as about 7 to about 15, about 8 to about 15, about 9 to about 15, about 10 to about 15, about 11 to about 15, about 12 to about 15, about 13 to about 15, about 14 to about 15, about 8 to about 14, about 9 to about 14, about 10 to about 14, about 11 to about 14, about 12 to about 14, about 13 to about 14, about 8 to about 13, about 9 to about 13, about 10 to about 13, about 11 to about 13, about 12 to about 13, about 8 to about 12, about 9 to about 12, about 10 to about 12, about 11 to about 12, about 8 to about 11, about 9 to about 11, about 10 to about 11, about 8 to about 10, about 9 to about 10, or about 8 to about 9. The hydrophobic moment of peptide can be calculated with online tools, such as rzlab.ucr.edu/scripts/wheel/wheel.cgi.

In some embodiments, the first helical domain of the isolated apoC-II mimetic peptide is native helix 1 of apoC-II protein. Helix 1 of apoC-II protein consists of amino acid residues 17-38 (SEQ ID NO: 3), numbered according to their position in the mature 79 amino acid apoC-II protein. In some other embodiments, the first helical domain of the isolated apoC-II mimetic peptide is a variant of helix 1 of apoC-II protein.

In some embodiments, the first helical domain of the isolated apoC-II mimetic peptide is native helix 2 of apoC-II protein. Helix 2 of apoC-II protein consists of amino acid residues 45-57 (SEQ ID NO: 4), numbered according to their position in the mature 79 amino acid apoC-II protein. In some other embodiments, the first helical domain of the isolated apoC-II mimetic peptide is a variant of helix 2 of apoC-II protein. In certain embodiments, the variant of helix 2 of apoC-II protein comprises at least one modification of the native helix 2 of apoC-II protein. In certain embodiments, the variant of helix 2 of apoC-II protein comprises a plurality of modifications of the native helix 2 of apoC-II protein. In various embodiments, each modification is independently selected from elongations, truncations, mutations, and/or chemical modifications.

In some other embodiments, the first helical domain of the isolated apoC-II mimetic peptide is a variant of an amphipathic helix found on apolipoproteins other than apoC-II, or from other proteins that can bind lipids.

1.1.1.1. Elongation of Helix 2 of ApoC-II

In certain embodiments, the variant of helix 2 of apoC-II comprises an elongation of helix 2 of apoC-II. In various embodiments, the elongation increases the amphipathicity of the variant of helix 2 of apoC-II compared to the native helix 2 of apoC-II. In some embodiments, the elongation increases the affinity of the variant of helix 2 of apoC-II for binding to lipoproteins.

In some embodiments, the helix 2 of apoC-II is elongated at the N-terminus. In various embodiments, the helix 2 of apoC-II is elongated by 1-20 amino acids at the N-terminus. In some of these embodiments, the helix 2 of apoC-II is elongated by 1-10 amino acids at the N-terminus. In certain embodiments, the helix 2 of apoC-II is elongated by 1 amino acid at the N-terminus. In certain embodiments, the helix 2 of apoC-II is elongated by 2 amino acids at the N-terminus. In certain embodiments, the helix 2 of apoC-II is elongated by 3 amino acids at the N-terminus. In certain embodiments, the helix 2 of apoC-II is elongated by 4 amino acids at the N-terminus. In certain embodiments, the helix 2 of apoC-II is elongated by 5 amino acids at the N-terminus. In certain embodiments, the helix 2 of apoC-II is elongated by 6 amino acids at the N-terminus. In certain embodiments, the helix 2 of apoC-II is elongated by 7 amino acids at the N-terminus. In certain embodiments, the helix 2 of apoC-II is elongated by 8 amino acids at the N-terminus. In certain embodiments, the helix 2 of apoC-II is elongated by 9 amino acids at the N-terminus. In certain embodiments, the helix 2 of apoC-II is elongated by 10 amino acids at the N-terminus.

In specific embodiments, when the helix 2 of apoC-II is elongated by 1 amino acid at the N-terminus, the elongating amino acid is aspartic acid.

In specific embodiments, when the helix 2 of apoC-II is elongated by 2 amino acids at the N-terminus, the elongating amino acids are lysine and alanine, from N-terminus to C-terminus.

In typical embodiments, the helix 2 of apoC-II is elongated by 5 amino acids at the N-terminus. In some embodiments, the helix 2 of apoC-II is elongated by the native upstream amino acid sequence of human apoC-II. In some embodiments, the helix 2 of apoC-II is elongated by a mutant of native upstream amino acid sequence of human apoC-II. In some embodiments, the amino acids are at positions 40 to 44, numbered according to their position in the mature 79 amino acid human apoC-II protein. In some embodiments, the variant of helix 2 of apoC-II comprises an aspartic acid at position 40. In some embodiments, the variant of helix 2 of apoC-II comprises a tyrosine or a tryptophan at position 41. In some embodiments, the variant of helix 2 of apoC-II comprises a leucine at position 42. In some embodiments, the variant of helix 2 of apoC-II comprises a lysine or an arginine at position 43. In some embodiments, the variant of helix 2 of apoC-II comprises an alanine or a glutamic acid at position 44.

In specific embodiments, when the helix 2 of apoC-II is elongated by 5 amino acids at the N-terminus, the variant of helix 2 of apoC-II comprises an aspartic acid at position 40, a tyrosine at position 41, a leucine at position 42, a lysine at position 43, and a glutamic acid at position 44 (SEQ ID NO: 74).

In specific embodiments, when the helix 2 of apoC-II is elongated by 5 amino acids at the N-terminus, the variant of helix 2 of apoC-II comprises an aspartic acid at position 40, a tyrosine at position 41, a leucine at position 42, a lysine at position 43, and an alanine at position 44 (SEQ ID NO: 78).

1.1.1.2. Truncation of Helix 2 of ApoC-II

In certain embodiments, the variant of helix 2 of apoC-II comprises a truncation of helix 2 of apoC-II. In various embodiments, the truncation increases the amphipathicity of the variant of helix 2 of apoC-II compared to the native helix 2 of apoC-II. In some embodiments, the truncation increases the affinity of the variant of helix 2 of apoC-II for binding to lipoproteins.

In some embodiments, the helix 2 of apoC-II is truncated at the N-terminus. In various embodiments, the helix 2 of apoC-II is truncated by 1-12 amino acids at the N-terminus. In certain embodiments, the helix 2 of apoC-II is truncated by 1 amino acid at the N-terminus. In certain embodiments, the helix 2 of apoC-II is truncated by 2 amino acids at the N-terminus. In certain embodiments, the helix 2 of apoC-II is truncated by 3 amino acids at the N-terminus. In certain embodiments, the helix 2 of apoC-II is truncated by 4 amino acids at the N-terminus. In certain embodiments, the helix 2 of apoC-II is truncated by 5 amino acids at the N-terminus. In certain embodiments, the helix 2 of apoC-II is truncated by 6 amino acids at the N-terminus. In certain embodiments, the helix 2 of apoC-II is truncated by 7 amino acids at the N-terminus. In certain embodiments, the helix 2 of apoC-II is truncated by 8 amino acids at the N-terminus. In certain embodiments, the helix 2 of apoC-II is truncated by 9 amino acids at the N-terminus. In certain embodiments, the helix 2 of apoC-II is truncated by 10 amino acids at the N-terminus. In certain embodiments, the helix 2 of apoC-II is truncated by 11 amino acids at the N-terminus. In certain embodiments, the helix 2 of apoC-II is truncated by 12 amino acids at the N-terminus.

In specific embodiments, when the helix 2 of apoC-II is truncated by 2 amino acids at the N-terminus, the amino acid residues 45-46 of native helix 2 of apoC-II are deleted.

In specific embodiments, when the helix 2 of apoC-II is truncated by 4 amino acids at the N-terminus, the amino acid residues 45-48 of native helix 2 of apoC-II are deleted.

In specific embodiments, when the helix 2 of apoC-II is truncated by 5 amino acids at the N-terminus, the amino acid residues 45-49 of native helix 2 of apoC-II are deleted.

In specific embodiments, when the helix 2 of apoC-II is truncated by 6 amino acids at the N-terminus, the amino acid residues 45-50 of native helix 2 of apoC-II are deleted.

In specific embodiments, when the helix 2 of apoC-II is truncated by 9 amino acids at the N-terminus, the amino acid residues 45-53 of native helix 2 of apoC-II are deleted.

1.1.1.3. Mutation of Helix 2 of ApoC-II

In certain embodiments, the variant of helix 2 of apoC-II comprises at least one mutation of helix 2 of apoC-II. In various embodiments, the mutation increases the amphipathicity of the variant of helix 2 of apoC-II compared to the native helix 2 of apoC-II. In some embodiments, the mutation increases the affinity of the variant of helix 2 of apoC-II for binding to lipoproteins.

In certain embodiments, the variant of helix 2 of apoC-II comprises one mutation of helix 2 of apoC-II. In certain embodiments, the variant of helix 2 of apoC-II comprises two mutations of helix 2 of apoC-II. In certain embodiments, the variant of helix 2 of apoC-II comprises three mutations of helix 2 of apoC-II. In certain embodiments, the variant of helix 2 of apoC-II comprises four mutations of helix 2 of apoC-II. In certain embodiments, the variant of helix 2 of apoC-II comprises five mutations of helix 2 of apoC-II. In certain embodiments, the variant of helix 2 of apoC-II comprises more than five mutations of helix 2 of apoC-II.

In some embodiments, the mutation is an amino acid substitution. In some embodiments, the mutation is an amino acid insertion. In some embodiments, the mutation is an amino acid deletion.

In some embodiments, an original amino acid of helix 2 of apoC-II is substituted by a natural amino acid. In some embodiments, an original amino acid of helix 2 of apoC-II is substituted by an unnatural amino acid. In some embodiments, an original amino acid of helix 2 of apoC-II is substituted by an amino acid analog. In some embodiments, an original amino acid of helix 2 of apoC-II is substituted by a chemically modified amino acid.

In various embodiments, the amino acid substitution is a conservative or semi-conservative substitution. In some embodiments, the amino acid substitution has minimal impact on the activity and/or structure of the resultant peptide. In certain embodiments, the amino acid substitution maintains the structure of the peptide backbone in the area of the substitution, for example, as a helical conformation. In certain embodiments, the amino acid substitution maintains the charge or hydrophobicity of the molecule at the target site. In certain embodiments, the amino acid substitution maintains the bulk of the amino acid side group.

In various embodiments, the amino acid substitution is a non-conservative substitution. In some embodiments, the amino acid substitution produces significant changes in the peptide property. In certain embodiments, a hydrophilic residue is substituted by a hydrophobic residue. In certain other embodiments, a hydrophobic residue is substituted by a hydrophilic residue. In certain embodiments, a cysteine or proline is substituted by another residue. In certain other embodiments, a non-cysteine or non-proline is substituted by a cysteine or proline. In certain embodiments, a residue having an electropositive side group is substituted by an electronegative residue. In certain other embodiments, a residue having an electronegative side group is substituted by an electropositive residue. In certain embodiments, a residue having a bulky side group is substituted by a residue not having a side group. In certain other embodiments, a residue not having a side group is substituted by a residue having a bulky side group.

In certain embodiments, the amino acid substitution is at position 45. In some embodiments, the valine at position 45 is substituted by a phenylalanine.

In certain embodiments, the amino acid substitution is at position 46. In some embodiments, the aspartic acid at position 46 is substituted by a phenylalanine. In some embodiments, the aspartic acid at position 46 is substituted by a lysine. In some embodiments, the aspartic acid at position 46 is substituted by an aminoisobutyric acid.

In certain embodiments, the amino acid substitution is at position 47.

In certain embodiments, the amino acid substitution is at position 48. In some embodiments, the lysine at position 48 is substituted by an arginine.

In certain embodiments, the amino acid substitution is at position 49. In some embodiments, the leucine at position 49 is substituted by a lysine. In some of these embodiments, the lysine is modified by fatty acid.

In certain embodiments, the amino acid substitution is at position 50. In some embodiments, the arginine at position 50 is substituted by a lysine.

In certain embodiments, the amino acid substitution is at position 51.

In certain embodiments, the amino acid substitution is at position 52.

In certain embodiments, the amino acid substitution is at position 53. In some embodiments, the tyrosine at position 53 is substituted by a leucine.

In certain embodiments, the amino acid substitution is at position 54. In some embodiments, the serine at position 54 is substituted by a glutamic acid. In some embodiments, the serine at position 54 is substituted by a lysine. In some embodiments, the serine at position 54 is substituted by an aspartic acid.

In certain embodiments, the amino acid substitution is at position 55. In some embodiments, the lysine at position 55 is substituted by an arginine.

In certain embodiments, the amino acid substitution is at position 56. In some embodiments, the serine at position 56 is substituted by a phenylalanine. In some embodiments, the serine at position 56 is substituted by a lysine. In some embodiments, the serine at position 56 is substituted by an alanine. In some embodiments, the serine at position 56 is substituted by an aminoisobutyric acid.

In certain embodiments, the amino acid substitution is at position 57. In some embodiments, the threonine at position 57 is substituted by a phenylalanine.

In specific embodiments, the variant of helix 2 of apoC-II comprises two amino acid substitutions, and the amino acid substitutions are at position 46 and position 56. In some of these embodiments, the aspartic acid at position 46 is substituted by a phenylalanine and the serine at position 56 is substituted by a phenylalanine.

In specific embodiments, the variant of helix 2 of apoC-II comprises three amino acid substitutions, and the amino acid substitutions are at position 46, position 54, and position 56. In some of these embodiments, the aspartic acid at position 46 is substituted by a phenylalanine, the serine at position 54 is substituted by a glutamic acid, and the serine at position 56 is substituted by a phenylalanine.

1.1.1.4. Chemical Modification of the Variant of Helix 2 of ApoC-II

In certain embodiments, the variant of helix 2 of apoC-II comprises at least one chemical modification. In various embodiments, the chemical modification increases the amphipathicity of the variant of helix 2 of apoC-II compared to the native helix 2 of apoC-II. In some embodiments, the chemical modification increases the affinity of the variant of helix 2 of apoC-II for binding to lipoproteins.

In some embodiments, the chemical modification is at the N-terminus of the first domain. In various embodiments, the amino-end of the N-terminus can be modified by conjugation with various functional groups. Neutralization of the terminal charge of synthetic peptide mimics of apolipoproteins has been shown to increase their lipid affinity (Yancey et al., *Biochem.* 34:7955-7965, 1995; Venkatachalapathi et al., Protein: Structure, *Function and Genetics* 15:349-359, 1993). For example, acetylation of the amino terminal end of amphipathic peptides increases the lipid affinity of the peptide (Mishra et al., *J. Biol. Chem.* 269:7185-7191, 1994). Other possible end modifications are described, for example, in Brouillette et al., *Biochem. Biophys. Acta* 1256: 103-129, 1995; Mishra et al., *J. Biol. Chem.* 269:7185-7191, 1994; and Mishra et al., *J. Biol. Chem.* 270:1602-1611, 1995.

In some embodiments, the chemical modification is at an amino acid side group of the first domain. Modifications at amino acid side groups include, without limitation, acylation of lysine ε-amino groups, N-alkylation of arginine, histidine, or lysine, alkylation of glutamic or aspartic carboxylic acid groups, lactam formation via cyclization of lysine ε-amino groups with glutamic or aspartic acid side group carboxyl groups, hydrocarbon "stapling" (e.g., to stabilize alpha-helix conformations), and deamidation of glutamine or asparagine. In some embodiments, the first domain is modified by replacement of one or more side groups with other side groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from a 5-membered ring to a 4-, 6-, or 7-membered ring. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl. Peptides, as well as peptide analogs and mimetics, can also be covalently bound to one or more of a variety of nonproteinaceous polymers, for example, polyethylene glycol, polypropylene glycol, or polyoxyalkenes, as described in U.S. Pat. Nos. 4,640,835; 4,496,689; 4,301,144; 4,670,417; 4,791,192; and 4,179,337.

In certain embodiments, the chemical modification is a non-covalent modification. In certain other embodiments, the chemical modification is covalently linked to the modified amino acid. In various embodiments, the chemical modification can be phosphorylation, glycosylation, or lipidation.

In some embodiments, the chemical modification is a covalent linkage of a fatty acid. In certain embodiments, the fatty acid is saturated. In certain other embodiments, the fatty acid is unsaturated.

In various embodiments, the fatty acid comprises 2 to 30 carbons, such as 4 to 26 carbons, 6 to 24 carbons, 10 to 20 carbons, 12 to 18 carbons, and 14 to 16 carbons. In certain embodiments, the fatty acid comprises 6 carbons. In certain embodiments, the fatty acid comprises 7 carbons. In certain embodiments, the fatty acid comprises 8 carbons. In certain embodiments, the fatty acid comprises 9 carbons. In certain embodiments, the fatty acid comprises 10 carbons. In certain embodiments, the fatty acid comprises 11 carbons. In certain embodiments, the fatty acid comprises 12 carbons. In certain embodiments, the fatty acid comprises 13 carbons. In certain embodiments, the fatty acid comprises 14 carbons. In certain embodiments, the fatty acid comprises 15 carbons. In certain embodiments, the fatty acid comprises 16 carbons. In certain embodiments, the fatty acid comprises 17 carbons. In certain embodiments, the fatty acid comprises 18 carbons. In certain embodiments, the fatty acid comprises 19 carbons. In certain embodiments, the fatty acid comprises 20 carbons. In certain embodiments, the fatty acid comprises 21 carbons. In certain embodiments, the fatty acid comprises 22 carbons. In certain embodiments, the fatty acid comprises 23 carbons. In certain embodiments, the fatty acid comprises 24 carbons.

In some embodiments, the unsaturated fatty acid has 1, 2, 3, 4, 5, or 6 double bonds. In certain embodiments, the unsaturated fatty acid is arachidonic acid. In certain embodiments, the unsaturated fatty acid is linoleic acid. In certain embodiments, the unsaturated fatty acid is oleic acid. In certain embodiments, the unsaturated fatty acid is palmitoleic acid. In certain embodiments, the unsaturated fatty acid is linolenic acid. In certain embodiments, the unsaturated fatty acid is eicosapentaenoic acid. In certain embodiments, the unsaturated fatty acid is docosahexaenoic acid.

In specific embodiments, the fatty acid is palmitic acid. In specific embodiments, the fatty acid is stearic acid.

In certain embodiments, the isolated apoC-III mimetic peptide comprises a stearic acid covalently linked to the N-terminal amino acid. In some of these embodiments, the N-terminal amino acid is aspartic acid.

In certain embodiments, the isolated apoC-II mimetic peptide comprises a stearic acid covalently linked to the side group of a lysine residue. In specific embodiments, when the isolated apoC-III mimetic peptide comprises a lysine at position 46, the stearic acid is covalently linked to the lysine residue at position 46. In specific embodiments, when the isolated apoC-III mimetic peptide comprises a lysine at position 49, the stearic acid is covalently linked to the lysine residue at position 49. In specific embodiments, when the isolated apoC-III mimetic peptide comprises a lysine at position 56, the stearic acid is covalently linked to the lysine residue at position 56.

1.1.2. The Hinge Region

In some embodiments, the isolated apoC-III mimetic peptide comprises a hinge region connecting the first helical domain and the second helical domain. In certain embodiments, the hinge region functionally separates the first helical domain and the second helical domain. In various embodiments, the hinge region helps the second domain, which has the LPL activation activity, to attach itself to the micelle surface of lipoprotein. In certain embodiments, the hinge region allows the first helical domain and the second helical domain to retain a nearly straight conformation, wherein the second domain bends away from the first domain over an angle of no more than about 20°, such as no more than about 15°, no more than about 10°, or no more than about 5°.

1.1.2.1. Amino Acid Composition of the Hinge Region

In various embodiments, the hinge region comprises 3-15 amino acids, such as 4-12 amino acids, 5-10 amino acids, 6-9 amino acids, or 7-8 amino acids. In certain embodiments, the hinge region comprises 3 amino acids. In certain embodiments, the hinge region comprises 4 amino acids. In certain embodiments, the hinge region comprises 5 amino acids. In certain embodiments, the hinge region comprises 6 amino acids. In certain embodiments, the hinge region comprises 7 amino acids. In certain embodiments, the hinge region comprises 8 amino acids. In certain embodiments, the hinge region comprises 9 amino acids. In certain embodiments, the hinge region comprises 10 amino acids. In certain embodiments, the hinge region comprises 11 amino acids. In certain embodiments, the hinge region comprises 12 amino acids. In certain embodiments, the hinge region comprises 13 amino acids. In certain embodiments, the hinge region comprises 14 amino acids. In certain embodiments, the hinge region comprises 15 amino acids.

In some embodiments, the hinge region comprises a natural amino acid. In some embodiments, the hinge region comprises an unnatural amino acid. In some embodiments, the hinge region comprises an amino acid analog.

In various embodiments, the hinge region comprises a proline. In some embodiments, the hinge region comprises a hydroxyl proline. Other suitable amino acids (such as glycine, serine, threonine, and alanine) that functionally separate the two helical domains can also be used.

In some embodiments, the hinge region comprises a proline. In some of these embodiments, the hinge region comprises a proline at position 58. In certain embodiments, the hinge region comprises an alanine. In some of these embodiments, the hinge region comprises an alanine at position 58. In some of these embodiments, the hinge region comprises an alanine at position 59. In some embodiments, the hinge region comprises a norleucine. In some of these embodiments, the hinge region comprises a norleucine at position 60. In some embodiments, the hinge region comprises a lysine. In some of these embodiments, the hinge region comprises a lysine at position 60. In some embodiments, the hinge region comprises a methionine. In some of these embodiments, the hinge region comprises a methionine at position 60. In some embodiments, the hinge region comprises a serine. In some of these embodiments, the hinge region comprises a serine at position 61. In some embodiments, the hinge region comprises a threonine. In some of these embodiments, the hinge region comprises a threonine at position 62. In some of these embodiments, the hinge region comprises a threonine at position 64. In some embodiments, the hinge region comprises a tyrosine. In some of these embodiments, the hinge region comprises a tyrosine at position 63.

1.1.2.2. Chemical Modification of the Hinge Region

In certain embodiments, the hinge region comprises at least one chemical modification.

In some embodiments, the chemical modification is at an amino acid side group of the hinge region. Modifications at amino acid side groups include, without limitation, acylation of lysine ε-amino groups, N-alkylation of arginine, histidine, or lysine, alkylation of glutamic or aspartic carboxylic acid groups, lactam formation via cyclization of lysine C-amino groups with glutamic or aspartic acid side group carboxyl groups, hydrocarbon "stapling" (e.g., to stabilize alpha-helix conformations), and deamidation of glutamine or asparagine. In some embodiments, the hinge region is modified by replacement of one or more side groups with other side groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from a 5-membered ring to a 4-, 6-, or 7-membered ring. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl. Peptides, as well as peptide analogs and mimetics, can also be covalently bound to one or more of a variety of nonproteinaceous polymers, for example, polyethylene glycol, polypropylene glycol, or polyoxyalkenes, as described in U.S. Pat. Nos. 4,640,835; 4,496,689; 4,301,144; 4,670,417; 4,791,192; and 4,179,337.

In certain embodiments, the chemical modification is a non-covalent modification. In certain other embodiments, the chemical modification is covalently linked. In various embodiments, the chemical modification can be phosphorylation, glycosylation, or lipidation.

In some embodiments, the chemical modification is a covalent linkage of a fatty acid. In certain embodiments, the fatty acid is saturated. In certain other embodiments, the fatty acid is unsaturated.

In various embodiments, the fatty acid comprises 2 to 30 carbons, such as 4 to 26 carbons, 6 to 24 carbons, 10 to 20 carbons, 12 to 18 carbons, and 14 to 16 carbons. In certain embodiments, the fatty acid comprises 6 carbons. In certain embodiments, the fatty acid comprises 7 carbons. In certain embodiments, the fatty acid comprises 8 carbons. In certain embodiments, the fatty acid comprises 9 carbons. In certain embodiments, the fatty acid comprises 10 carbons. In certain embodiments, the fatty acid comprises 11 carbons. In certain embodiments, the fatty acid comprises 12 carbons. In certain embodiments, the fatty acid comprises 13 carbons. In certain embodiments, the fatty acid comprises 14 carbons. In certain embodiments, the fatty acid comprises 15 carbons. In certain embodiments, the fatty acid comprises 16 carbons. In certain embodiments, the fatty acid comprises 17 carbons. In certain embodiments, the fatty acid comprises 18 carbons. In certain embodiments, the fatty acid comprises 19 carbons. In certain embodiments, the fatty acid comprises 20 carbons. In certain embodiments, the fatty acid comprises 21 carbons. In certain embodiments, the fatty acid comprises 22 carbons. In certain embodiments, the fatty acid comprises 23 carbons. In certain embodiments, the fatty acid comprises 24 carbons.

In some embodiments, the unsaturated fatty acid has 1, 2, 3, 4, 5, or 6 double bonds. In certain embodiments, the unsaturated fatty acid is arachidonic acid. In certain embodiments, the unsaturated fatty acid is linoleic acid. In certain embodiments, the unsaturated fatty acid is oleic acid. In certain embodiments, the unsaturated fatty acid is palmitoleic acid. In certain embodiments, the unsaturated fatty acid is linolenic acid. In certain embodiments, the unsaturated fatty acid is eicosapentaenoic acid. In certain embodiments, the unsaturated fatty acid is docosahexaenoic acid.

In specific embodiments, the fatty acid is palmitic acid. In specific embodiments, the fatty acid is stearic acid.

In certain embodiments, the isolated apoC-II mimetic peptide comprises a palmitic acid covalently linked to the side group of the lysine residue. In specific embodiments, when the isolated apoC-II mimetic peptide comprises a lysine at position 60, the palmitic acid is covalently linked to the lysine residue at position 60.

1.1.3. The Second Helical Domain

In some embodiments, the second helical domain of the isolated apoC-II mimetic peptide is native helix 3 of apoC-II protein. Helix 3 of apoC-II protein consists of amino acid residues 65-74/75 (SEQ ID NO: 5), numbered according to their position in the mature 79 amino acid apoC-II protein. In some other embodiments, the second helical domain of the isolated apoC-II mimetic peptide is a variant of helix 3 of apoC-II protein.

In certain embodiments, the variant of helix 3 of apoC-II protein comprises modifications of the native helix 3 of apoC-II protein. In various embodiments, the modifications include elongations, truncations, mutations, and chemical modifications.

1.1.3.1. Elongation of Helix 3 of ApoC-II

In certain embodiments, the variant of helix 3 of apoC-II comprises elongation of helix 3 of apoC-II. In some embodiments, the elongation increases the ability of variant of helix 3 of apoC-II for activating lipolysis by LPL.

In some embodiments, the helix 3 of apoC-II is elongated at the C-terminus. In various embodiments, the helix 3 of apoC-II is elongated by 1-20 amino acids at the C-terminus. In some of these embodiments, the helix 3 of apoC-II is elongated by 1-10 amino acids at the C-terminus. In certain embodiments, the helix 3 of apoC-II is elongated by 1 amino acid at the C-terminus. In certain embodiments, the helix 3 of apoC-II is elongated by 2 amino acids at the C-terminus. In certain embodiments, the helix 3 of apoC-II is elongated by 3 amino acids at the C-terminus. In certain embodiments, the helix 3 of apoC-II is elongated by 4 amino acids at the C-terminus. In certain embodiments, the helix 3 of apoC-II is elongated by 5 amino acids at the C-terminus. In certain embodiments, the helix 3 of apoC-II is elongated by 6 amino acids at the C-terminus. In certain embodiments, the helix 3 of apoC-II is elongated by 7 amino acids at the C-terminus. In certain embodiments, the helix 3 of apoC-II is elongated by 8 amino acids at the C-terminus. In certain embodiments, the helix 3 of apoC-II is elongated by 9 amino acids at the C-terminus. In certain embodiments, the helix 3 of apoC-II is elongated by 10 amino acids at the C-terminus.

In specific embodiments, when the helix 3 of apoC-II is elongated by 4 amino acids at the C-terminus, the amino acids are lysine, glycine, glutamic acid, and glutamic acid from N-terminus to C-terminus (SEQ ID NO: 75).

In specific embodiments, when the helix 3 of apoC-II is elongated by 4 amino acids at the C-terminus, the amino acids are arginine, glycine, glutamic acid, and glutamic acid from N-terminus to C-terminus (SEQ ID NO: 79).

1.1.3.2. Mutation of Helix 3 of ApoC-II

In certain embodiments, the variant of helix 3 of apoC-II comprises at least one mutation of helix 3 of apoC-II. In some embodiments, the mutation increases the ability of variant of helix 3 of apoC-II for activating lipolysis by LPL.

In certain embodiments, the variant of helix 3 of apoC-II comprises one mutation of helix 3 of apoC-II. In certain embodiments, the variant of helix 3 of apoC-II comprises two mutations of helix 3 of apoC-II. In certain embodiments, the variant of helix 3 of apoC-II comprises three mutations of helix 3 of apoC-II. In certain embodiments, the variant of helix 3 of apoC-II comprises four mutations of helix 3 of apoC-II. In certain embodiments, the variant of helix 3 of apoC-II comprises five mutations of helix 3 of apoC-II. In certain embodiments, the variant of helix 3 of apoC-II comprises more than five mutations of helix 3 of apoC-II.

In some embodiments, the mutation is an amino acid substitution. In some embodiments, the mutation is an amino acid insertion. In some embodiments, the mutation is an amino acid deletion.

In some embodiments, an original amino acid of helix 3 of apoC-III is substituted by a natural amino acid. In some embodiments, an original amino acid of helix 3 of apoC-II is substituted by an unnatural amino acid. In some embodiments, an original amino acid of helix 3 of apoC-II is substituted by an amino acid analog.

In various embodiments, the amino acid substitution is a conservative or semi-conservative substitution. In some embodiments, the amino acid substitution has minimal impact on the activity and/or structure of the resultant peptide. In certain embodiments, the amino acid substitution maintains the structure of the peptide backbone in the area of the substitution, for example, as a helical conformation. In certain embodiments, the amino acid substitution maintains the charge or hydrophobicity of the molecule at the target site. In certain embodiments, the amino acid substitution maintains the bulk of the amino acid side group.

In various embodiments, the amino acid substitution is a non-conservative substitution. In some embodiments, the amino acid substitution produces significant changes in the peptide property. In certain embodiments, a hydrophilic residue is substituted by a hydrophobic residue. In certain other embodiments, a hydrophobic residue is substituted by a hydrophilic residue. In certain embodiments, a cysteine or proline is substituted by another residue. In certain other embodiments, a non-cysteine or non-proline is substituted by a cysteine or proline. In certain embodiments, a residue having an electropositive side group is substituted by an electronegative residue. In certain other embodiments, a residue having an electronegative side group is substituted by an electropositive residue. In certain embodiments, a residue having a bulky side group is substituted by a residue not having a side group. In certain other embodiments, a residue not having a side group is substituted by a residue having a bulky side group.

In certain embodiments, the amino acid substitution is at position 70. In some of these embodiments, the glutamine at position 70 is substituted by an arginine. In some other of these embodiments, the glutamine at position 70 is substituted by a lysine.

1.1.3.3. Chemical Modification of the Variant of Helix 3 of ApoC-II

In certain embodiments, the variant of helix 3 of apoC-II comprises at least one chemical modification. In some embodiments, the chemical modification increases the ability of the variant of helix 3 to activate lipolysis by LPL.

In some embodiments, the chemical modification is at the C-terminus of the second domain. In various embodiments, the carboxyl-end of the C-terminus can be modified by conjugation with various functional groups. Neutralization of the terminal charge of synthetic peptide mimics of apolipoproteins has been shown to increase their lipid affinity (Yancey et al., *Biochem.* 34:7955-7965, 1995; Venkatachalapathi et al., Protein: Structure, *Function and Genetics* 15:349-359, 1993). For example, acetylation of the amino terminal end of amphipathic peptides increases the lipid affinity of the peptide (Mishra et al., *J. Biol. Chem.* 269: 7185-7191, 1994). Other possible end modifications are described, for example, in Brouillette et al., *Biochem. Biophys. Acta* 1256: 103-129, 1995; Mishra et al., *J. Biol. Chem.* 269:7185-7191, 1994; and Mishra et al., *J. Biol. Chem.* 270:1602-1611, 1995.

In some embodiments, the chemical modification is at an amino acid side group of an amino acid in the second domain. Modifications at amino acid side groups include, without limitation, acylation of lysine ε-amino groups, N-alkylation of arginine, histidine, or lysine, alkylation of glutamic or aspartic carboxylic acid groups, lactam formation via cyclization of lysine ε-amino groups with glutamic or aspartic acid side group carboxyl groups, hydrocarbon "stapling" (e.g., to stabilize alpha-helix conformations), and deamidation of glutamine or asparagine. In some embodiments, the second domain is modified by replacement of one or more side groups with other side groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from a 5-membered ring to a 4-, 6-, or 7-membered ring. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl. Peptides, as well as peptide analogs and mimetics, can also be covalently bound to one or more of a variety of nonproteinaceous polymers, for example, polyethylene glycol, polypropylene glycol, or polyoxyalkenes, as described in U.S. Pat. Nos. 4,640,835; 4,496,689; 4,301,144; 4,670,417; 4,791,192; and 4,179,337.

In certain embodiments, the chemical modification is a non-covalent modification. In certain other embodiments, the chemical modification is covalently linked. In various embodiments, the chemical modification can be phosphorylation, glycosylation, or lipidation.

In some embodiments, the chemical modification is a covalent linkage of a fatty acid. In certain embodiments, the fatty acid is saturated. In certain other embodiments, the fatty acid is unsaturated.

In various embodiments, the fatty acid comprises 2 to 30 carbons, such as 4 to 26 carbons, 6 to 24 carbons, 10 to 20 carbons, 12 to 18 carbons, and 14 to 16 carbons. In certain embodiments, the fatty acid comprises 6 carbons. In certain embodiments, the fatty acid comprises 7 carbons. In certain embodiments, the fatty acid comprises 8 carbons. In certain embodiments, the fatty acid comprises 9 carbons. In certain embodiments, the fatty acid comprises 10 carbons. In certain embodiments, the fatty acid comprises 11 carbons. In certain embodiments, the fatty acid comprises 12 carbons. In certain embodiments, the fatty acid comprises 13 carbons. In certain embodiments, the fatty acid comprises 14 carbons. In certain embodiments, the fatty acid comprises 15 carbons. In certain embodiments, the fatty acid comprises 16 carbons. In certain embodiments, the fatty acid comprises 17 carbons. In certain embodiments, the fatty acid comprises 18 carbons. In certain embodiments, the fatty acid comprises 19 carbons. In certain embodiments, the fatty acid comprises 20 carbons. In certain embodiments, the fatty acid comprises 21 carbons. In certain embodiments, the fatty acid comprises 22 carbons. In certain embodiments, the fatty acid comprises 23 carbons. In certain embodiments, the fatty acid comprises 24 carbons.

In some embodiments, the unsaturated fatty acid has 1, 2, 3, 4, 5, or 6 double bonds. In certain embodiments, the unsaturated fatty acid is arachidonic acid. In certain embodiments, the unsaturated fatty acid is linoleic acid. In certain embodiments, the unsaturated fatty acid is oleic acid. In certain embodiments, the unsaturated fatty acid is palmitoleic acid. In certain embodiments, the unsaturated fatty acid is linolenic acid. In certain embodiments, the unsaturated fatty acid is eicosapentaenoic acid. In certain embodiments, the unsaturated fatty acid is docosahexaenoic acid.

In specific embodiments, the fatty acid is palmitic acid. In specific embodiments, the fatty acid is stearic acid.

In certain embodiments, the C-terminal amino acid is modified by a C-terminal amide. In some of these embodiments, the C-terminal amino acid is glutamic acid.

1.1.4. Single Domain ApoC-II Mimetic Peptide

In some embodiments, the apoC-II mimetic peptide consists of one helical domain. In some of these embodiments, the helical domain is amphipathic. In some other of these embodiments, the helical domain is a globular helix. In certain embodiments, the apoC-II mimetic peptide is native helix 3 of apoC-II protein. Helix 3 of apoC-II protein consists of amino acid residues 65-74/75 (SEQ ID NO: 5), numbered according to their position in the mature 79 amino acid apoC-II protein. In certain other embodiments, the apoC-II mimetic peptide is a variant of helix 3 of apoC-II.

In some embodiments, the variant of helix 3 of apoC-II is no more than 40 amino acids, such as no more than 30 amino acids, or no more than 20 amino acids. In some embodiments, the variant of helix 3 of apoC-II comprises modifications of the native helix 3 of apoC-II. In various embodiments, the modifications include elongations, truncations, mutations, and chemical modifications.

1.1.4.1. Elongation of Helix 3 of ApoC-II

In certain embodiments, the variant of helix 3 of apoC-II comprises elongation of helix 3 of apoC-II. In some embodiments, the elongation increases the affinity of the variant of helix 3 for binding to lipoproteins. In some embodiments, the elongation increases the ability of variant of helix 3 of apoC-II for activating lipolysis by LPL.

In some embodiments, the helix 3 of apoC-II is elongated at the N-terminus. In various embodiments, the helix 3 of apoC-II is elongated by 1-20 amino acids at the N-terminus. In some of these embodiments, the helix 3 of apoC-II is elongated by 1-10 amino acids at the N-terminus. In certain embodiments, the helix 3 of apoC-II is elongated by 1 amino acid at the N-terminus. In certain embodiments, the helix 3 of apoC-II is elongated by 2 amino acids at the N-terminus. In certain embodiments, the helix 3 of apoC-II is elongated by 3 amino acids at the N-terminus. In certain embodiments, the helix 3 of apoC-II is elongated by 4 amino acids at the N-terminus. In certain embodiments, the helix 3 of apoC-II is elongated by 5 amino acids at the N-terminus. In certain embodiments, the helix 3 of apoC-II is elongated by 6 amino acids at the N-terminus. In certain embodiments, the helix 3 of apoC-II is elongated by 7 amino acids at the N-terminus. In certain embodiments, the helix 3 of apoC-II is elongated by 8 amino acids at the N-terminus. In certain embodiments, the helix 3 of apoC-II is elongated by 9 amino acids at the N-terminus. In certain embodiments, the helix 3 of apoC-II is elongated by 10 amino acids at the N-terminus.

In some embodiments, the helix 3 of apoC-II is elongated at the C-terminus. In various embodiments, the helix 3 of apoC-II is elongated by 1-20 amino acids at the C-terminus. In some of these embodiments, the helix 3 of apoC-II is elongated by 1-10 amino acids at the C-terminus. In certain embodiments, the helix 3 of apoC-II is elongated by 1 amino acid at the C-terminus. In certain embodiments, the helix 3 of apoC-II is elongated by 2 amino acids at the C-terminus. In certain embodiments, the helix 3 of apoC-II is elongated by 3 amino acids at the C-terminus. In certain embodiments, the helix 3 of apoC-II is elongated by 4 amino acids at the C-terminus. In certain embodiments, the helix 3 of apoC-II is elongated by 5 amino acids at the C-terminus. In certain embodiments, the helix 3 of apoC-II is elongated by 6 amino acids at the C-terminus. In certain embodiments, the helix 3 of apoC-II is elongated by 7 amino acids at the C-terminus.

In certain embodiments, the helix 3 of apoC-II is elongated by 8 amino acids at the C-terminus. In certain embodiments, the helix 3 of apoC-II is elongated by 9 amino acids at the C-terminus. In certain embodiments, the helix 3 of apoC-II is elongated by 10 amino acids at the C-terminus.

In certain embodiments, the helix 3 of apoC-II is elongated at both the N-terminus and the C-terminus. In specific embodiments, the helix 3 of apoC-II is elongated at the N-terminus by 6 amino acids and at the C-terminus by 4 amino acids. In some of these embodiments, when the helix 3 of apoC-II is elongated by 4 amino acids at the C-terminus, the amino acids are arginine, glycine, glutamic acid, and glutamic acid from N-terminus to C-terminus (SEQ ID NO: 79). In some of these embodiments, when the helix 3 of apoC-II is elongated by 6 amino acids at the N-terminus, the amino acids are alanine, methionine, serine, threonine, tyrosine, and threonine from N-terminus to C-terminus (SEQ ID NO: 80). In some other of these embodiments, when the helix 3 of apoC-II is elongated by 6 amino acids at the N-terminus, the amino acids are alanine, lysine, serine, threonine, tyrosine, and threonine from N-terminus to C-terminus (SEQ ID NO: 81).

1.1.4.2. Mutation of Helix 3 of ApoC-II

In certain embodiments, the variant of helix 3 of apoC-II comprises at least one mutation of helix 3 of apoC-II. In some embodiments, the mutation increases the affinity of the variant of helix 3 for binding to lipoproteins. In some embodiments, the mutation increases the ability of variant of helix 3 of apoC-II for activating lipolysis by LPL.

In certain embodiments, the variant of helix 3 of apoC-II comprises one mutation of helix 3 of apoC-II. In certain embodiments, the variant of helix 3 of apoC-II comprises two mutations of helix 3 of apoC-II. In certain embodiments, the variant of helix 3 of apoC-II comprises three mutations of helix 3 of apoC-II. In certain embodiments, the variant of helix 3 of apoC-II comprises four mutations of helix 3 of apoC-II. In certain embodiments, the variant of helix 3 of apoC-II comprises five mutations of helix 3 of apoC-II. In certain embodiments, the variant of helix 3 of apoC-II comprises more than five mutations of helix 3 of apoC-II.

In some embodiments, the mutation is an amino acid substitution. In some embodiments, the mutation is an amino acid insertion. In some embodiments, the mutation is an amino acid deletion.

In some embodiments, an original amino acid of helix 3 of apoC-II is substituted by a natural amino acid. In some embodiments, an original amino acid of helix 3 of apoC-II is substituted by an unnatural amino acid. In some embodiments, an original amino acid of helix 3 of apoC-II is substituted by an amino acid analog.

In various embodiments, the amino acid substitution is a conservative or semi-conservative substitution. In some embodiments, the amino acid substitution has minimal impact on the activity and/or structure of the resultant peptide. In certain embodiments, the amino acid substitution maintains the structure of the peptide backbone in the area of the substitution, for example, as a helical conformation. In certain embodiments, the amino acid substitution maintains the charge or hydrophobicity of the molecule at the target site. In certain embodiments, the amino acid substitution maintains the bulk of the amino acid side group.

In various embodiments, the amino acid substitution is a non-conservative substitution. In some embodiments, the amino acid substitution produces significant changes in the peptide property. In certain embodiments, a hydrophilic residue is substituted by a hydrophobic residue. In certain other embodiments, a hydrophobic residue is substituted by a hydrophilic residue. In certain embodiments, a cysteine or proline is substituted by another residue. In certain other embodiments, a non-cysteine or non-proline is substituted by a cysteine or proline. In certain embodiments, a residue having an electropositive side group is substituted by an electronegative residue. In certain other embodiments, a residue having an electronegative side group is substituted by an electropositive residue. In certain embodiments, a residue having a bulky side group is substituted by a residue not having a side group. In certain other embodiments, a residue not having a side group is substituted by a residue having a bulky side group.

1.1.4.3. Chemical Modification of the Variant of Helix 3 of ApoC-II

In certain embodiments, the variant of helix 3 of apoC-II comprises at least one chemical modification. In some embodiments, the chemical modification increases the affinity of the variant of helix 3 for binding to lipoproteins. In some embodiments, the chemical modification increases the ability of the variant of helix 3 for activating lipolysis by LPL.

In some embodiments, the chemical modification is at the N-terminus of the variant of helix 3 of apoC-II. In some embodiments, the chemical modification is at the C-terminus of the variant of helix 3 of apoC-II. In various embodiments, the amino-end of the N-terminus and/or at the carboxyl-end of the C-terminus can be modified by conjugation with various functional groups. Neutralization of the terminal charge of synthetic peptide mimics of apolipoproteins has been shown to increase their lipid affinity (Yancey et al., *Biochem.* 34:7955-7965, 1995; Venkatachalapathi et al., Protein: Structure, *Function and Genetics* 15:349-359, 1993). For example, acetylation of the amino terminal end of amphipathic peptides increases the lipid affinity of the peptide (Mishra et al., *J. Biol. Chem.* 269:7185-7191, 1994). Other possible end modifications are described, for example, in Brouillette et al., *Biochem. Biophys. Acta* 1256: 103-129, 1995; Mishra et al., *J. Biol. Chem.* 269:7185-7191, 1994; and Mishra et al., *J. Biol. Chem.* 270:1602-1611, 1995.

In some embodiments, the chemical modification is at an amino acid side group of the variant of helix 3 of apoC-II. Modifications at amino acid side groups include, without limitation, acylation of lysine ε-amino groups, N-alkylation of arginine, histidine, or lysine, alkylation of glutamic or aspartic carboxylic acid groups, lactam formation via cyclization of lysine ε-amino groups with glutamic or aspartic acid side group carboxyl groups, hydrocarbon “stapling” (e.g., to stabilize alpha-helix conformations), and deamidation of glutamine or asparagine. In some embodiments, the variant of helix 3 of apoC-II is modified by replacement of one or more side groups with other side groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from a 5-membered ring to a 4-, 6-, or 7-membered ring. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl. Peptides, as well as peptide analogs and mimetics, can also be covalently bound to one or more of a variety of nonproteinaceous polymers, for example, polyethylene glycol, polypropylene glycol, or polyoxyalkenes, as described in U.S. Pat. Nos. 4,640,835; 4,496,689; 4,301,144; 4,670,417; 4,791,192; and 4,179,337.

In certain embodiments, the chemical modification is non-covalent modification. In certain other embodiments, the chemical modification is covalent linkage. In various embodiments, the chemical modification can be phosphorylation, glycosylation, or lipidation.

In some embodiments, the chemical modification is a covalent linkage of a fatty acid. In certain embodiments, the fatty acid is saturated. In certain other embodiments, the fatty acid is unsaturated.

In various embodiments, the fatty acid comprises 2 to 30 carbons, such as 4 to 26 carbons, 6 to 24 carbons, 10 to 20 carbons, 12 to 18 carbons, and 14 to 16 carbons. In certain embodiments, the fatty acid comprises 6 carbons. In certain embodiments, the fatty acid comprises 7 carbons. In certain embodiments, the fatty acid comprises 8 carbons. In certain embodiments, the fatty acid comprises 9 carbons. In certain embodiments, the fatty acid comprises 10 carbons. In certain embodiments, the fatty acid comprises 11 carbons. In certain embodiments, the fatty acid comprises 12 carbons. In certain embodiments, the fatty acid comprises 13 carbons. In certain embodiments, the fatty acid comprises 14 carbons. In certain embodiments, the fatty acid comprises 15 carbons. In certain embodiments, the fatty acid comprises 16 carbons. In certain embodiments, the fatty acid comprises 17 carbons. In certain embodiments, the fatty acid comprises 18 carbons. In certain embodiments, the fatty acid comprises 19 carbons. In certain embodiments, the fatty acid comprises 20 carbons. In certain embodiments, the fatty acid comprises 21 carbons. In certain embodiments, the fatty acid comprises 22 carbons. In certain embodiments, the fatty acid comprises 23 carbons. In certain embodiments, the fatty acid comprises 24 carbons.

In some embodiments, the unsaturated fatty acid has 1, 2, 3, 4, 5, or 6 double bonds. In certain embodiments, the unsaturated fatty acid is arachidonic acid. In certain embodiments, the unsaturated fatty acid is linoleic acid. In certain embodiments, the unsaturated fatty acid is oleic acid. In certain embodiments, the unsaturated fatty acid is palmitoleic acid. In certain embodiments, the unsaturated fatty acid is linolenic acid. In certain embodiments, the unsaturated fatty acid is eicosapentaenoic acid. In certain embodiments, the unsaturated fatty acid is docosahexaenoic acid.

In specific embodiments, the fatty acid is palmitic acid. In specific embodiments, the fatty acid is stearic acid.

In certain embodiments, the isolated apoC-III mimetic peptide comprises a stearic acid covalently linked to the N-terminal amino acid. In some of these embodiments, the N-terminal amino acid is alanine.

In certain embodiments, the isolated apoC-III mimetic peptide comprises a stearic acid covalently linked to the side group of the lysine residue. In specific embodiments, when the isolated apoC-III mimetic peptide comprises a lysine at position 60, the stearic acid is covalently linked to the lysine residue. In specific embodiments, when the isolated apoC-II mimetic peptide comprises a lysine at position 76, the stearic acid is covalently linked to the lysine residue.

1.1.5. Preparation of ApoC-II Mimetic Peptide

Also disclosed herein are methods for producing the isolated apoC-III mimetic peptide.

1.1.5.1. Recombinant Synthesis

In certain embodiments, the isolated apoC-III mimetic peptide is produced recombinantly, for example using bacterial, yeast, or eukaryotic expression systems.

For recombinant production, a polynucleotide sequence encoding the single or multi-domain peptide is inserted into an appropriate expression vehicle, that is, a vector which contains the necessary elements for the transcription and translation of the inserted coding sequence, or in the case of an RNA viral vector, the necessary elements for replication and translation. The expression vehicle is then transfected into a suitable target cell which will express the single or multi-domain peptide. Depending on the expression system used, the expressed peptide is then isolated by procedures well-established in the art. Methods for recombinant protein and peptide production are well known in the art.

To increase efficiency of production, the polynucleotide can be designed to encode multiple units of the single or multi-domain peptide separated by enzymatic cleavage sites. The resulting polypeptide can be cleaved (e.g., by treatment with the appropriate enzyme) in order to recover the peptide units. This can increase the yield of peptides driven by a single promoter. In some embodiments, a polycistronic polynucleotide can be designed so that a single mRNA is transcribed which encodes multiple peptides, each coding region operatively linked to a cap-independent translation control sequence, for example, an internal ribosome entry site (IRES). When used in appropriate viral expression systems, the translation of each peptide encoded by the mRNA is directed internally in the transcript, for example, by the IRES. Thus, the polycistronic construct directs the transcription of a single, large polycistronic mRNA which, in turn, directs the translation of multiple, individual peptides. This approach eliminates the production and enzymatic processing of polypeptides and can significantly increase yield of peptide driven by a single promoter.

A variety of host-expression vector systems can be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus (CaMV) or tobacco mosaic virus (TMV)) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, can be used in the expression vector. For example, when cloning in bacterial systems, inducible promoters such as pL of bacteriophage λ, plac, ptrp, ptac (ptrp-lac hybrid promoter) and the like can be used. When cloning in insect cell systems, promoters such as the baculovirus polyhedron promoter can be used. When cloning in plant cell systems, promoters derived from the genome of plant cells (e.g., heat shock promoters, the promoter for the small subunit of RUBISCO, the promoter for the chlorophyll a/b binding protein) or from plant viruses (e.g., the 35S RNA promoter of CaMV, the coat protein promoter of TMV) can be used. When cloning in mammalian cell systems, promoters derived from the genome of mammalian cells (e.g., metallothionein promoter) or from mammalian viruses (e.g., the adenovirus late promoter, the vaccinia virus 7.5 K promoter) can be used.

1.1.5.2. Chemical Synthesis

In certain other embodiments, the isolated apoC-II mimetic peptide is produced by chemical synthesis. In some embodiments, the peptide is produced using liquid phase peptide synthesis techniques. In some other embodiments, the peptide is produced using solid phase peptide synthesis techniques.

Peptides having either the D- or L-configuration can be synthesized by automated solid phase procedures well known in the art. Suitable syntheses can be performed by utilizing "Boc" or "Fmoc" procedures. Techniques and procedures for solid phase synthesis are well-known in the art. The single and multi-domain peptides can also be prepared by way of segment condensation, as described, for example, in Liu et al., *Tetrahedron Lett.* 37:933-936, 1996; Baca et al., *J. Am. Chem. Soc.* 117: 1881-1887, 1995; Tam et al., *Int. J. Peptide Protein Res.* 45:209-216, 1995; Schnolzer and Kent, *Science* 256:221-225, 1992; Liu and Tam, *J. Am. Chem. Soc.* 116:4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). This is particularly the case with glycine containing peptides. Other methods useful for synthesizing the single and multi-domain peptides of the disclosure are described in Nakagawa et al., *J. Am. Chem. Soc.* 107:7087-7092, 1985.

Additional exemplary techniques known to those of ordinary skill in the art of peptide and peptide analog synthesis are taught by Bodanszky, M. and Bodanszky, A., *The Practice of Peptide Synthesis*, Springer Verlag, New York, 1994; and by Jones, J., *Amino Acid and Peptide Synthesis*, 2nd ed., Oxford University Press, 2002. The Bodanszky and Jones references detail the parameters and techniques for activating and coupling amino acids and amino acid derivatives. Moreover, the references teach how to select, use and remove various useful functional and protecting groups.

Peptides having either the D- or L-configuration can also be purchased from commercial suppliers of synthetic peptides. Such suppliers include, for example, Advanced ChemTech (Louisville, Ky.), Applied Biosystems (Foster City, Calif.), Bachem (Torrance, Calif.), Anaspec (San Jose, Calif.), and Cell Essentials (Boston, Mass.).

1.1.6. Purification of ApoC-II Mimetic Peptide

The peptides or peptide analogs of the disclosure can be purified by many techniques well known in the art, such as reverse phase chromatography, high performance liquid chromatography, ion exchange chromatography, size exclusion chromatography, affinity chromatography, gel electrophoresis, and the like. The actual conditions used to purify a particular single or multi-domain peptide or peptide analog will depend, in part, on synthesis strategy and on factors such as net charge, hydrophobicity, hydrophilicity, and the like, and will be apparent to those of ordinary skill in the art.

In various embodiments, the isolated apoC-II mimetic peptide further comprises a purification tag. In some embodiments, the purification tag is a polyhistidine-tag, a myc-tag, or an HA-tag.

1.2. Pharmaceutical Composition

Also provided herein are pharmaceutical compositions comprising one or more isolated apoC-II mimetic peptides described herein and a pharmaceutically acceptable carrier.

Any carrier which can supply an active peptide (e.g., without destroying or damaging the peptide within the carrier) is a suitable carrier, and such carriers are well known in the art. The apoC-II mimetic peptide can be formulated, e.g., using any formulation currently used to formulate other therapeutic peptides, such as insulins, GLP-1 agonists, and all approved peptides disclosed in the THPdb database of FDA approved therapeutic peptides and proteins (crdd.osdd.net/raghava/thpdb/).

The apoC-II mimetic peptide based pharmaceutical composition can be in the form of a solid, semi-solid or liquid dosage form: such as powder, solution, elixir, syrup, suspension, cream, drops, paste and spray. As those skilled in the art can recognize, depending on the chosen route of administration the composition form is determined.

In some embodiments, compositions are formulated for administration by any suitable route, including but not limited to, orally (e.g., such as in the form of tablets, capsules, granules or powders), sublingually, bucally, parenterally (such as by subcutaneous, intravenous, intramuscular, intradermal, or intrasternal injection or infusion (e.g., as sterile injectable aqueous or non-aqueous solutions or suspensions, etc.)), nasally (including administration to the nasal membranes, such as by inhalation spray), topically (such as in the form of a cream or ointment), transdermally (such as by transdermal patch), rectally (such as in the form of suppositories), or by surgical implantation at a particular site, etc.

In certain embodiments, the pharmaceutical compositions are formulated to be suitable for subcutaneous injection.

1.3. Methods of Treatment

Also provided herein are methods for treating dyslipidemic and vascular disorders, including but not limited to hyperlipidemia, hyperlipoproteinemia, hypercholesterolemia, hypertriglyceridemia, HDL deficiency, coronary artery disease, atherosclerosis, thrombotic stroke, peripheral vascular disease, restenosis, acute coronary syndrome, and reperfusion myocardial injury.

In some embodiments, the methods comprise administering the peptide or the pharmaceutical composition as described herein to a patient with hypertriglyceridemia.

In some embodiments, the patient is at risk of developing hypertriglyceridemia.

In various embodiments, the patient has hypertriglyceridemia, based on fasting plasma or serum TG concentration above a certain level. In some embodiments, the patient has mild hypertriglyceridemia, defined as pre-treatment serum triglyceride (TG) concentration between 150 mg/dL and 199 mg/dL. In some embodiments, the patient has moderate hypertriglyceridemia, defined as pre-treatment serum triglyceride (TG) concentration between 200 mg/dL and 999 mg/dL, such as between 200 mg/dL to 499 mg/dL and between 500 mg/dL to 999 mg/dL. In some embodiments, the patient has severe hypertriglyceridemia, defined as pre-treatment serum triglyceride (TG) concentration between 1000 mg/dL and 1999 mg/dL. In some embodiments, the patient has very severe hypertriglyceridemia, defined as pre-treatment serum triglyceride (TG) concentration equal to or higher than 2000 mg/dL.

In some embodiments, the patient has above-normal LDL-c levels. In some other embodiments, the patient has below-normal levels of HDL-c.

In certain embodiments, the hypertriglyceridemia is caused by LPL deficiency. In some of these embodiments, the patient's hypertriglyceridemia is familial lipoprotein lipase deficiency.

In some embodiments, the LPL deficiency is caused by a gene mutation. In some of these embodiments, the gene mutation is detected by DNA sequence analysis. In various embodiments, the LPL deficiency is caused by a mutation in the LPL, APOC2, APOA5, GPIHBP1, or LMF1 gene.

In certain embodiments, the LPL deficiency is caused by a mutation is the LPL gene. In some of these embodiments, the mutation leads to reduced LPL enzyme activity. In some of these embodiments, the mutation leads to absent LPL enzyme activity.

In certain embodiments, the patient's hypertriglyceridemia is monogenic. In certain other embodiments, the patient's hypertriglyceridemia is polygenic. In certain embodiments, the mutations are present homozygous state. In certain embodiments, the mutations are present in heterozygous state.

In some embodiments, the LPL deficiency is diagnosed by the absence of LPL activity in serum of the patient.

In certain embodiments, the hypertriglyceridemia is caused by apoC-II deficiency. In certain embodiments, the hypertriglyceridemia is caused by elevated apoC-III.

In some embodiments, the patient has diabetes. In some embodiments, the patient has metabolic syndrome. In some of these embodiments, the metabolic syndrome is obesity. In some embodiments, the patient has pancreatitis. In some of these embodiments, the patient has acute pancreatitis. In some embodiments, the patient has steatosis or steatohepatitis. In some of these embodiments, the steatosis or steatohepatitis is alcohol-related. In some of these embodiments, the steatosis or steatohepatitis is non-alcoholic. In some embodiments, the patient has cardiovascular disease. In some of these embodiments, the patient has acute cardiovascular disease. In some embodiments, the patient has arthrosclerosis. In some embodiments, the patient has taken medication that can lead to hypertriglyceridemia.

In certain embodiments, the patient is an adult. In certain other embodiments, the patient is a child.

In various embodiments, the peptide or the pharmaceutical composition is administered in an amount, on a schedule, and for a duration sufficient to reduce blood triglyceride level of the patient. In some embodiments, the polypeptide is administered in an amount, on a schedule, and for a duration sufficient to decrease triglyceride levels by at least 5%, 10%, 15%, 20%, 25%, or more as compared to levels just prior to initiation of treatment. In certain embodiments, the polypeptide is administered in an amount, on a dosage schedule, and for a duration sufficient to decrease triglyceride levels by at least 30%, 35%, 40%, 45%, 50%, or more. In particular embodiments, the polypeptide is administered in an amount, on a schedule, and for a time sufficient to reduce triglyceride levels by at least 55%, 60%, 65%, 70%, or more.

The treatment can consist of a single dose or a plurality of doses over a period of time.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature.

Methods

LPL Assay

Preparation of LPL: frozen stock of 10 µL of 0.5 mg/mL bovine LPL was used and diluted 1:100 (10 µL+990 µL of PBS).

Preparation of 20% Intralipid: 2000 mg/dL TG Intralipid was used to prepare 3 mg/dL TG Intralipid by diluting 1.5 µL of the stock with 998.5 µL PBS, or by diluting the stock 1:10 first and then mixing 15 µL of the diluted stock with 985 µL PBS. When apoC-II deficient human serum was used as a substrate, a frozen 10 µL aliquot of 1711 mg/dL (TG) was diluted by adding 990 µL PBS (1:100 dilution).

Preparation of free fatty acid (NEFA) assay: NEFA reagents were purchased from Wako Diagnostics, Wako Life Sciences, Inc. Reagent A was prepared by mixing Coloring Reagent A with Solvent A (225 µL per well). Reagent B was prepared by mixing Coloring Reagent B with Solvent B (75 µL per well). 5 nmoL oleic acid standard was prepared by diluting 20 µL of 1 mM oleic acid stock (WAKO NEFA standard solution) with 180 µL of 0.2% BSA.

LPL activity assay: 10 µL of Intralipid, human plasma sample, or mouse plasma sample was added in each well using repeater pipette. 10 µL (or 15 µL in the wells with no LPL control) of PBS and 10 µL of 1% BSA was added in each well using repeater pipette. 10 µL of peptides were added to corresponding wells in vertical triplicates (lowest concentration is on a left, highest is on the right). The plate was spun down at 1000 RPM for 10 seconds to mix and to remove the solutions from the wall of each well. The plate was put on ice and 5 µL of LPL was added using repeater pipette. The plate was spun down again at 1000 RPM for 10 seconds. The plate was covered and put back on ice for an incubation of 30 min. The plate was then moved to 37° C. and incubated for 1 hour.

Free fatty acids (NEFA) assay: 45 µL of 5 nmoL standard and 0 nmoL control (0.2% BSA) were added to corresponding wells. 225 µL of reagent A was added in each well using the reagent tray and 12-channel pipette. The plate was incubated for 10 min before 75 µL of reagent B was added to each well using the reagent tray and 12-channel pipette. The plate was not covered due to the high volume. The absorbance at 550 nm and 660 nm was measured.

ApoC-III Displacement Study

VLDL or chylomicrons isolated from human plasma were incubated with an apoC-II mimetic peptide for 1 hour at 37° C. and washed 3 times with PBS using spin filter with 100 kDa cutoff membrane. Supernatants were brought to the original volume with PBS and loaded to 4-12% Bis-TRIS SDS PAGE gel. ApoC-I, apoC-II, apoC-III, and apoE bands were identified by their corresponding size.

Inhibition of ApoC-III Study

LPL assay was performed using Intralipid, high TG human plasma (1:50 dilution), or apoC-III transgenic mouse plasma (1:50 dilution). When Intralipid was used as a substrate, 25 or 50 µM recombinant ApoC-III was added as an inhibitor. When the high TG human plasma was used as a substrate, 25 or 50 µM recombinant ApoC-III was added as an inhibitor with or without pre-incubation at 37° C. for 1 hour. An apoC-II mimetic peptide was added at various concentrations.

In Vivo Study

C57Bl/6 mice (wild-type), apoC-II knockout (apoC-II KO) mice, and apoC-III transgenic mice were used for in vivo study. The C57Bl/6 mice (wild-type) were purchased from Taconic Biosciences Inc. The apoC-II KO mice were created as described in Sakurai et al., *J Pharmacol Exp Ther* 356:341-353, 2016. The apoC-III transgenic mice were generated by overexpressing human apoC-III in C57Bl/6 mice. See Qu et al., *J Lipid Res.* 48:1476-1487, 2007.

Mice were fasted overnight (approximately 12 hours) before the study and 6 hours during the study, the next day. The apoC-II mimetic peptides were synthetically produced and free of biological contamination (not available as FDA approved compounds/treatment). Peptides were produced and used in sterile conditions and filtered by 0.2 nm filter before injections in a single dose 1-10 µmol/kg body weight (B. W.) administered either subcutaneous injection (S.Q. or S.C.), intraperitoneal injection (I.P.) or intravenous injection (I.V.) (in a sterile, pharmaceutical grade PBS solution at a volume ≤200 µL) as described in Sakurai et al., *J Pharmacol Exp Ther* 356:341-353, 2016.

In Vivo Intralipid Study

In some experiments, each animal received 20% Intralipid (FDA approved, Fresenius Kabi, Uppsala, Sweden) in a single dose either by oral gavage (using special sterile single-use non-toxic animal feeding needles) in a dose 10-20 µL/gram body weight (B.W.) (Tuzcu et al. *Drug Chem Toxicol* 37: 261-267, 2014; Kusminski et al. *Nature Medicine* 18: 1539-1549, 2012), or by intraperitoneal injection in a single bolus of 0.1-1.0 mL (Mahadero et al. *American J Surgery* 164: 45-50, 1992), or by intragastric administration of a dietetic commercially-available liquid oil (food grade vegetable, corn, soy or olive oil) in a single dose 10-20 µL/gram body weight. These oils were a source of TG— when absorbed TG tends to be broken down within 3 h (peak in 30 min) (Kritchevsky *Nutritional Biochemistry* 6:172-178, 1995). Blood samples (20-30 µL) were obtained from the retro-orbital plexus at time points: −1 h, 0 h, 1 h, 3 h, 6 h and 24 h for measurements of lipids. Mice were returned to metabolic cages after the 6 h time point where the food was put back. Once the study was completed (after 24 hours from the fat administration), mice were euthanized and organs collected.

In some cases, mice were returned to regular cages and housed for another 2-3 weeks for a complete recovery, before being studied in another experiment. There was 1 control group that received a sterile pharmaceutical grade saline in place of peptide.

Figure 55:
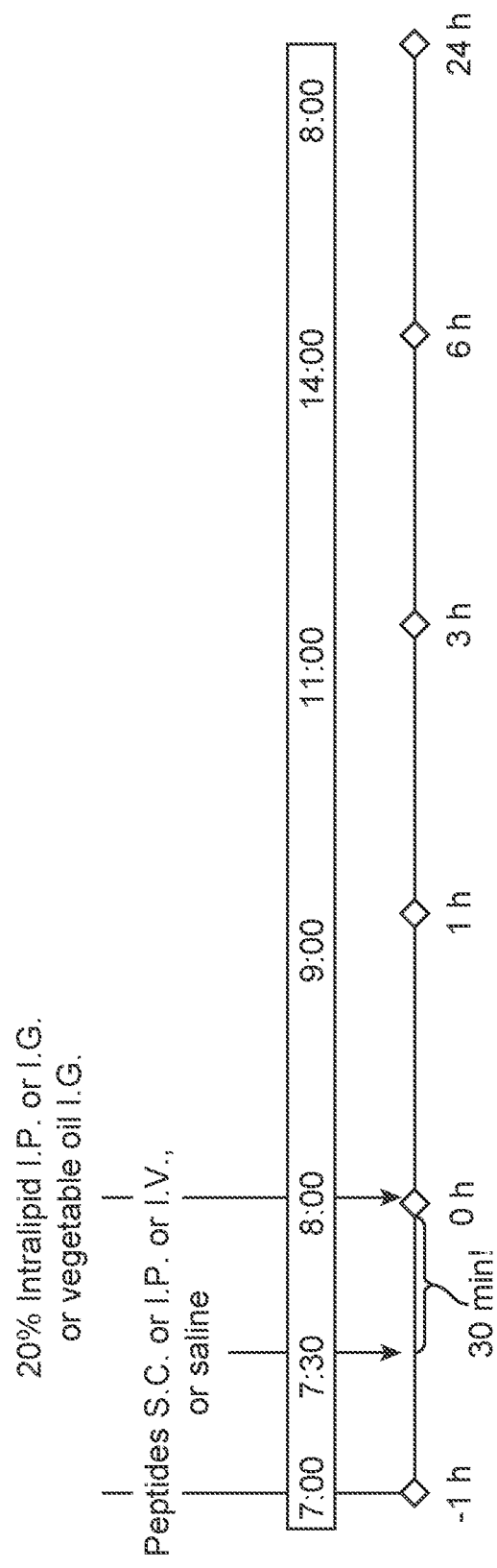
FIG. 55 shows the study design for testing post-prandial hypertriglyceridemia in mice.

The study design is presented on FIG. 55.

In Vivo Triton WR1339 Study

The ability of apolipoprotein mimetic peptides to normalize hypertriglyceridemia in mice treated with an LPL inhibitor, Tyloxapol, in presence of high TG provided by 20% Intralipid, was assessed.

Mice were fasted overnight (approximately 12 hours) before the study and 6 hours during the study, the next day. The apo mimetic peptides were synthetically produced and free of biological contamination (not available as FDA approved compounds/treatment). Peptides were produced and used in sterile conditions and filtered by 0.2 nm filter before injections in a single dose 1-5 µmol/kg B.W. either S.C. or I.P. or I.V. (in a sterile, pharmaceutical grade PBS solution at a volume ≤200 µL). Next, 10% Tyloxapol (Triton WR-1339, T-0307, Sigma-Aldrich) was injected I.V. in a single dose of 5 µL/gram B.W., as described earlier (Zhang Y. L. et al., *J Biol Chem.* 279: 19362-19374, 2004; Abe C. et al., *J. Nutr.* 137: 345-350, 2007). Tyloxapol is a nonionic detergent that inhibits LPL and hence clearance of triglycerides from the serum (Rasouli M. et al., *J Clin. Diagn. Research.* 10: BF01-BF05, 2016). Finally, each animal received 20% Intralipid (FDA approved, Fresenius Kabi, Uppsala, Sweden) in a single dose either by oral gavage (using special sterile single-use non-toxic animal feeding needles)—in a dose 10-20 µL/gram B.W. (Tuzcu K. et al., *Drug Chem Toxicol.*, 37: 261-267, 2014, Kusminski C. et al., *Nature Medicine.* 18: 1539-1549, 2012), or by intraperitoneal injection—in a single bolus of 0.1-1.0 mL (Mahadero G. et al., *American J Surgery.* 164: 45-50, 1992). Blood samples (20-30 µL) were obtained from the retro-orbital plexus at time points: −1 h, 0 h, 1 h, 3 h, 6 h and 24 h for measurements of lipids. Mice were returned to metabolic cages after the 6 h time point where the food was put back. Once the study was completed (after 24 hours from the Intralipid administration), mice were euthanized and organs collected.

In some cases, mice were returned to regular cages and housed for another 2-3 weeks for a complete recovery, before being studied in another experiment. There were 2 control groups, both receiving a sterile pharmaceutical grade saline in place of either peptide or Triton WR1339).

Figure 56:
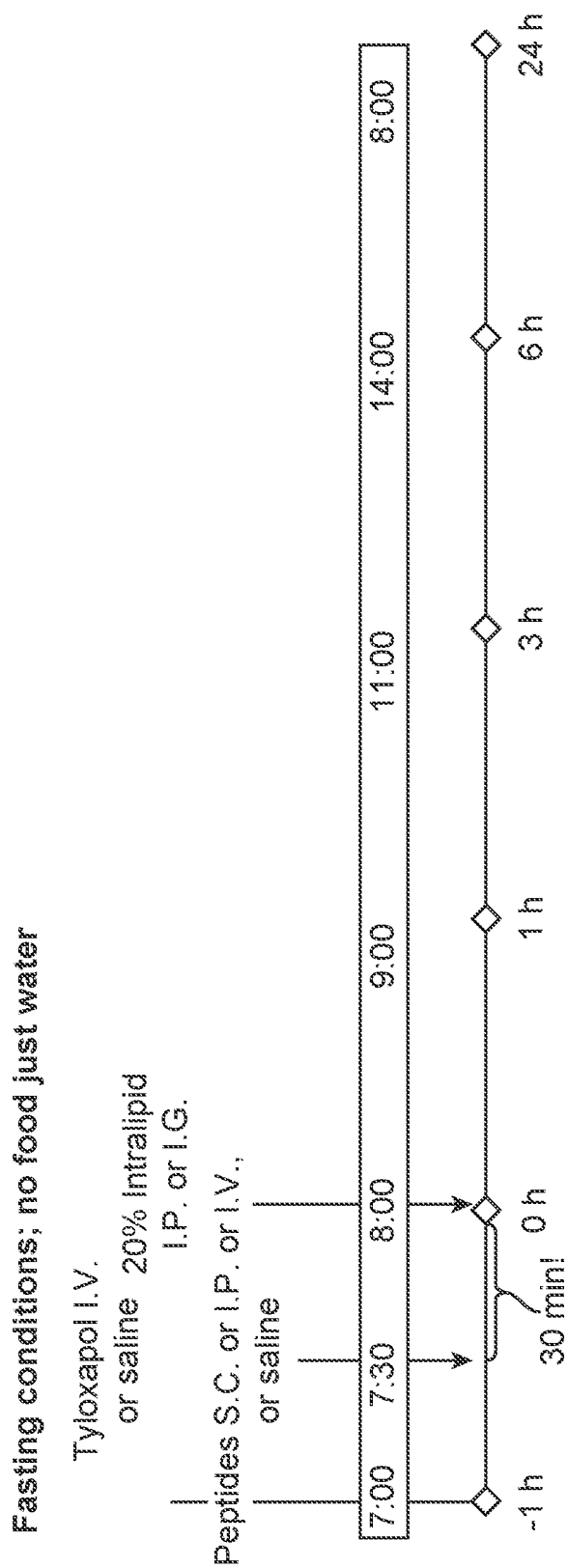
FIG. 56 shows the study design for testing post-prandial hypertriglyceridemia in mice in the presence of LPL inhibitor.

The study design is presented in FIG. 56.

In Vivo Studies in the Obese Monkey Model

Monkeys with a TG level greater than 2 mmol/L were selected, trained and assigned into 3 groups (control, 1 mg/kg Delta6PV, and 5 mg/kg Delta6PV). The desired dose was injected intravenously into the animals at 0 h time point. The monkeys were monitored over the course of 72 hours and blood samples at different time points were collected for biomarker analysis.

Example 1: Peptide Design

Apolipoprotein C-II (apoC-II) is a physiologic activator of lipoprotein lipase (LPL) and it can promote the hydrolysis of triglyceride in lipoproteins. A lack of functional apoC-II leads to severe hypertriglyceridemia, similar to what is seen for a genetic deficiency of LPL (Breckenridge et al., *N Engl J Med.* 298: 1265-1273, 1978).

The mature form of human apoC-II consists of 79 amino acid residues. The secondary structure of apoC-II has been determined by various measures, with residues 17-38 designated as helix 1, residues 45-57 designated as helix 2, and residues 65-74/75 designated as helix 3 (Zdunek et al., *Biochemistry* 42: 1872-1889, 2003). The C-terminal one-third of apoC-II, which is needed for activation of LPL, is more conserved between different species than the N-terminal two thirds of apoC-II, which is needed for lipid binding (Shen et al., *Gene* 254:189-198, 2000). The homology of amino acid residues 40-58 of mature human apoC-II protein across various species is shown on FIG. 1.

In order to make a clinically useful LPL activating peptide, we designed single helical and bihelical apoC-II mimetic peptides. We introduced various modifications, such as elongations, truncations, mutations, and chemical modifications to the helices of native human apoC-II protein.

Figure 2B:
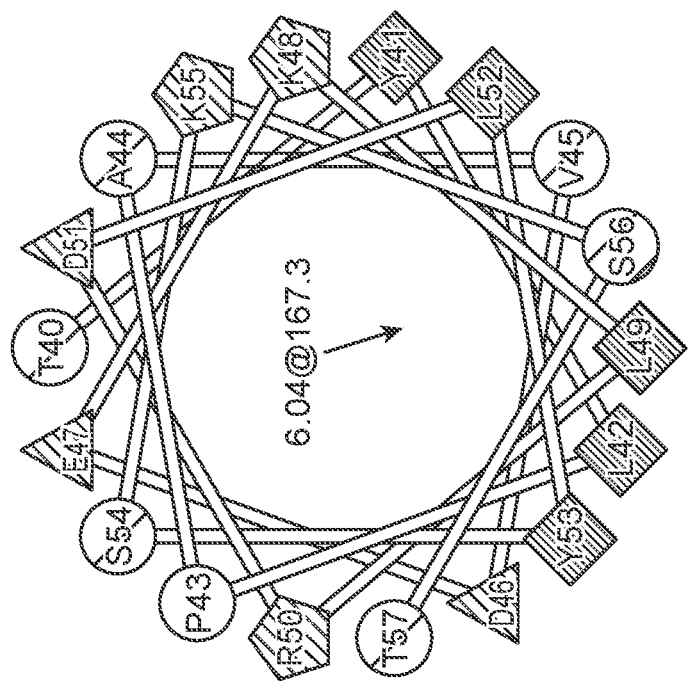
Figure 3A:
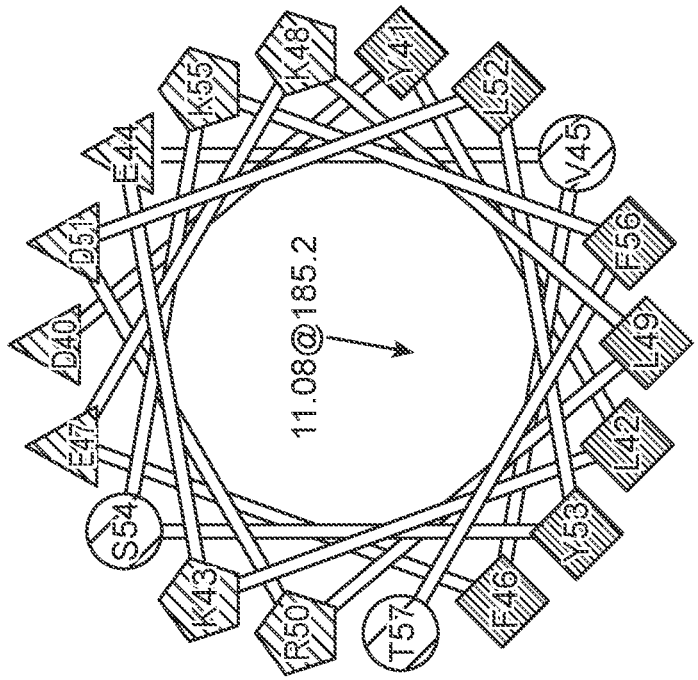
FIG. 3A and FIG. 3B present helical wheel plots of amino acid residues 40-57 of native apoC-II (SEQ ID NO: 69) and a variant Delta5' (SEQ ID NO: 71), with FIG. 3A representing the native apoC-II and FIG. 3B representing the variant, Delta5'.
Figure 3B:
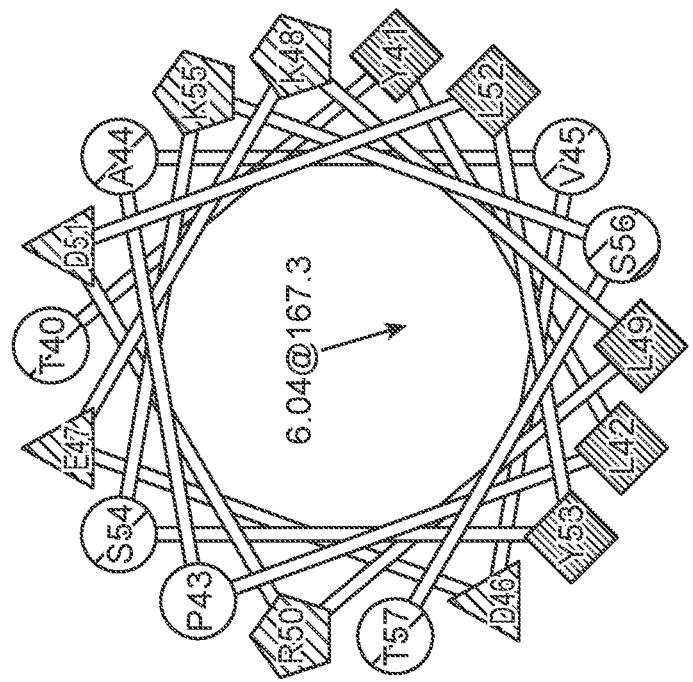
Figure 4B:
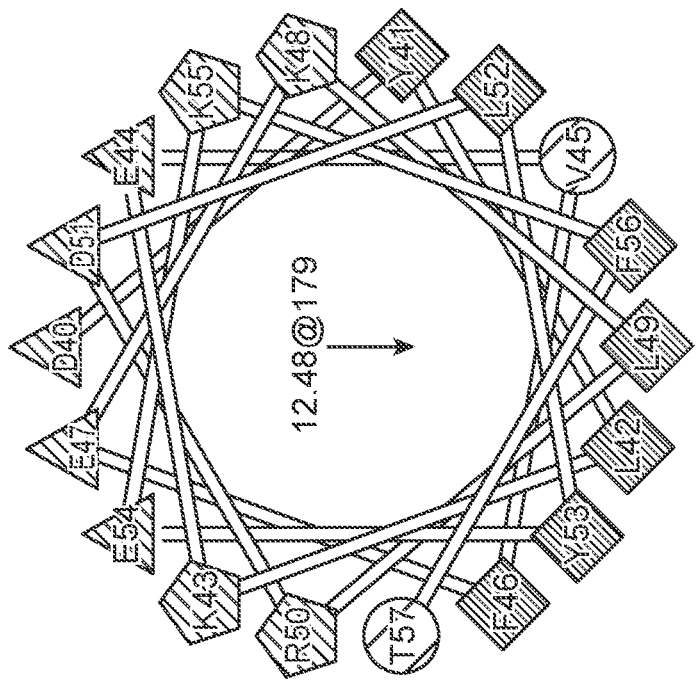
FIG. 4A and FIG. 4B present helical wheel plots of amino acid residues 40-57 of native apoC-II (SEQ ID NO: 69) and a variant Delta6' (SEQ ID NO: 72), with FIG. 4A representing the native apoC-II and FIG. 4B representing the variant, Delta6'.
Figure 4A:
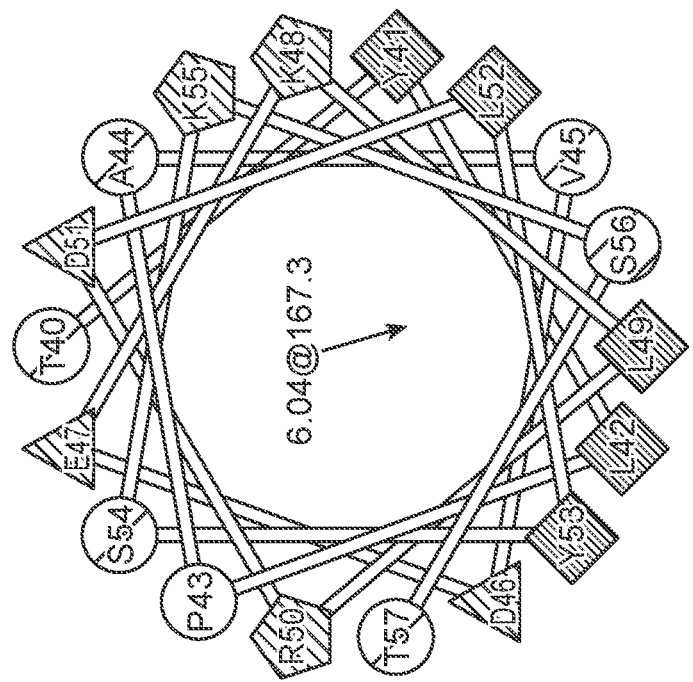

Some modifications, such as amino acid substitutions, increased the hydrophobic moment of the native amino acid sequence of apoC-II. For example, as shown in FIG. 2A and FIG. 2B, the T to D substitution at position 40, the P to K substitution at position 43, the D to F substitution at position 46, and the S to F substitution at position 56 increased the hydrophobic moment of amino acid residues 40-57 from 6.04 to 9.62. As shown in FIG. 3A and FIG. 3B, the T to D substitution at position 40, the P to K substitution at position 43, the A to E substitution at position 44, the D to F substitution at position 46, and the S to F substitution at position 56 increased the hydrophobic moment of amino acid residues 40-57 from 6.04 to 11.08. FIG. 4A and FIG. 4B show that a T to D substitution at position 40, the P to K substitution at position 43, the A to E substitution at position 44, the D to F substitution at position 46, the S to E substitution at position 54, and the S to F substitution at position 56 increased the hydrophobic moment of amino acid residues 40-57 from 6.04 to 12.48.

Chemical modifications were also introduced to increase the association of the apoC-II mimetic peptides for lipid particles and to enhance other therapeutic characteristics of the apoC-II mimetic peptides, such as increased cell permeability and/or prolonged biological half-life. FIG. 5 shows the examples of apoC-II mimetic peptides modified by stearic acid.

A list of apoC-II mimetic peptides and their sequences is show in Table 2 below, where "nL" indicates norleucine and "Aib" indicates aminoisobutyric acid.

TABLE 2

| Name | Sequence | SEQ ID NO |
|---|---|---|
| Delta6 | DYLKEVFEKLRDLYEKFTAAnLSTYTGIFTDQVLSVLKGEE | SEQ ID NO: 6 |
| Delta6V | DYLKEVFEKLRDLYEKFTAAVSTYTGIFTDQVLSVLKGEE | SEQ ID NO: 7 |
| Delta6L | DYLKEVFEKLRDLYEKFTAALSTYTGIFTDQVLSVLKGEE | SEQ ID NO: 8 |
| Delta6PV | DYLKEVFEKLRDLYEKFTPAVSTYTGIFTDQVLSVLKGEE | SEQ ID NO: 9 |
| Delta6PL | DYLKEVFEKLRDLYEKFTPALSTYTGIFTDQVLSVLKGEE | SEQ ID NO: 10 |
| Delta6MP | DYLKEVFEKLRDLYEKFTPAMSTYTGIFTDQVLSVLKGEE | SEQ ID NO: 11 |
| Delta6MPK-4R | DYLREVFERLRDLYERKTPAMSTYTGIFTDQVLSVLRGEE | SEQ ID NO: 12 |
| Delta6-NH | DYLKEVFEKLRDLYEKFTAAnLSTYTGIFTDQVLSVLKGEE$_{NH2}$ | SEQ ID NO: 13 |
| Delta6b-P | DYLKEVFEKLRDLYEKK$_{C18}$TPAnLSTYTGIFTDQVLSVLKGEE | SEQ ID NO: 14 |
| Delta6b-A | DYLKEVFEKLRDLYEKK$_{C18}$TAAnLSTYTGIFTDQVLSVLKGEE | SEQ ID NO: 15 |
| Delta4 | DYLKAVFEKLRDLYSKFTAAnLSTYTGIFTDQVLSVLKGEE | SEQ ID NO: 16 |
| Delta4 S15E | DYLKAVFEKLRDLYEKFTAAnLSTYTGIFTDQVLSVLKGEE | SEQ ID NO: 17 |
| Delta4 T18F | DYLKAVFEKLRDLYSKFFAAnLSTYTGIFTDQVLSVLKGEE | SEQ ID NO: 18 |
| Delta4 Y24S | DYLKAVFEKLRDLYSKFTAAnLSTSTGIFTDQVLSVLKGEE | SEQ ID NO: 19 |
| Delta4 Q31R | DYLKAVFEKLRDLYSKFTAAnLSTYTGIFTDRVLSVLKGEE | SEQ ID NO: 20 |
| Delta4 Q31K | DYLKAVFEKLRDLYSKFTAAnLSTYTGIFTDKVLSVLKGEE | SEQ ID NO: 21 |
| Delta4 Truncated | KRDLYEKKFAAnLSTYTGIFTDQVLSVLKGEE | SEQ ID NO: 22 |
| mono-acyl-Delta4 | $_{C18}$DYLKAVFEKLRDLYSKFTAAnLSTYTGIFTDQVLSVLKGEE | SEQ ID NO: 23 |
| bi-acyl-Delta4 | $_{C18}$DYLKAVFEKK$_{C18}$RDLYSKFTAAnLSTYTGIFTDQVLSVLKGEE | SEQ ID NO: 24 |
| Delta4b | DYLKAVFEKLRDLYSKFTPAMSTYTGIFTDQVLSVLKGEE | SEQ ID NO: 25 |
| Delta4b S15E | DYLKAVFEKLRDLYEKFTPAMSTYTGIFTDQVLSVLKGEE | SEQ ID NO: 26 |
| Delta4b S15K | DYLKAVFEKLRDLYKKFTPAMSTYTGIFTDQVLSVLKGEE | SEQ ID NO: 27 |
| Delta4b R11K | DYLKAVFEKLKDLYSKFTPAMSTYTGIFTDQVLSVLKGEE | SEQ ID NO: 28 |

TABLE 2-continued

| Name | Sequence | SEQ ID NO |
|---|---|---|
| Delta4b Y2W | DWLKAVFEKLRDLYSKFTPAMSTYTGIFTDQVLSVLKGEE | SEQ ID NO: 29 |
| Delta4b T18F | DYLKAVFEKLRDLYSKFFPAMSTYTGIFTDQVLSVLKGEE | SEQ ID NO: 30 |
| Delta4b V6F/F7Y/Y14L/F17A/T18F | DYLKAFYEKLRDLLSKAFPAMSTYTGIFTDQVLSVLKGEE | SEQ ID NO: 31 |
| Delta4b-1 | DYLKAVK$_{C18}$EKLRDLYSKFTPAMSTYTGIFTDQVLSVLKGEE | SEQ ID NO: 32 |
| Delta4b-2 | DYLKAVFEKK$_{C18}$RDLYSKFTPAMSTYTGIFTDQVLSVLKGEE | SEQ ID NO: 33 |
| Delta4b-3 | DYLKAVFEKLRDLYSKK$_{C18}$TPAMSTYTGIFTDQVLSVLKGEE | SEQ ID NO: 34 |
| Delta4c | DYLKAVFEKLRDLYSKFTAAK$_{C16}$STYTGIFTDQVLSVLKGEE | SEQ ID NO: 35 |
| Delta4c trunc3 | KAVFEKLRDLYSKFTAAK$_{C16}$STYTGIFTDQVLSVLKGEE | SEQ ID NO: 36 |
| Delta4c trunc4 | DVFEKLRDLYSKFTAAK$_{C16}$STYTGIFTDQVLSVLKGEE | SEQ ID NO: 37 |
| Delta4c trunc7 | EKLRDLYSKFTAAK$_{C16}$STYTGIFTDQVLSVLKGEE | SEQ ID NO: 38 |
| Delta4c trunc10 | RDLYSKFTAAK$_{C16}$STYTGIFTDQVLSVLKGEE | SEQ ID NO: 39 |
| Delta4c trunc11 | DLYSKFTAAK$_{C16}$STYTGIFTDQVLSVLKGEE | SEQ ID NO: 40 |
| Delta4c trunc14 | DKFTAAK$_{C16}$STYTGIFTDQVLSVLKGEE | SEQ ID NO: 41 |
| Delta5 | DYLKEVFEKLRDLYSKFTAAnLSTYTGIFTDQVLSVLKGEE | SEQ ID NO: 42 |
| Delta5b Y2W | DWLKAVFEKLRDLYEKFTPAMSTYTGIFTDQVLSVLKGEE | SEQ ID NO: 43 |
| Delta5b T18F | DYLKAVFEKLRDLYEKFFPAMSTYTGIFTDQVLSVLKGEE | SEQ ID NO: 44 |
| Delta5b Y2W/T18F | DWLKAVFEKLRDLYEKFFPAMSTYTGIFTDQVLSVLKGEE | SEQ ID NO: 45 |
| Delta5b Y2W M21NL | DWLKAVFEKLRDLYEKFTPAnLSTYTGIFTDQVLSVLKGEE | SEQ ID NO: 46 |
| Delta5b T18F M21NL | DYLKAVFEKLRDLYEKFFPAnLSTYTGIFTDQVLSVLKGEE | SEQ ID NO: 47 |
| Delta5b Y2W/T18F M21NL | DWLKAVFEKLRDLYEKFFPAnLSTYTGIFTDQVLSVLKGEE | SEQ ID NO: 48 |
| C2thirdhelix | AMSTYTGIFTDQVLSVLKGEE | SEQ ID NO: 49 |
| C2thirdhelix Stearylpos1 | $_{C18}$AMSTYTGIFTDQVLSVLKGEE | SEQ ID NO: 50 |
| C2thirdhelix Stearylpos2 | AK$_{C18}$STYTGIFTDQVLSVLKGEE | SEQ ID NO: 51 |
| C2thridhelix Stearylpos17 | AMSTYTGIFTDQVLSVLK$_{C18}$GEE | SEQ ID NO: 52 |
| Delta6T18F-PV | DYLKEVFEKLRDLYEKFFPAVSTYTGIFTDQVLSVLKGEE | SEQ ID NO: 53 |

TABLE 2-continued

| Name | Sequence | SEQ ID NO |
|------|----------|-----------|
| Delta6T18F-PV-AIB7,17 | DYLKEVAibEKLRDLYEKAibFPAVSTYTGIFTDQVLSVLKGEE | SEQ ID NO: 54 |
| Delta13-31-PV | DKVKEFLSEYWEKAKEFAPAVSTYTGIFTDQVLSVLKGEE | SEQ ID NO: 55 |

Example 2: Exemplary ApoC-II Mimetic Peptides with Amino Acid Substitutions Promote TG Hydrolysis In Vitro To determine the possible impact of apoC-II mimetic peptides on hydrolysis of TG, we assessed the effect of the peptides using an in vitro lipolysis assay.

Figure 6:
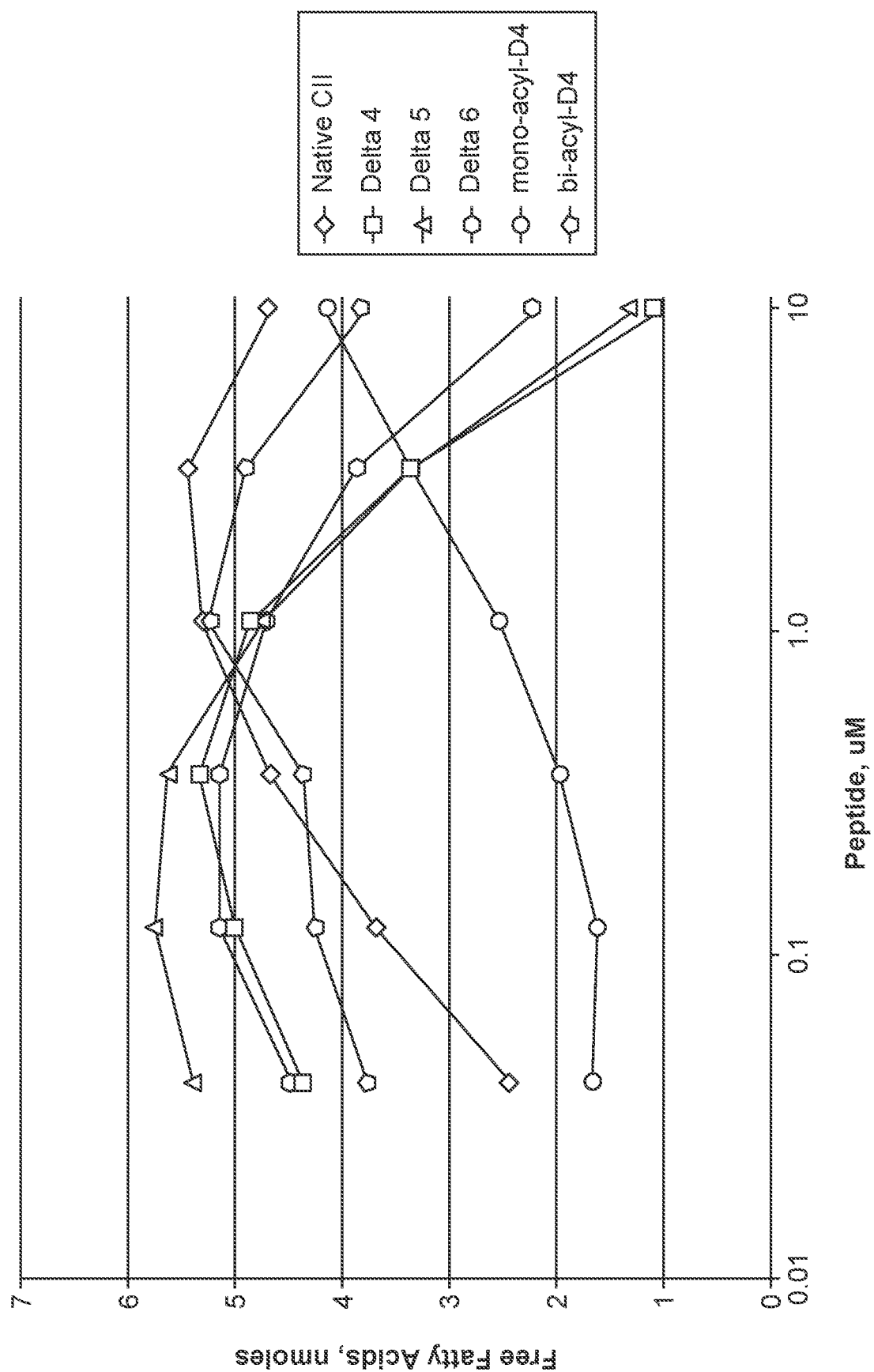
FIG. 6 presents the results of in vitro LPL assay of exemplary apoC-III mimetic peptides and variants with chemical modifications using apoC-II deficient patient sera as substrate. Native full-length human apoC-II protein was used as control.

LPL assay with apoC-II deficient patient sera showed that exemplary apoC-II mimetic peptides Delta4, Delta5, and Delta6, as well as Delta4 variants mono-acyl-Delta4 and bi-acyl-Delta4, were capable of promoting TG hydrolysis in the presence of LPL. At lower concentrations, most of the tested mimetic peptides, such as Delta4, Delta5, and Delta6, worked more efficiently than the native apoC-II protein (FIG. 6).

Figure 7:
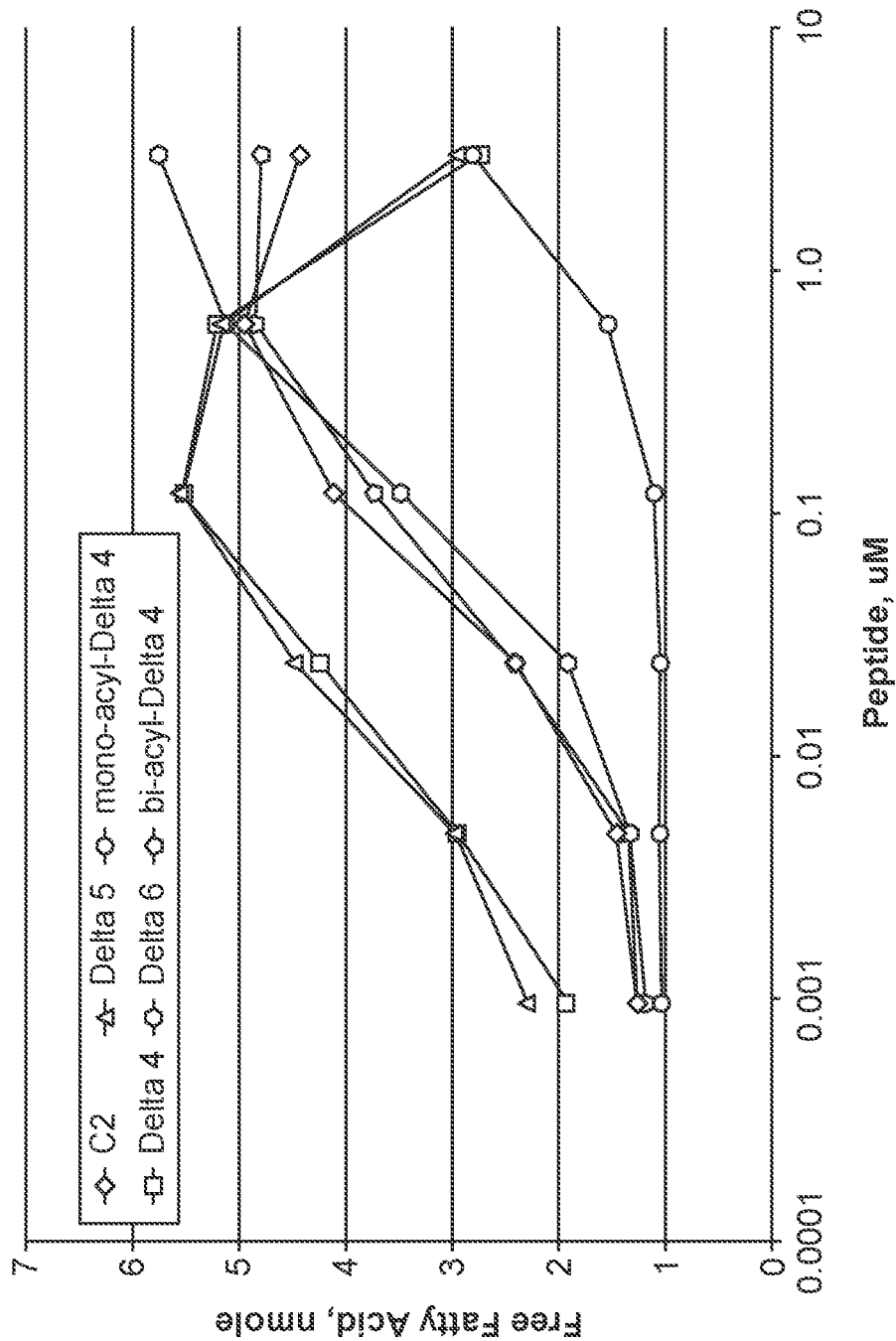
FIG. 7 presents the results of in vitro LPL assay of exemplary apoC-III mimetic peptides and variants with chemical modifications using Intralipid as substrate. Native full-length human apoC-II protein was used as control.

LPL assay using Intralipid as substrate confirmed that all apoC-II mimetic peptide tested were capable of promoting TG hydrolysis in the presence of LPL. The apoC-II mimetic peptides Delta4 and Delta5 worked more efficiently than the native apoC-II protein at concentrations of between about 1 nM to about 10 µM (FIG. 7).

These results show that the exemplary apoC-II mimetic peptides Delta4, Delta5, and Delta6 are capable of promoting TG hydrolysis in vitro.

Example 3: Variants of Delta4 and Third Helix of apoC-II Promote TG Hydrolysis In Vitro The hinge region between helix 2 and helix 3 of apoC-II protein allows the two helices to retain a relatively straight conformation. The helix 3 bends away from helix2 uniformly in different directions over an angle of no more than about 20°. This conformation is believed to help helix 3, which contains the LPL activating domain, to attach to the micelle surface of lipoprotein. Incorporation of a proline at position 58 of the hinge domain preserves and accentuates the conformation. Variants of Delta4, such as Delta4b, Delta4b-1, and Delta4b S54E, comprise a proline at position 58.

The apoC-II mimetic peptide C2thirdhelix comprises amino acid residues 59-79 of apoC-II protein. C2thirdhelixStearylpos1, C2thirdhelixStearylpos2, and C2thirdhelixStearylpos17 comprise a stearic acid modification of C2thirdhelix at different amino acid residues.

Figure 8:
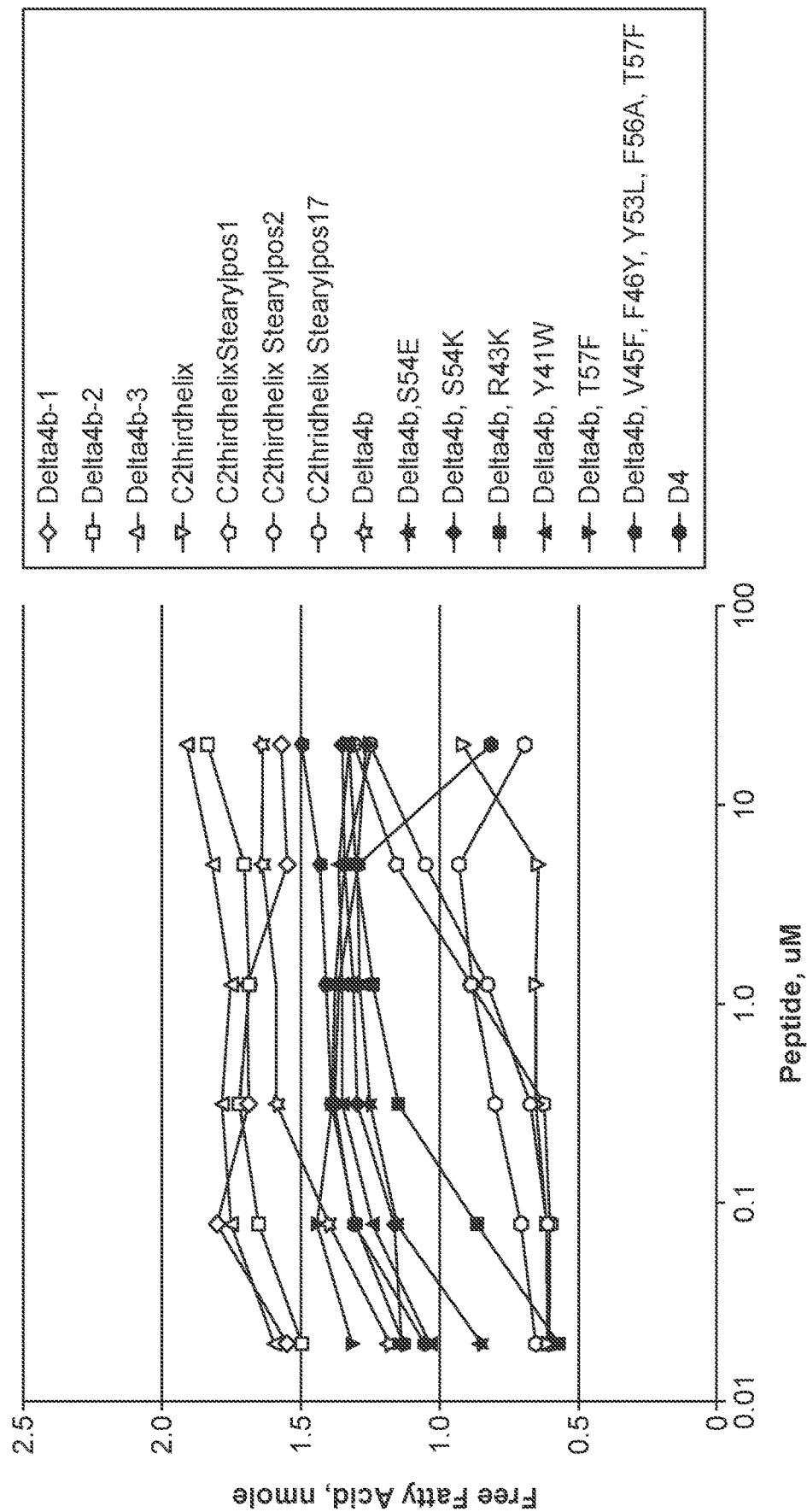
FIG. 8 presents the results of in vitro LPL assay of exemplary apoC-III mimetic peptide Delta4, Delta4 variants, and variants of the third helix of apoC-II using apoC-II deficient patient sera as substrate.
Figure 9:
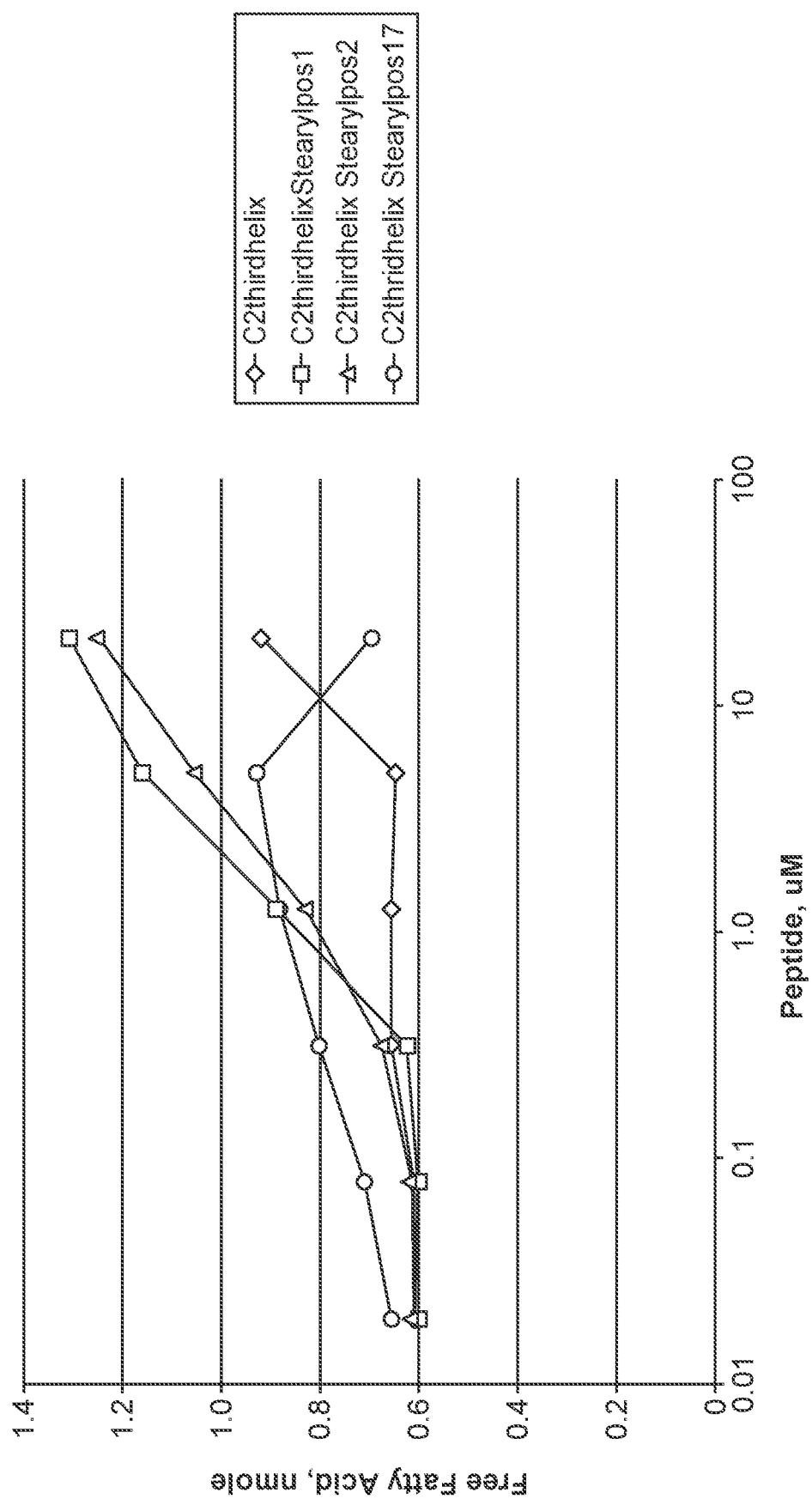
FIG. 9 shows the results of in vitro LPL assay of variants of the third helix of apoC-II using apoC-II deficient patient sera as substrate.
Figure 10:
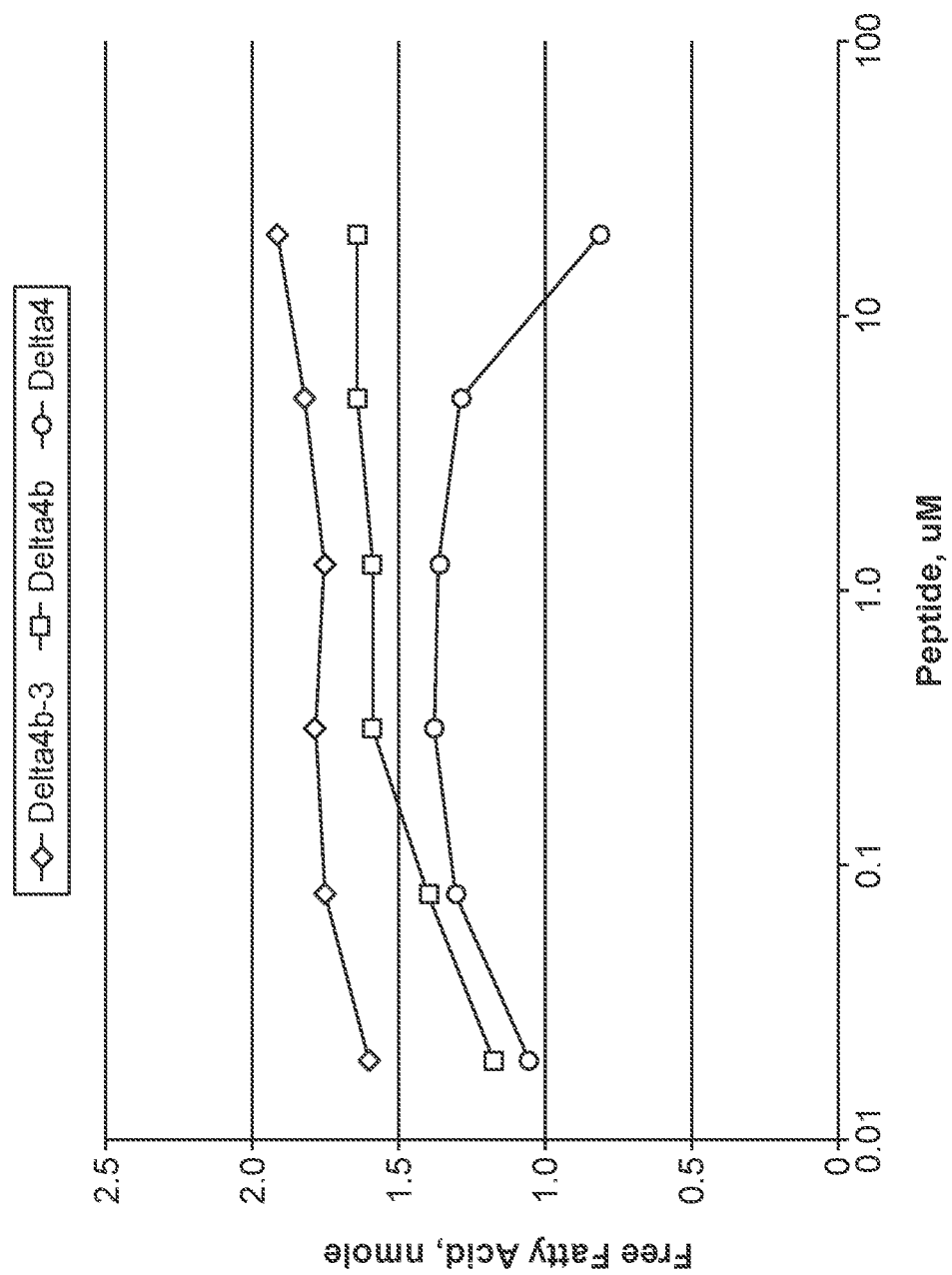
FIG. 10 shows the results of in vitro LPL assay of variants of exemplary apoC-II mimetic peptide Delta4 using apoC-II deficient patient sera as substrate.
Figure 11:
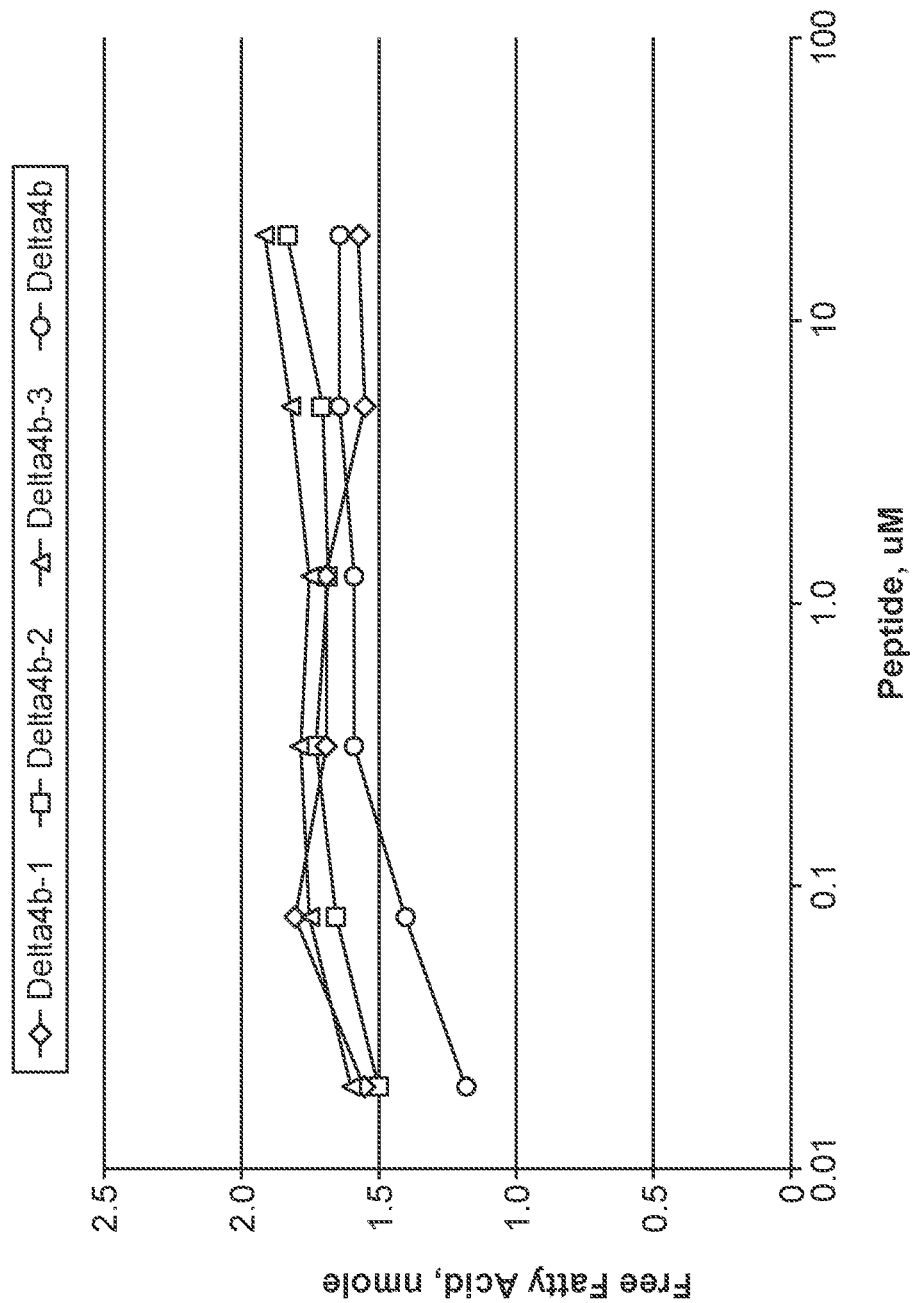
FIG. 11 shows the results of in vitro LPL assay of variants of exemplary apoC-II mimetic peptide Delta4 using apoC-II deficient patient sera as substrate.

As shown in FIG. 8, most of the above-mentioned apoC-III mimetic peptides exhibited the ability to promote TG hydrolysis in the presence of LPL when apoC-III deficient patient sera were used as substrate. A closer look at the results of C2thirdhelix, C2thirdhelixStearylpos1, C2thirdhelixStearylpos2, and C2thirdhelixStearylpos17 revealed that lipidation enhanced the ability of C2thirdhelix to promote TG hydrolysis (FIG. 9). A comparison of the apoC-III mimetic peptides Delta4, Delta4b, and Delta4b-3 revealed that incorporation of proline at position 58 and the stearic acid modification at the lysine residue at position 56 enhanced the TG clearance ability of the exemplary apoC-III mimetic peptide Delta4 (FIG. 10). FIG. 11 confirmed that lipidation of apoC-III mimetic peptide Delta4b enhanced its ability to enhance lipolysis, especially at lower concentrations.

Figure 12:
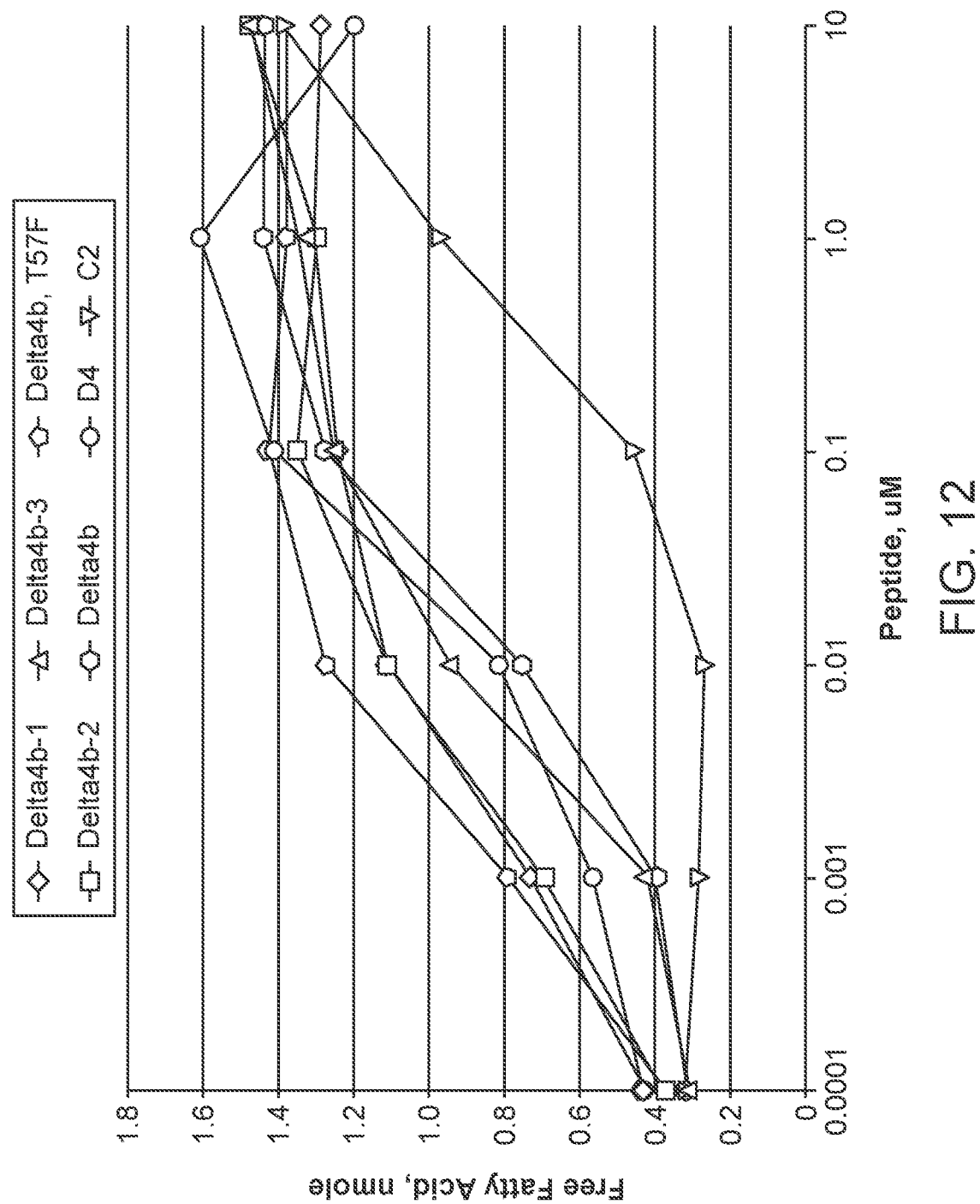
FIG. 12 presents the results of in vitro LPL assay of exemplary apoC-III mimetic peptide Delta4 and its variants using apoC-II deficient patient sera as substrate. The concentration of apoC-II mimetic peptide ranges from 100 pM to 10 µM. Native full-length human apoC-II protein was used as control.

We further tested the apoC-III mimetic peptides in a wide range of concentrations from 100 pM to 10 µM. The apoC-III mimetic peptides, Delta4b-1, Delta4b-2, Delta4b-3, Delta4b, Delta4b T57F, and Delta4, promoted TG hydrolysis in a dose-dependent manner. All of the apoC-III mimetic peptides tested in this experiment worked more efficiently than the full length apoC-II protein (FIG. 12).

Figure 13:
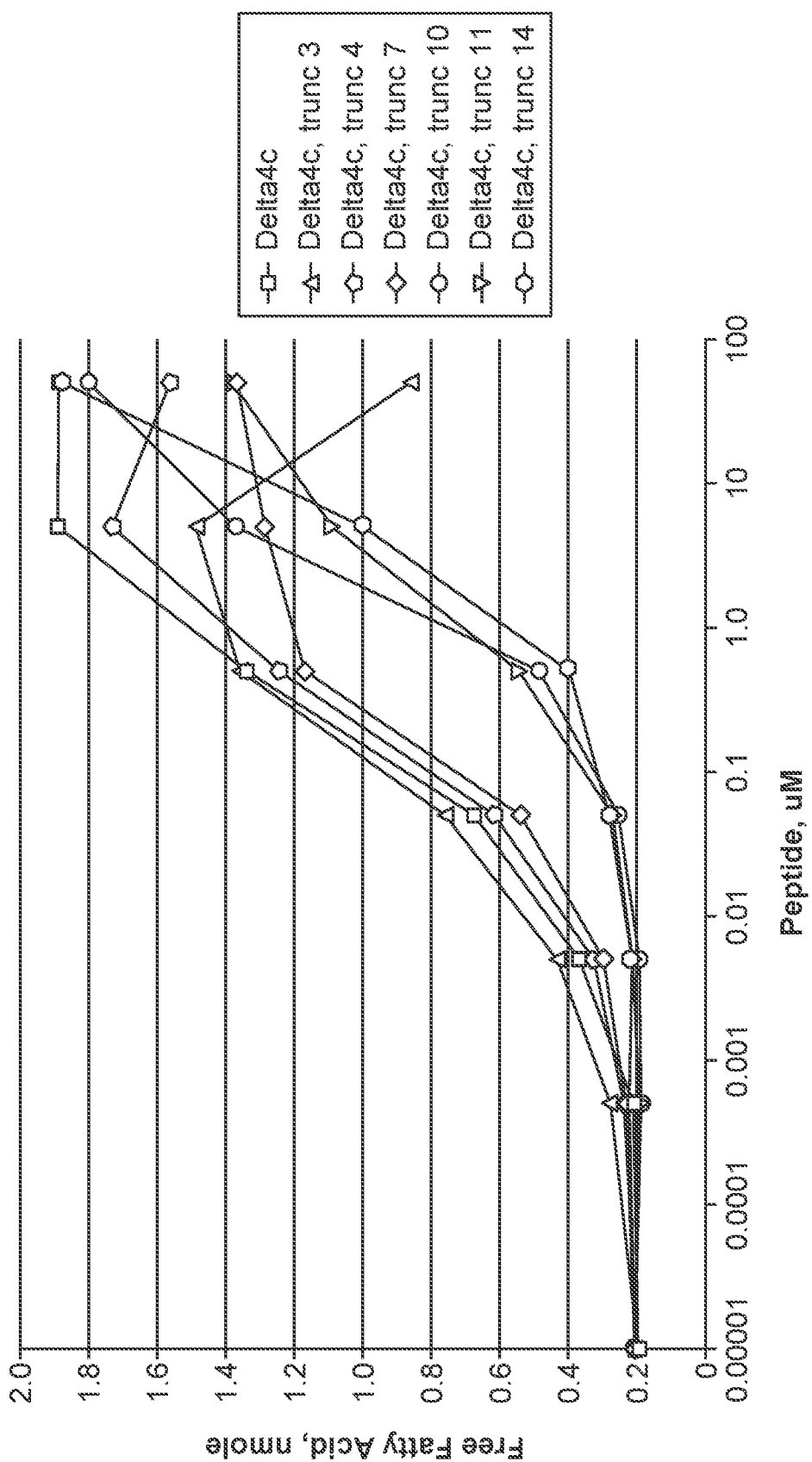
FIG. 13 presents the results of in vitro LPL assay of truncation variants of exemplary apoC-III mimetic peptide Delta4 using apoC-II deficient patient sera as substrate. The concentration of apoC-II mimetic peptide ranges from 10 pM to 100 µM.

Delta4c peptide comprised a palmitic acid modified lysine (K) at position 60, and its derivatives included truncations at the C-terminal by 3, 4, 7, 10, 11, or 14 amino acids. In an LPL assay with apoC-III deficient patient sera as substrate and over a range of peptide concentrations from 10 pM to 100 Delta4c and its truncation variants promoted TG hydrolysis (FIG. 13).

Together, these results show that variants of exemplary apoC-III mimetic peptide Delta4 and variants of third helix of apoC-III can promote TG hydrolysis in vitro.

Example 4: Variants of Deltas Promote TG Hydrolysis In Vitro

Additional amino acid substitutions were made to apoC-III mimetic peptide Delta5b, which comprises a proline at position 58 and a methionine at position 60.

Figure 14:
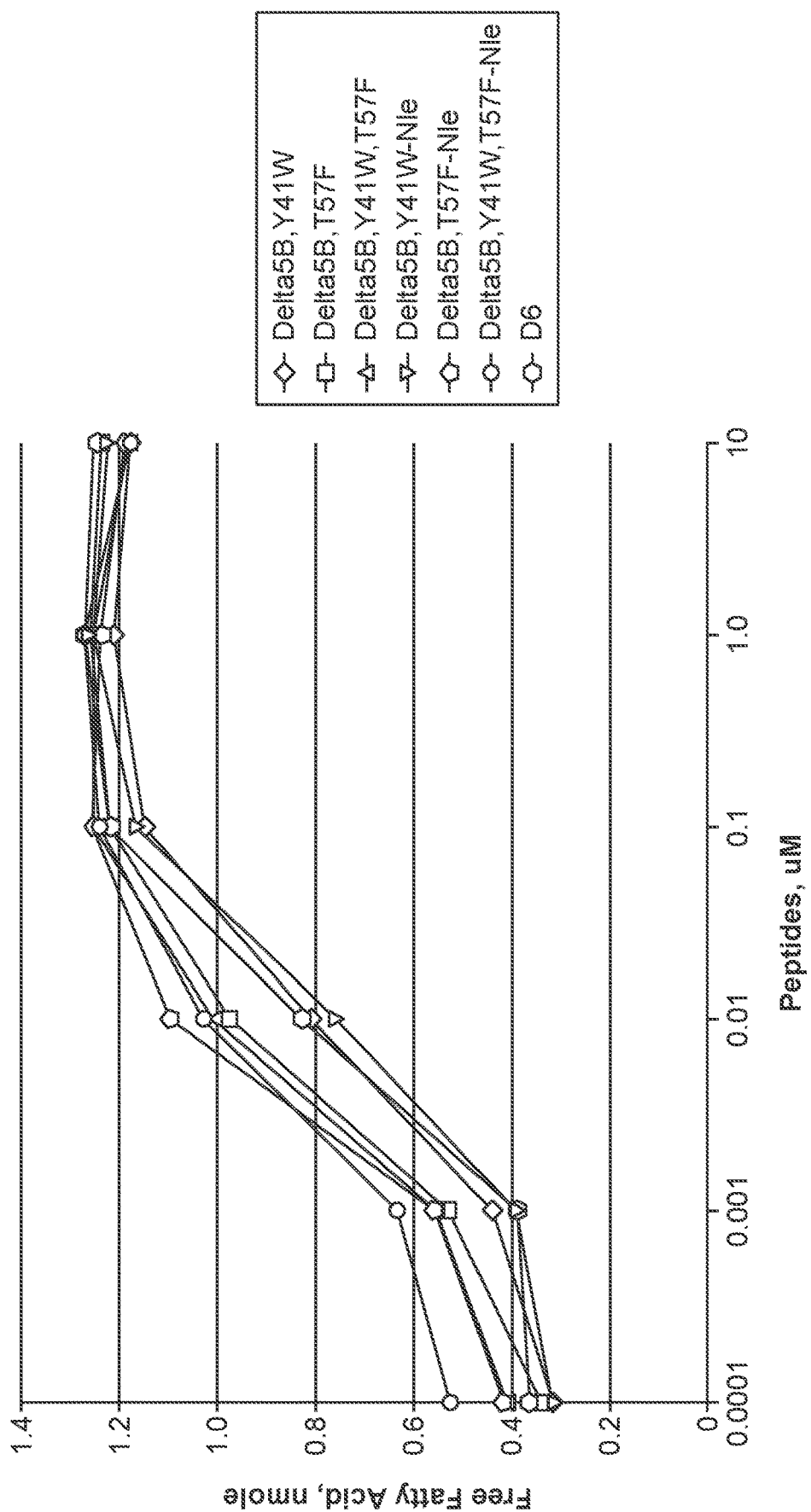
FIG. 14 presents the results of in vitro LPL assay of variants of exemplary apoC-II mimetic peptide Delta5 and the exemplary apoC-II mimetic peptide Delta6, using apoC-II deficient patient sera as substrate. The concentration of apoC-II mimetic peptide ranges from 100 pM to 10 µM.

LPL assay was performed using apoC-II deficient patient sera as substrate. The peptides were tested in a range of concentrations from 100 pM to 10 nM. As shown in FIG. 14, all variants of Delta5 with the indicated amino acid substitutions and Delta6 exhibited the ability to promote TG hydrolysis in a dose dependent matter.

These results show that variants of exemplary apoC-II mimetic peptide Delta5 are capable of promoting TG hydrolysis in vitro.

Example 5: Variants of Delta6 Promote TG Hydrolysis In Vitro

The exemplary apoC-II mimetic peptide Delta6 was further modified to be more suitable for recombinant expression. Delta6L comprises a leucine (L) residue at position 60. Delta6PV comprises a proline (P) at position 58 and a valine (V) at position 60. Delta6PV comprises a proline (P) at position 58 and a leucine (V) at position 60. Delta6T18F-PV further comprises a phenylalanine (F) at position 57 compared to Delta6PV. Delta6T18F-PV-AIB7,17 further comprises an aminoisobutyric acid (Aib) at positions 46 and 56 and a phenylalanine (F) at position 57 compared to Delta6PV.

As shown in FIGS. 15A-D, Delta6 peptide and its variants Delta6L, Delta6PV, and Delta6PL activated LPL in vitro when hypertriglyceridemia patient sera were used as substrate. The triglyceride concentrations of the patient sera ranged from about 1000 mg/dL to about 1700 mg/dL.

Figure 51:
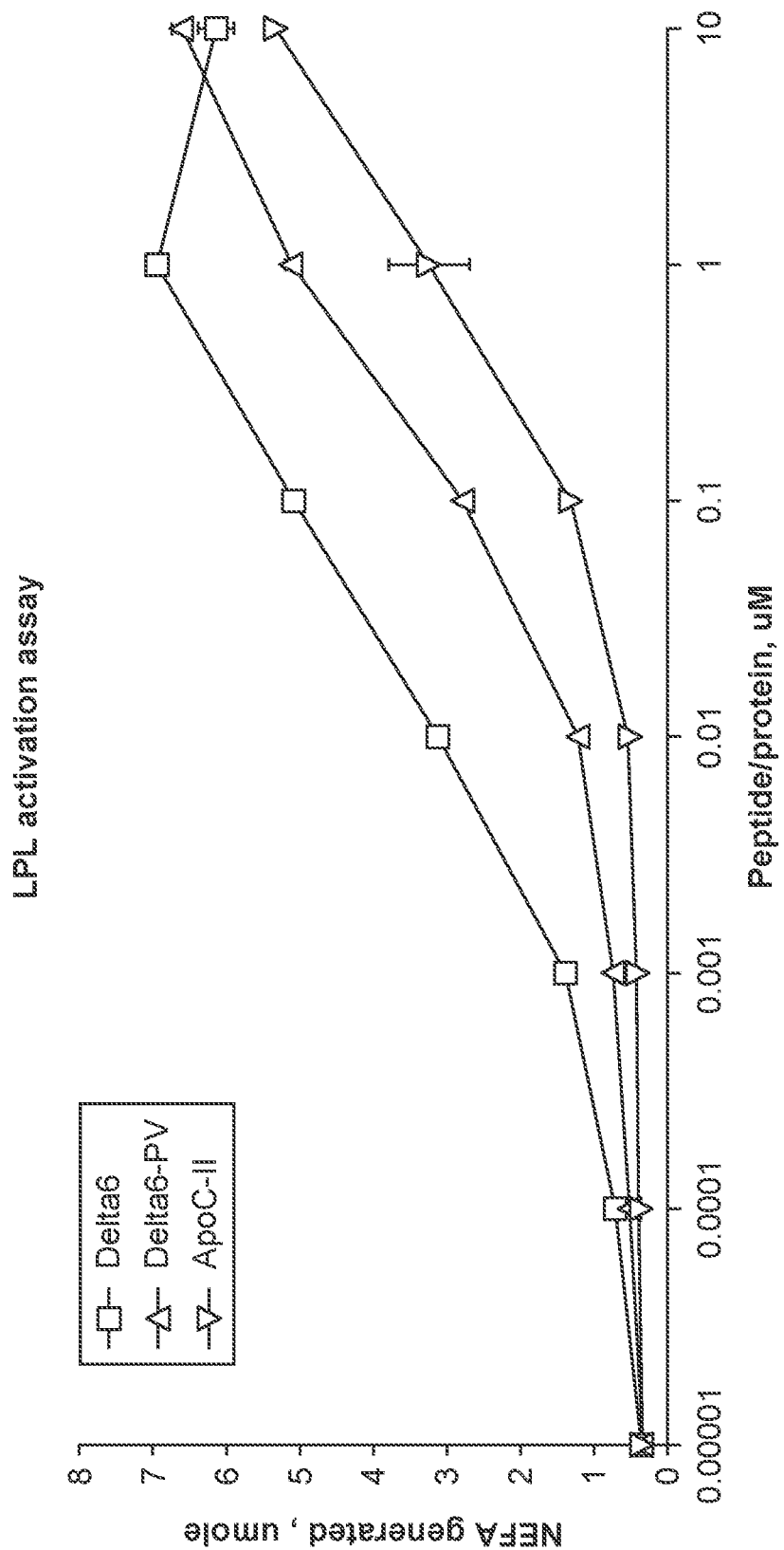
FIG. 51 represents the results of in vitro LPL assay of Delta6 and Delta6PV peptides using apoC-II deficient patient sera as substrate.

We further tested the activity Delta6 peptide and its variant Delta6PV in a wide range of concentrations from 10 pM to 10 µM. ApoC-II deficient patient sera were used as substrate. As shown in FIG. 51, Delta6 and Delta6PV activated LPL in vitro more efficiently than the full length apoC-II protein.

Figure 52:
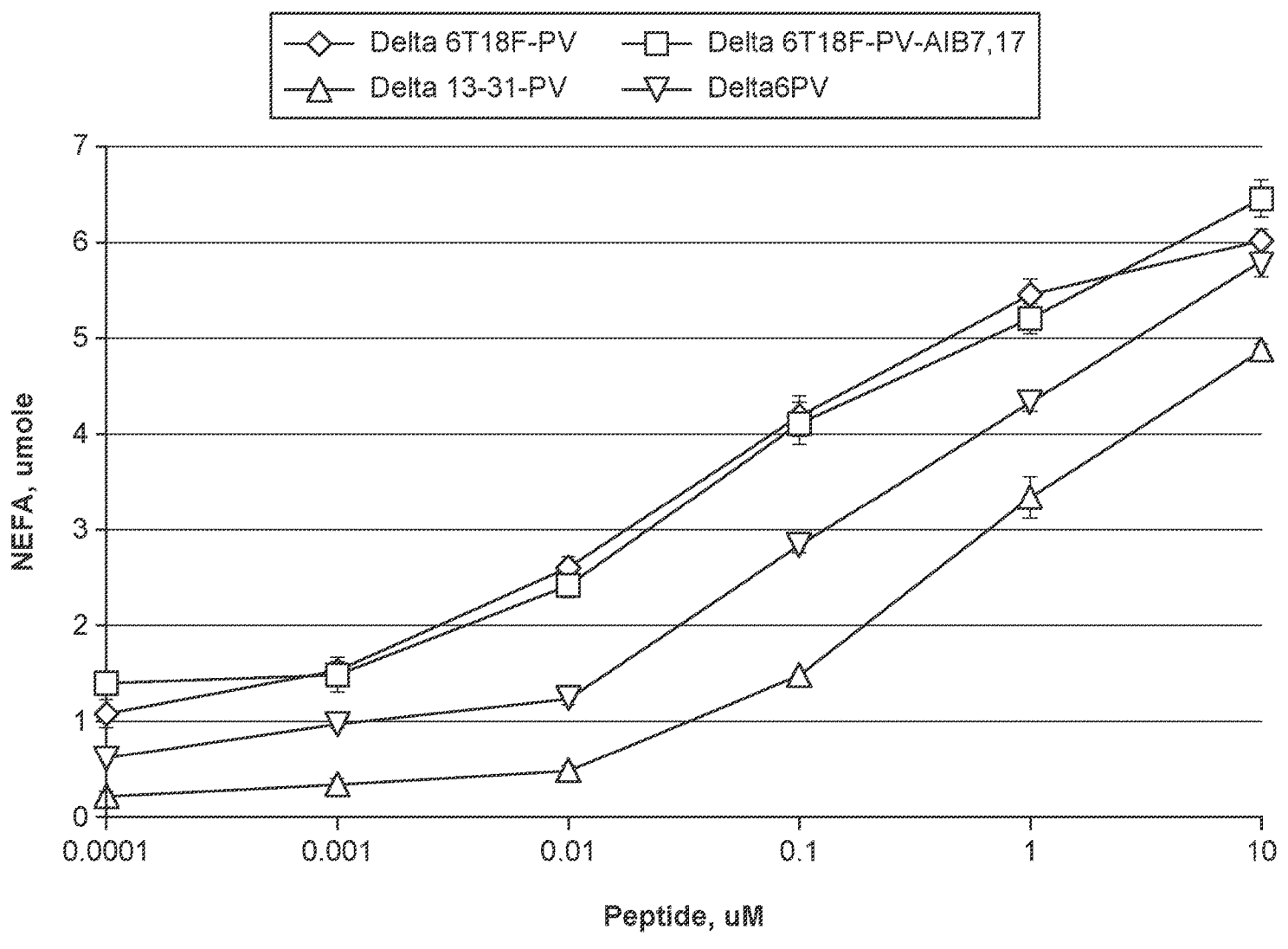

Additionally, Delta 6 variants Delta6PV, Delta6T18F-PV, and Delta6T18F-PV-AIB7,17 activated LPL in vitro with serum samples from apoC-II deficient patients (FIG. 52).

We generated an apoC-II mimetic peptide, Delta13-31-PV, which comprises a variant of helix 1 of apoC-II. Delta13-31-PV has the sequence of DKVKEFLSEYWE KAKEFAPAVSTYTGIFTDQVLSVLKGEE (SEQ ID NO: 55), with the amino acid substitutions to helix 1 of apoC-II underlined. The Delta13-31-PV peptide promoted TG hydrolysis in vitro in a dose-dependent manner (FIG. 52).

These results show that variants of exemplary apoC-II mimetic peptide Delta6 and the apoC-II mimetic peptide comprising the variant of helix 1 of apoC-II are capable of promoting TG hydrolysis in vitro.

Example 6: Delta4 and its Variants Enhanced In Vivo Lipolysis

ApoC-II is a cofactor for lipoprotein lipase, an enzyme that hydrolyzes triglycerides. ApoC-II deficiency results in hypertriglyceridemia in human subjects. As described in Sakurai et al., *J Pharmacol Exp Ther* 356:341-353, 2016, we created apoC-II knockout mice that had high plasma TG.

Figure 16:
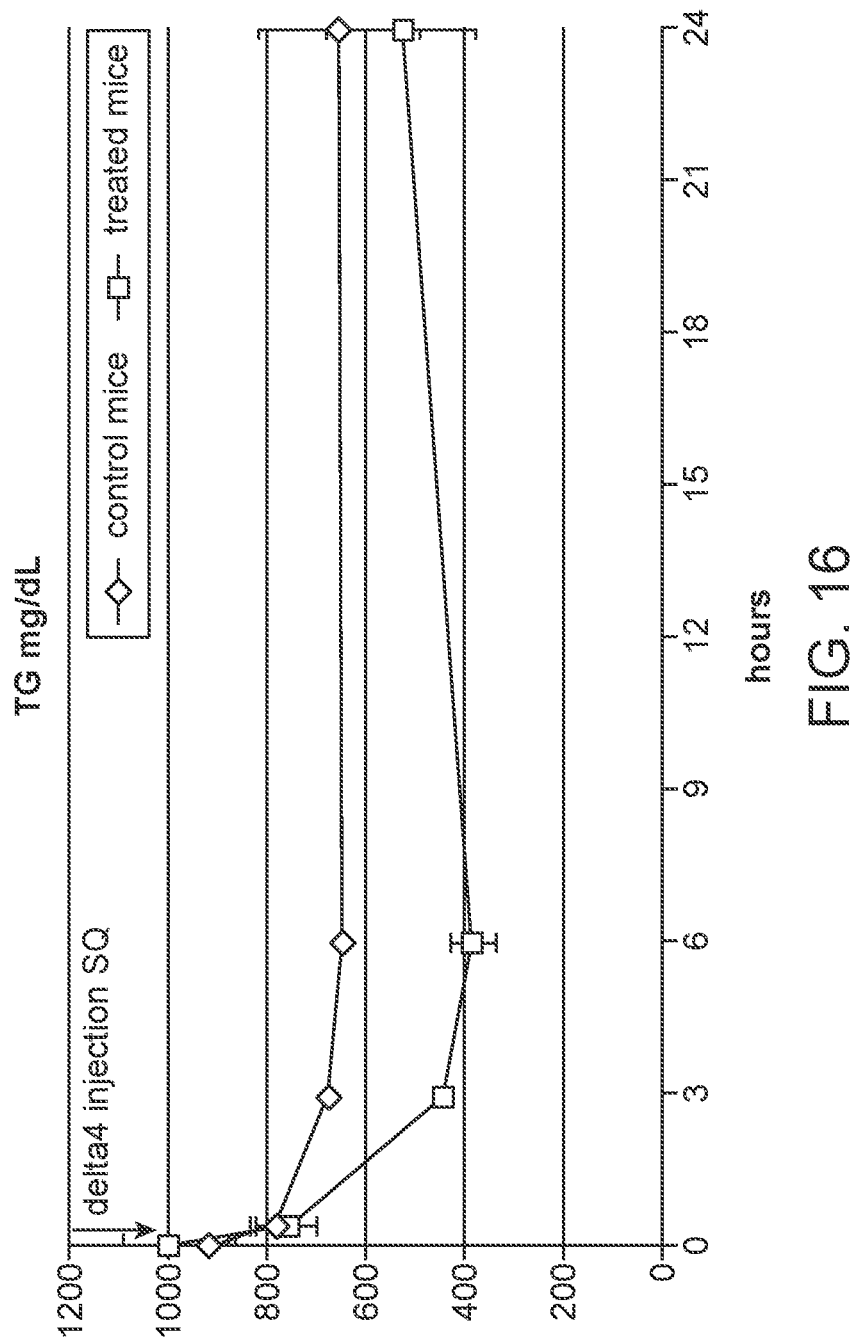
FIG. 16 presents the serum triglyceride (TG) level of apoC-II knockout mice after subcutaneous injection of apoC-II mimetic peptide Delta4. Saline was used as control.
Figure 17:
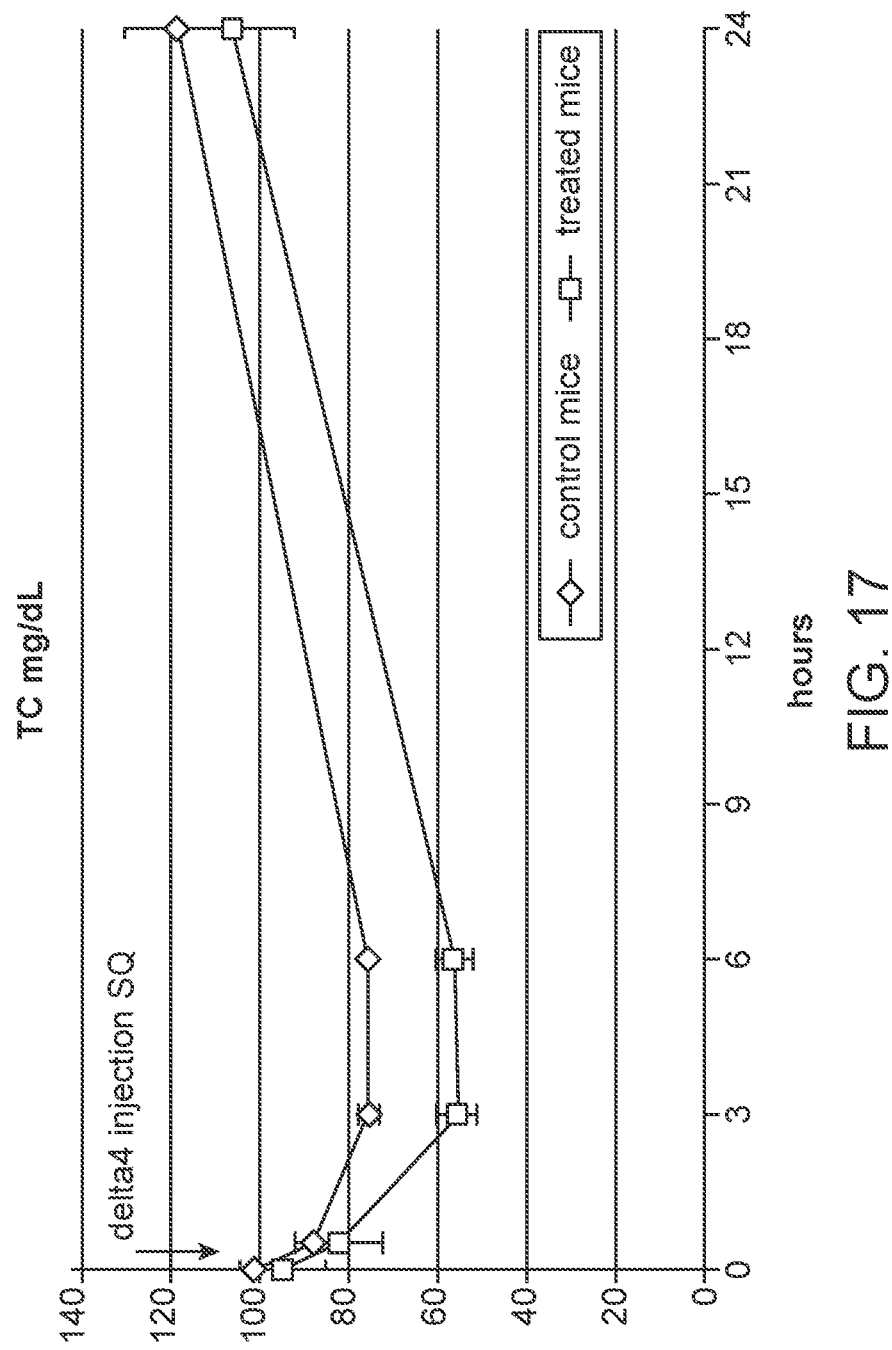
FIG. 17 presents the total cholesterol (TC) level of apoC-II knockout mice after subcutaneous injection of apoC-II mimetic peptide Delta4. Saline was used as control.

ApoC-II mimetic peptide Delta4 was injected subcutaneously into apoC-II knockout mice and the plasma lipids were monitored over time (FIG. 16). Injection of Delta4 resulted in a rapid and marked reduction of plasma TG. The subcutaneous injection of Delta4 also led to a decrease in total cholesterol level (FIG. 17).

Figure 18:
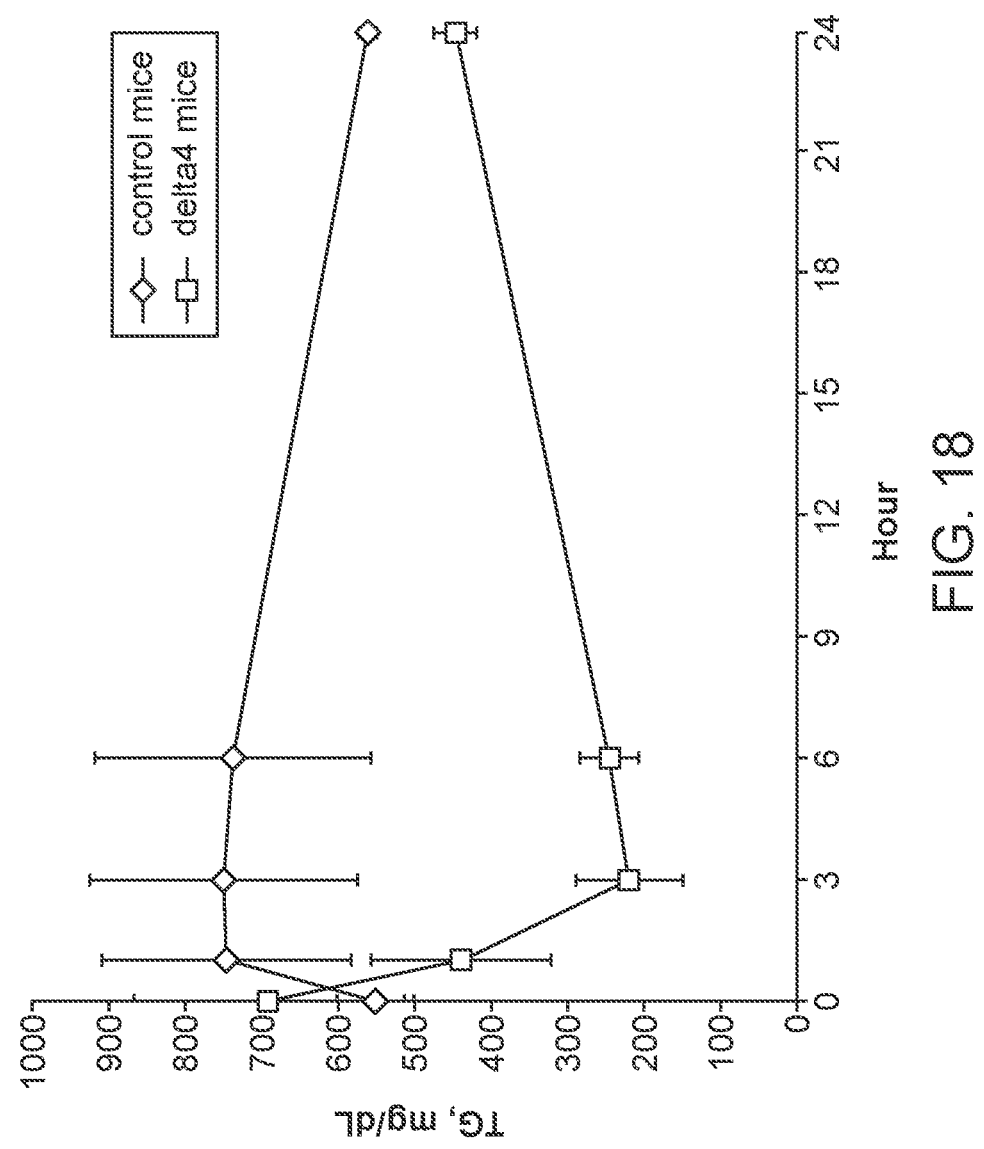
FIG. 18 presents the serum triglyceride (TG) level of apoC-II knockout mice after intraperitoneal injection of apoC-II mimetic peptide Delta4. Saline was used as control.
Figure 19:
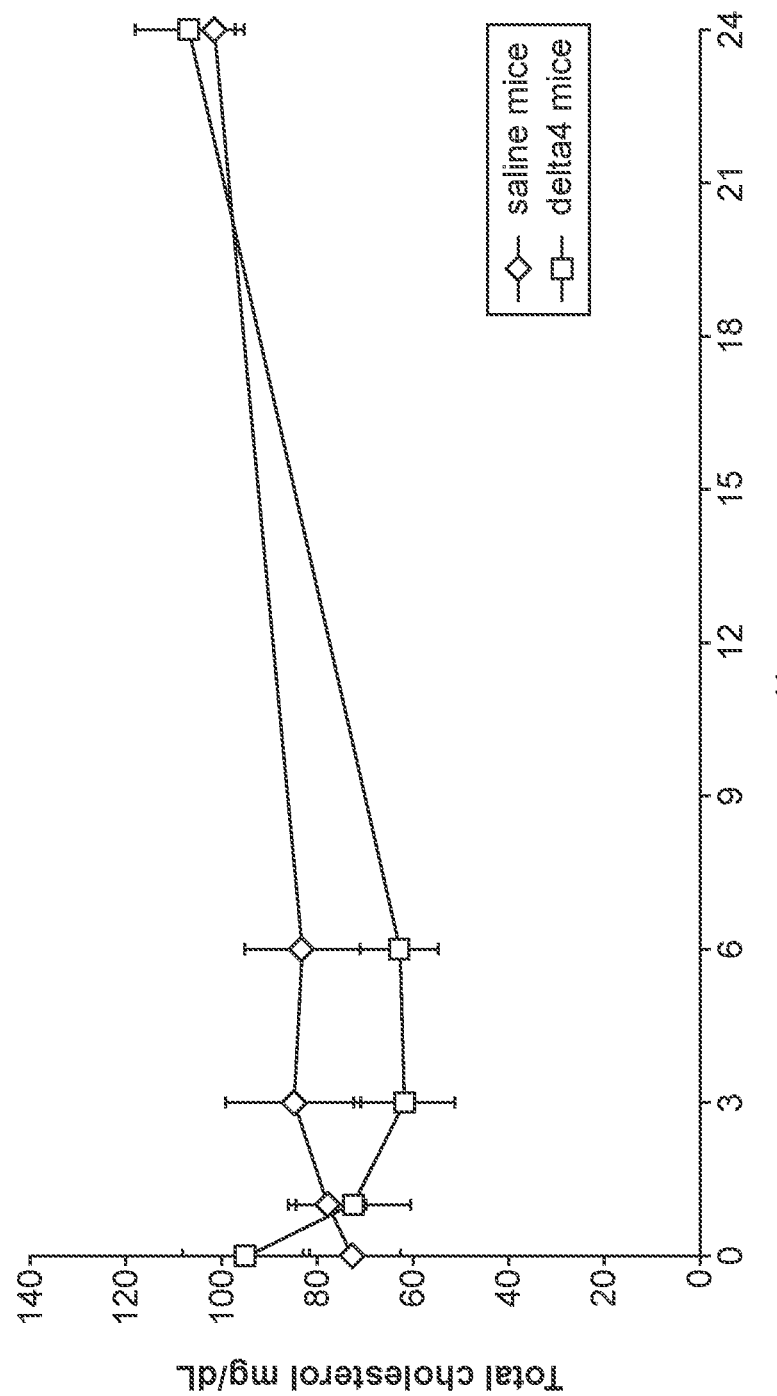
FIG. 19 presents the total cholesterol (TC) level of apoC-II knockout mice after intraperitoneal injection of apoC-II mimetic peptide Delta4. Saline was used as control.

The apoC-II knockout mice were also injected with Delta4 peptide intraperitoneally (FIGS. 18 and 19). Similarly, the Delta4 injection led to a marked reduction of plasma TG with a maximum decrease after about 3 hours. The intraperitoneal injection also led to a decrease in total cholesterol level.

Figure 20:
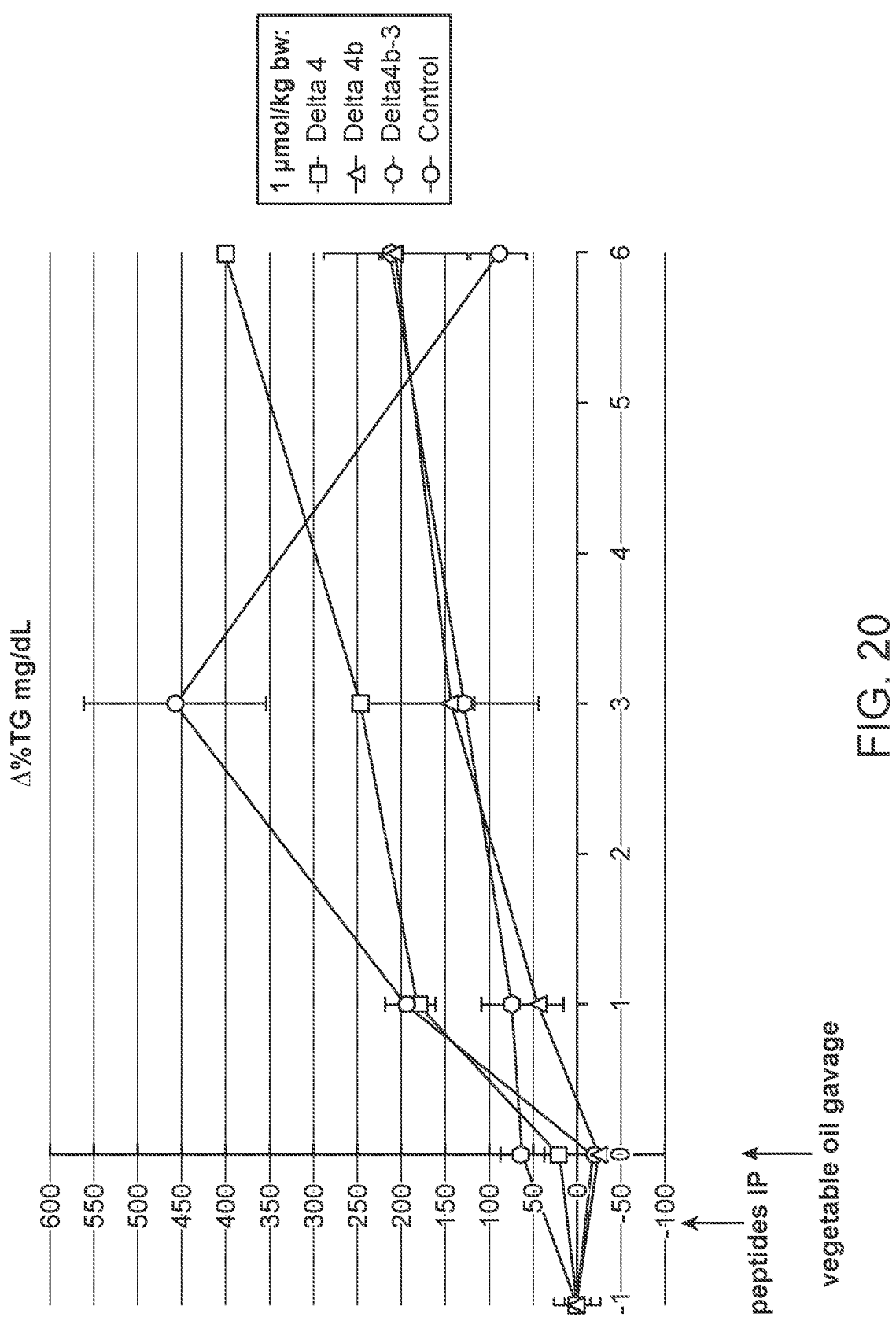
FIG. 20 shows the percentage change of serum triglyceride (TG) level of wild-type mice after vegetable oil gavage in the presence or absence of intraperitoneal injection of apoC-II mimetic peptide. The tested apoC-II mimetic peptides included Delta4, Delta4b and Delta4b-3. Saline was used as control.

Delta4 derivatives Delta4b and Delta4b-3 were also tested for their ability to promote TG hydrolysis in vivo (FIG. 20). After an oral gavage with vegetable oil, serum TG increased in C57BL/6 mice by about 4.5-fold by 3 h. When mice were intraperitoneally injected 30 min before gavage with an apoC-II mimetic peptide Delta4, Delta4b, or Delta4b-3, the TG increase was significantly reduced.

These results show that apoC-II mimetic peptide Delta4 and its variants have the ability to enhance in vivo lipolysis.

Example 7: Delta6 and its Variants Enhanced In Vivo Lipolysis

Figure 21:
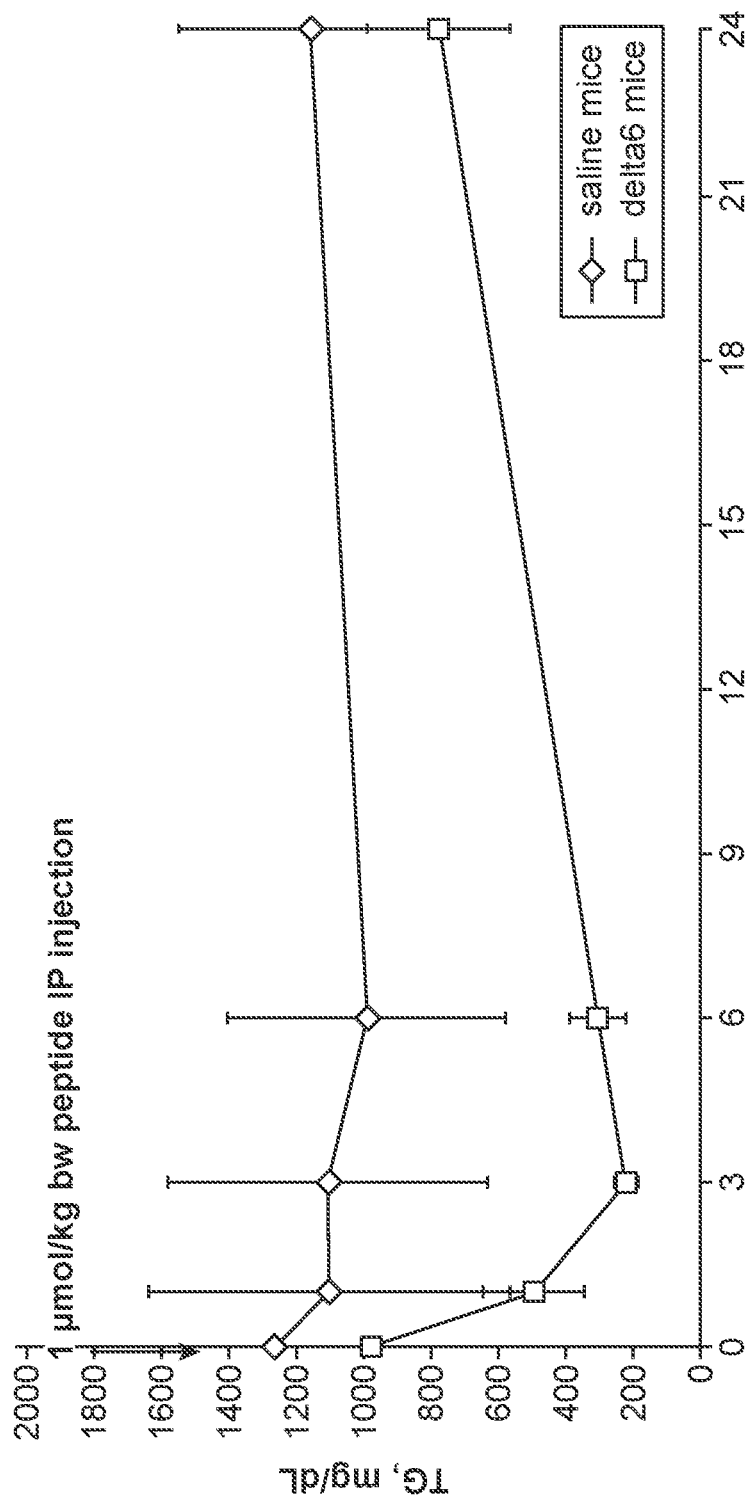
FIG. 21 presents the serum triglyceride (TG) level of apoC-II knockout mice after intraperitoneal injection of apoC-II mimetic peptide Delta6. Saline was used as control.
Figure 22:
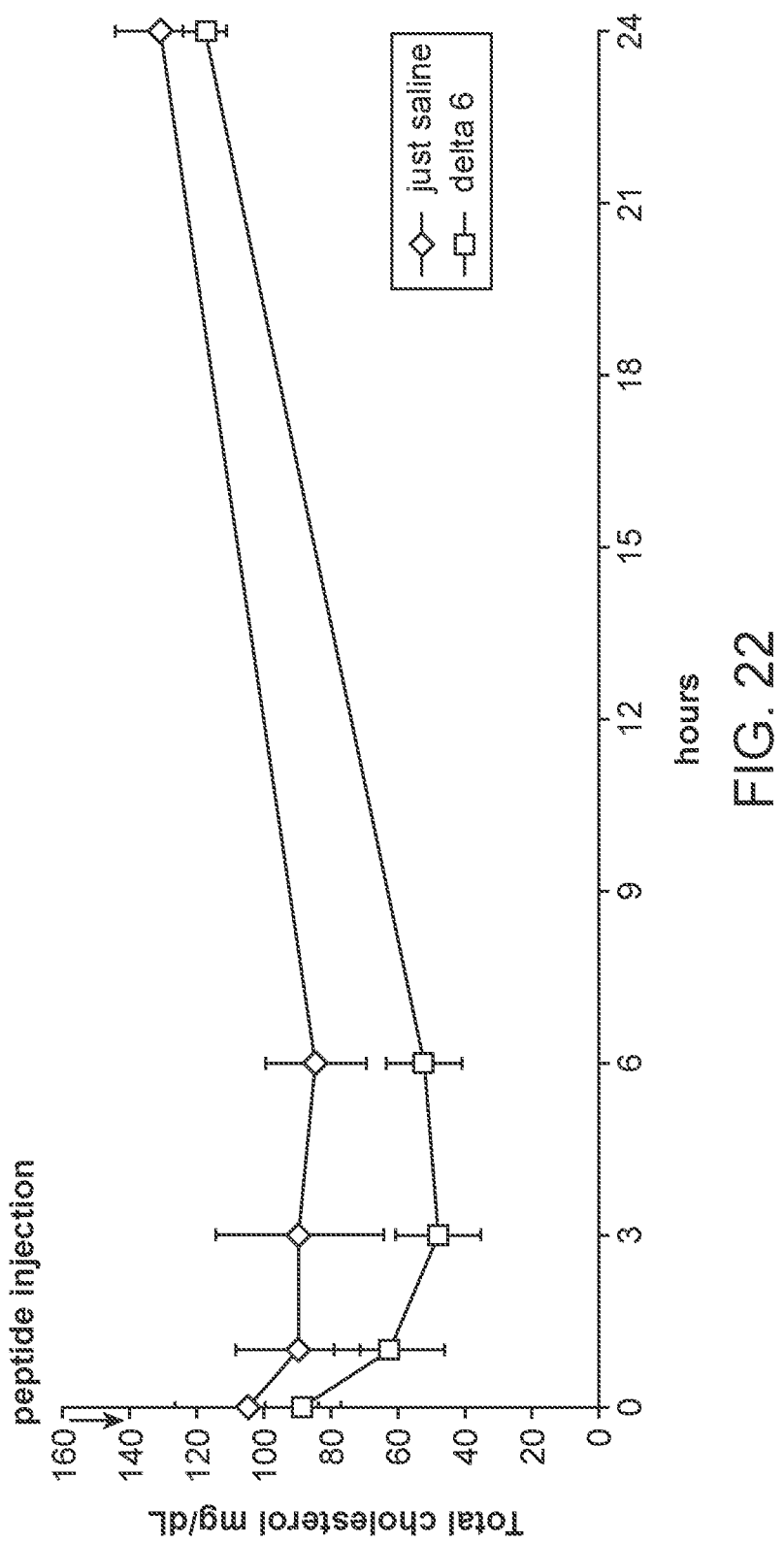
FIG. 22 presents the total cholesterol (TC) level of apoC-II knockout mice after intraperitoneal injection of apoC-II mimetic peptide Delta6. Saline was used as control.

ApoC-II mimetic peptide Delta6 was injected intraperitoneally into apoC-II knockout mice and the plasma lipids were monitored over time (FIG. 21). Injection of Delta6 resulted in a rapid and marked reduction of plasma TG. The intraperitoneal injection of Delta6 also led to a decrease in the total cholesterol level (FIG. 22).

Figure 23:
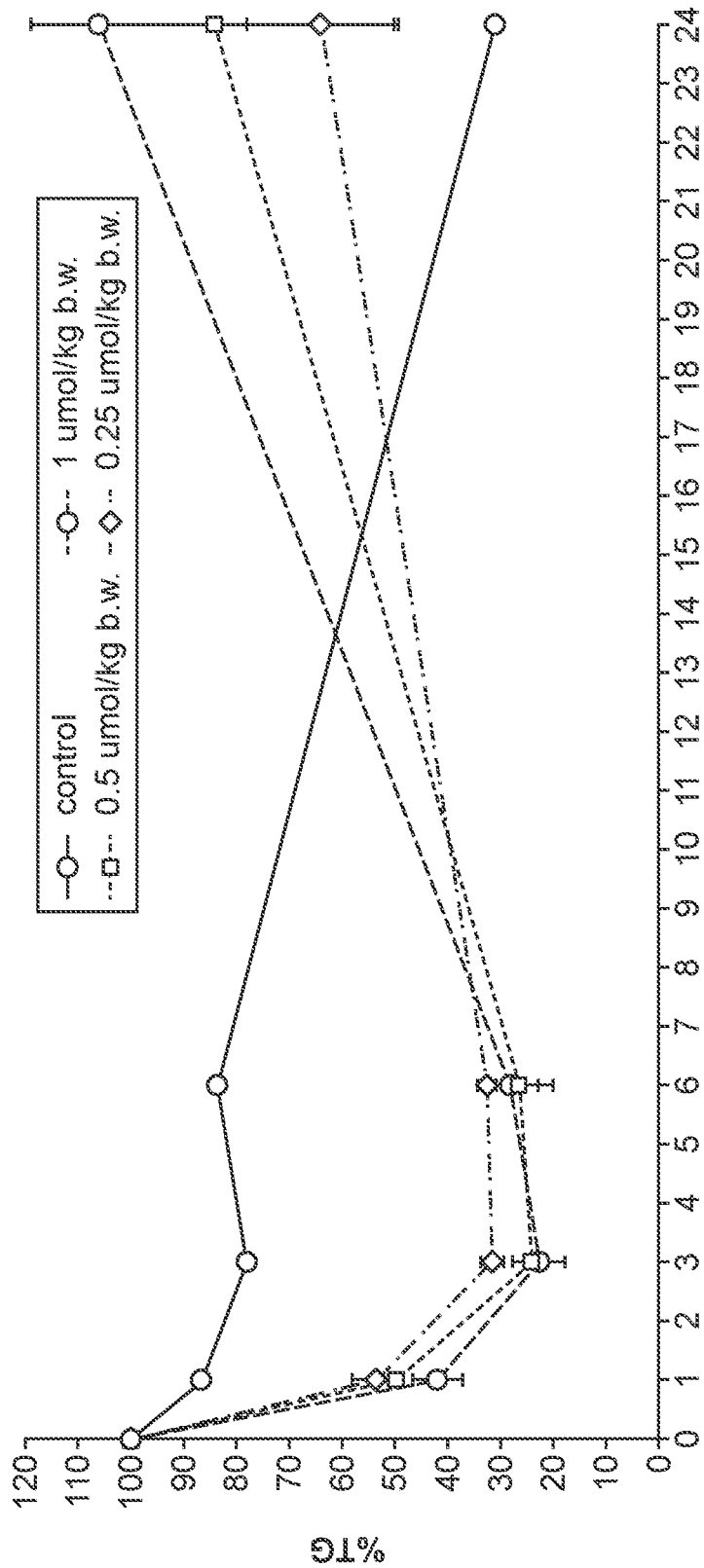
FIG. 23 presents the serum triglyceride (TG) level of apoC-II knockout mice after intraperitoneal injection of different doses of apoC-II mimetic peptide Delta6. Saline was used as control. The percentage of the serum TG level at different time points after the injection compared to the serum TG level at the time of injection was calculated.

As shown in FIG. 23, three different doses of Delta6 peptide (0.25, 0.5, and 1 µmol/kg of body weight) were injected intraperitoneally into apoC-II knockout mice and the plasma TG was monitored over time. All doses of Delta6 led to a rapid and marked reduction of plasma TG.

Figure 24:
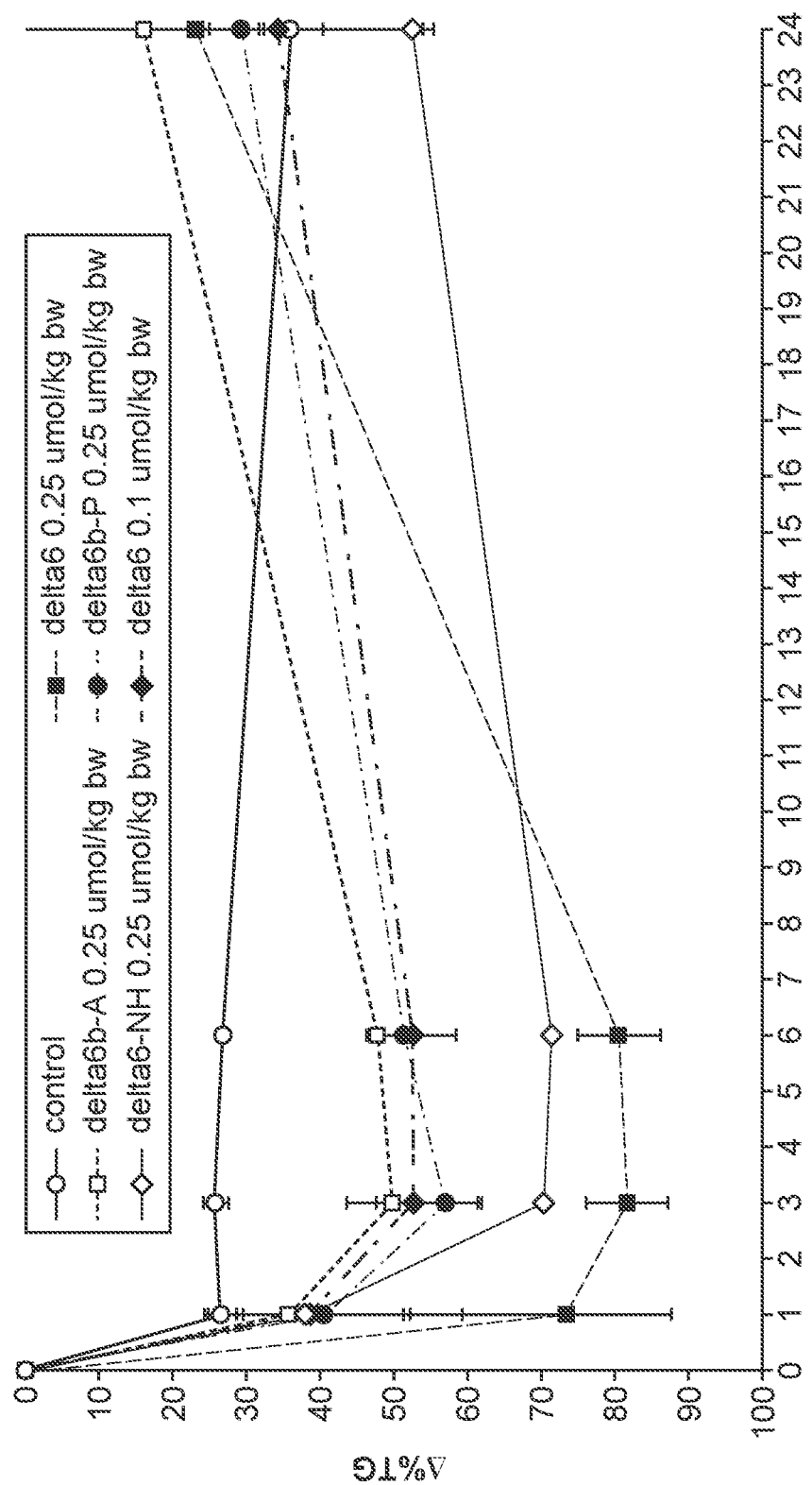
FIG. 24 presents the percentage change of serum triglyceride (TG) of apoC-II knockout mice after intraperitoneal injection of Delta6 variants. Saline was used as control. The percentage change of the serum TG compared to the serum TG at the time of injection was calculated.

Variants of Delta6, Delta6b-A, Delta6b-P, and Delta6-NH were also tested for their ability to enhance in vivo lipolysis at the concentration of 0.25 µmol/kg of body weight. All Delta6 variants resulted in a significant reduction of plasma TG following their intraperitoneal injection in apoC-II knockout mice (FIG. 24).

Figure 53:
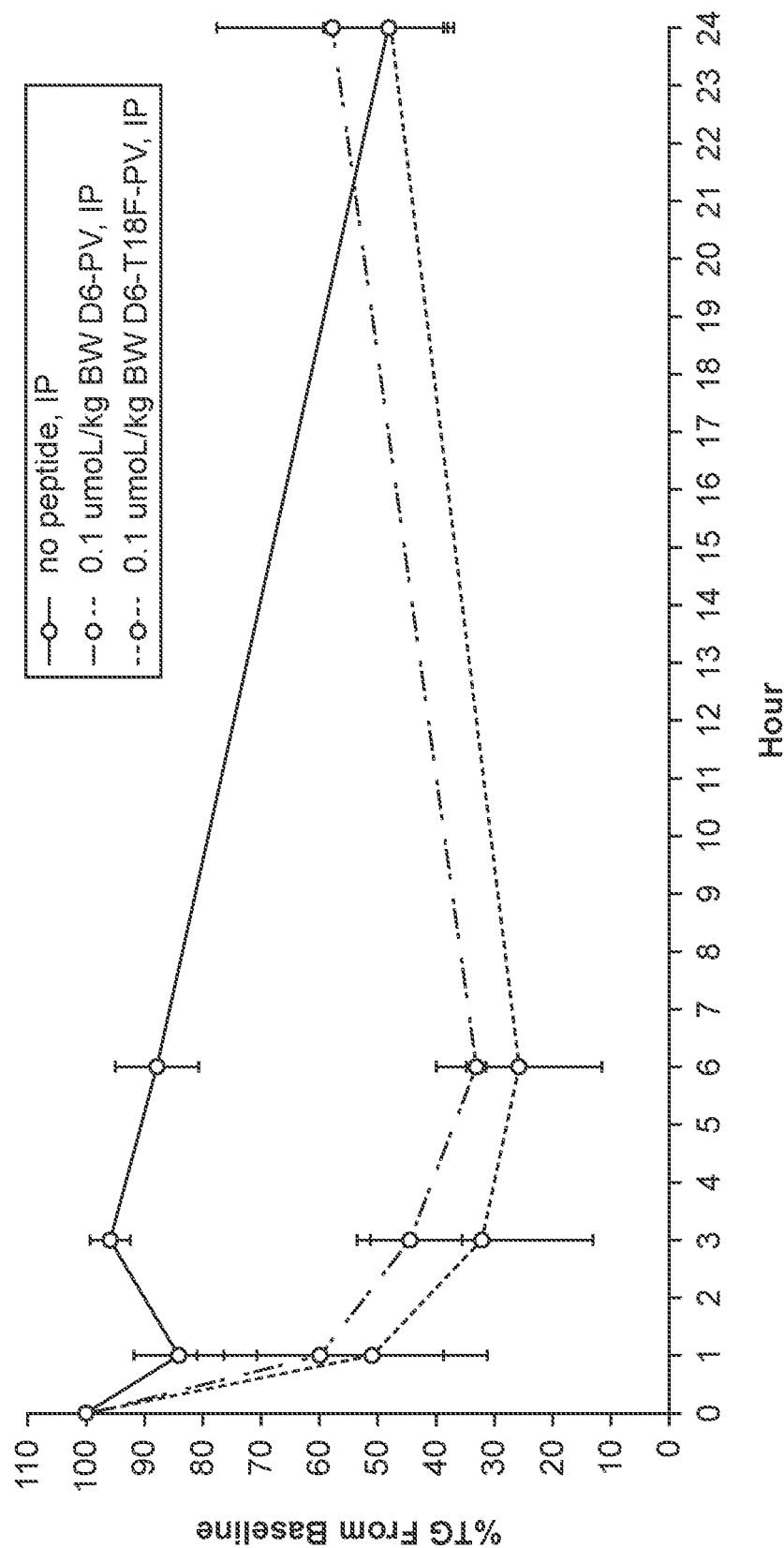
FIG. 53 presents the percentage change of serum TG in apoC-II knockout mice after intraperitoneal injection of Delta6 variants, Delta6PV and Delta6-T18F-PV. Saline was used as control. The percentage change of the serum TG compared to the serum TG at the time of injection was calculated.

As shown in FIG. 53, Delta6 variants Delta6PV and Delta6-T18F-PV were injected intraperitoneally into apoC-II knockout mice at 0.1 µmol/kg of body weight and the plasma TG was monitored over time. Both Delta6PV and Delta6-T18F-PV led to a rapid reduction of plasma TG in the apoC-II knockout mice with a maximum reduction at about 6 hours after the peptide injection.

These results show that apoC-II mimetic peptide Delta6 and its variants have the ability to enhance in vivo lipolysis.

Example 8: ApoC-III Displacement by ApoC-II Mimetic Peptides

ApoC-III is commonly associated with triglyceride rich lipoproteins and has been identified as a potent modulator of plasma TG levels. ApoC-III regulates plasma TG levels through a variety of mechanisms, including suppression of lipoprotein lipase (LPL) activity and LPL-independent effects on TG clearance. We investigated the effect of apoC-II mimetic peptides on displacement of apoC-III.

Figure 25:
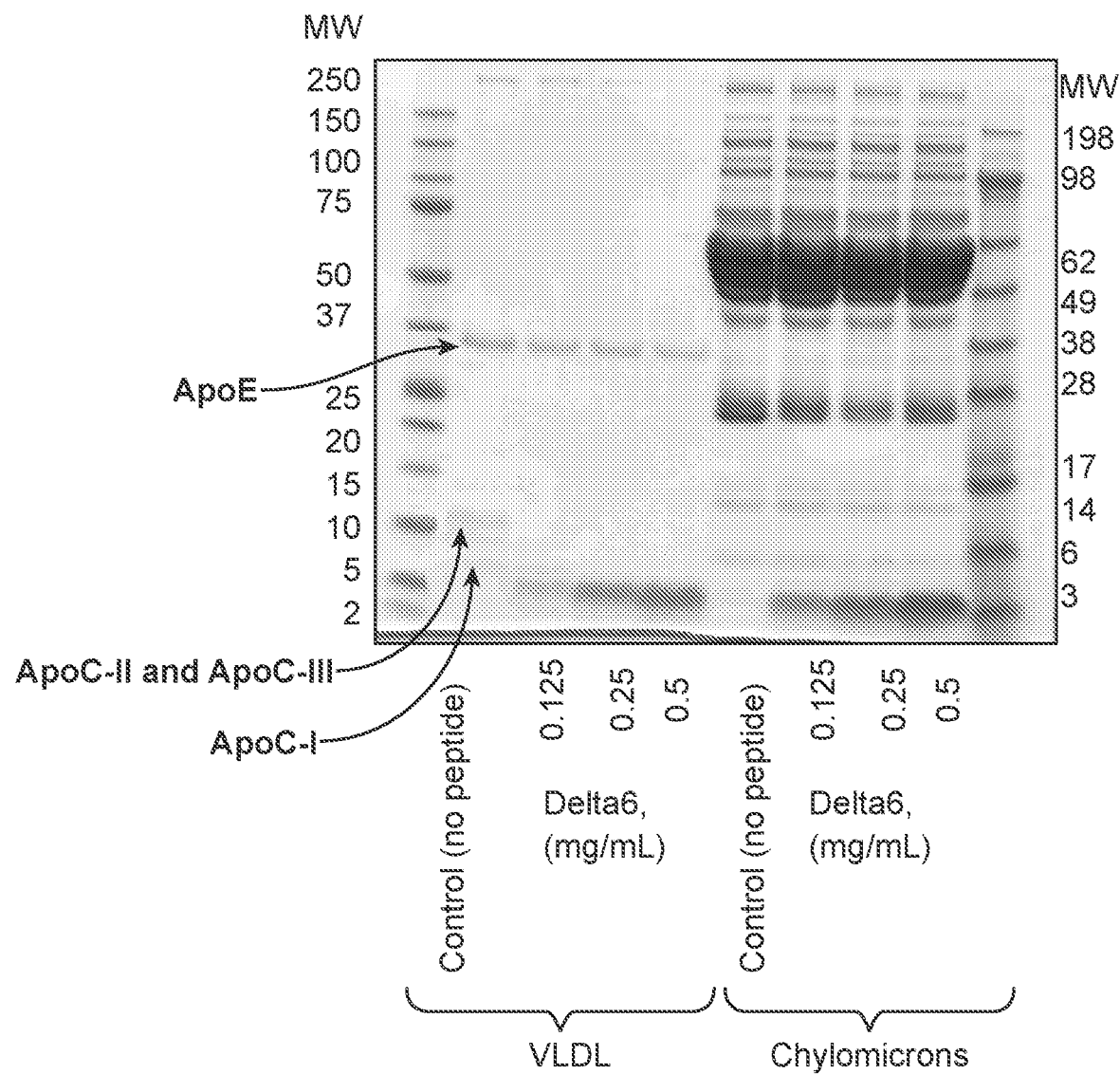
FIG. 25 shows apoC-III displacement by the apoC-II mimetic peptide Delta6 in VLDL and chylomicrons isolated from human plasma.
Figure 26:
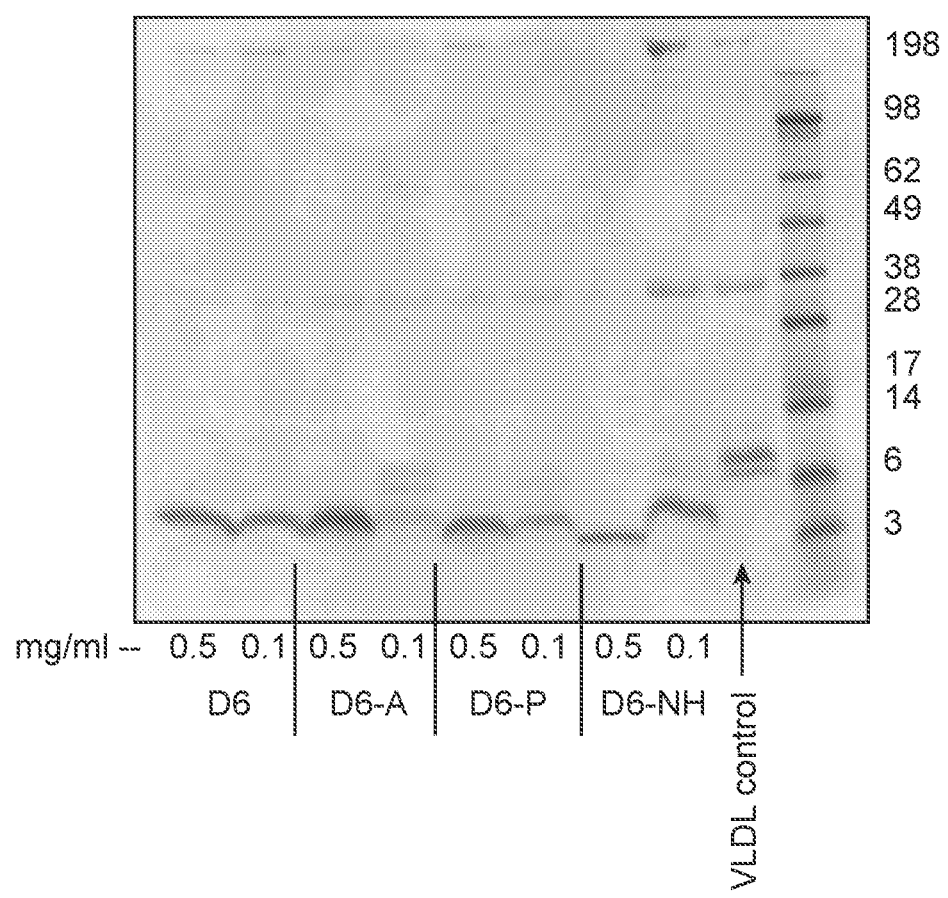
FIG. 26 shows apoC-III displacement by variants of the apoC-II mimetic peptide Delta6 in VLDL isolated from human plasma.

Incubation of VLDL and chylomicrons isolated from human plasma with different concentrations of apoC-II mimetic peptide Delta6 showed that Delta6 had a higher affinity for the VLDL and chylomicrons than the apolipoproteins (FIG. 25). Similarly, incubation of VLDL isolated from human plasma with Delta6 and its derivatives, Delta6-A, Delat6-P, and Delta6-NH, showed that Delta6 and the derivatives were capable of displacing apoC-III (FIG. 26).

Figure 27:
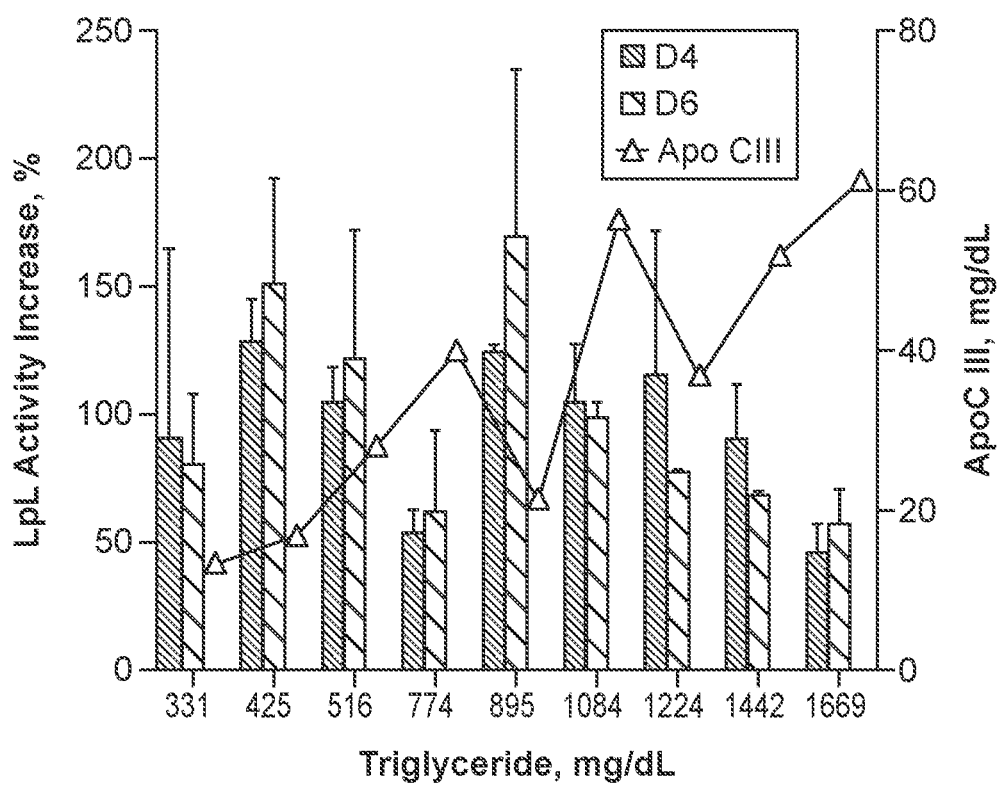
FIG. 27 shows the results of in vitro LPL assay of apoC-II mimetic peptides Delta4 and Delta6 using hypertriglyceridemia patient sera with high apoC-III levels as substrate.

As shown in FIG. 27, in vitro LPL assay was performed with hypertriglyceridemia patient sera. ApoC-II mimetic peptides Delta4 and Delta6 increased the LPL activity in patients with high levels of apoC-III protein.

These results show that apoC-II mimetic peptides Delta4, Delat6 and their variants are capable of displacing apoC-III and enhancing in vitro lipolysis in patient sera with high apoC-III protein.

Example 9: ApoC-III Displacement by ApoC-II-a Peptide

We investigated the effect of apoC-II-a peptide on displacement of apoC-III.

Figure 28:
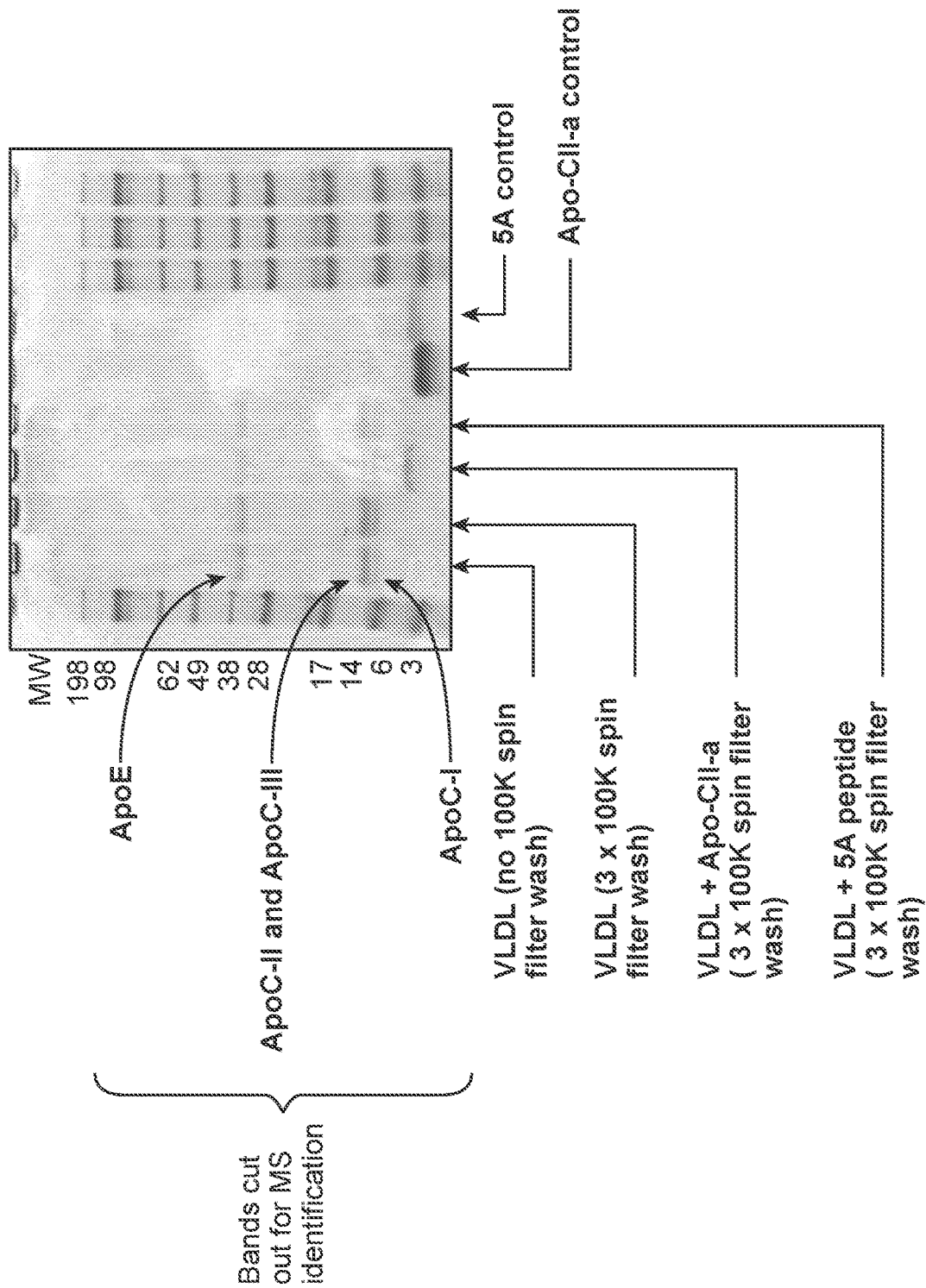
FIG. 28 shows apoC-III displacement by apoC-II-a peptide in VLDL isolated from human plasma (TG=291 mg/dL).

Incubation of VLDL isolated from human plasma with exogenous apoC-II-a peptide showed that apoC-II-a has a higher affinity for the VLDL than the apolipoproteins (FIG. 28). MALDI-TOF mass spectrometry analysis showed that apoC-II-a peptide selectively replaced apoC-III and apoC-I, but not apoC-II (FIG. 29A). Interestingly, the binding of the apoC-II-a peptide to VLDL is almost proportional to its concentration (FIG. 29B).

Figure 30:
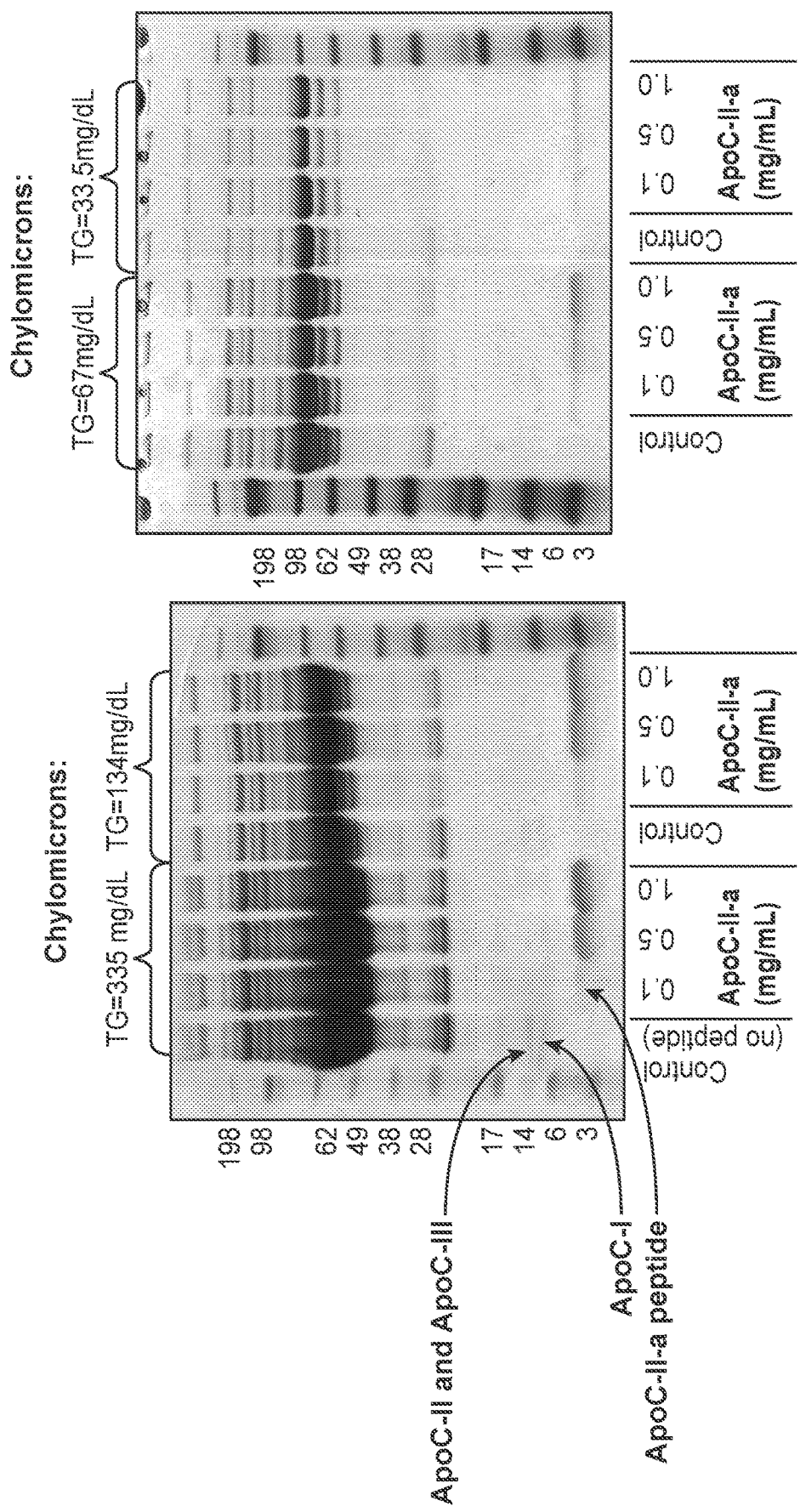
FIG. 30 shows apoC-III displacement by apoC-II-a peptide in chylomicrons isolated from human plasma.

Incubation of chylomicrons isolated from human plasma with exogenous apoC-II-a peptide showed that apoC-II-a has a higher affinity for chylomicrons than the apolipoproteins (FIG. 30).

Figure 31:
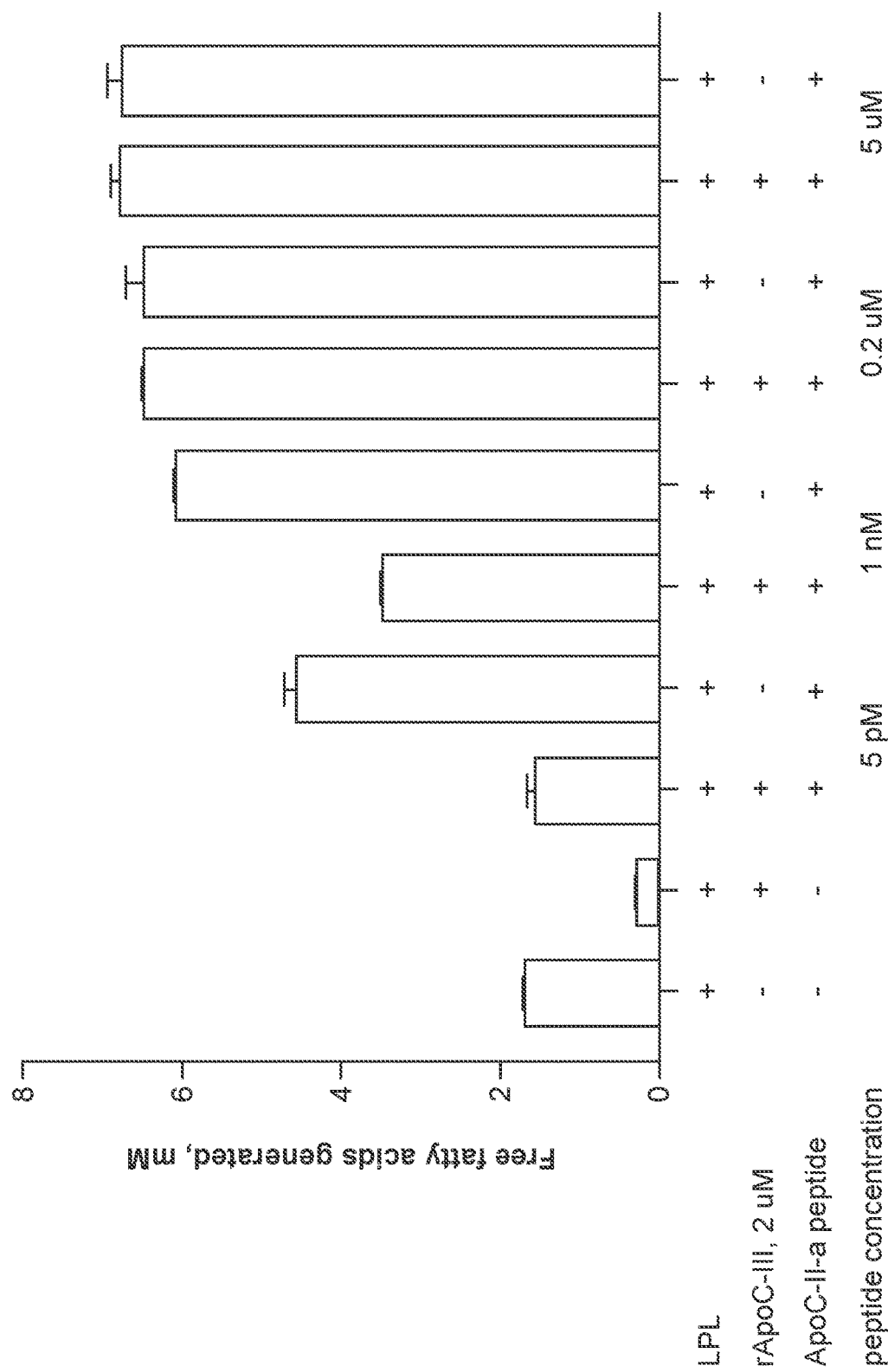
FIG. 31 presents results from an LPL activation assay with Intralipid as substrate and recombinant apoC-III as an inhibitor. ApoC-II-a peptide overcomes the inhibition by apoC-III.

LPL assay was performed using Intralipid as a substrate. As shown in FIG. 31, apoC-III inhibited the production of free fatty acid (NEFA). Addition of apoC-II-a peptide overcame the inhibitory effect of apoC-III and facilitated lipolysis in a dose-dependent manner.

Figure 32:
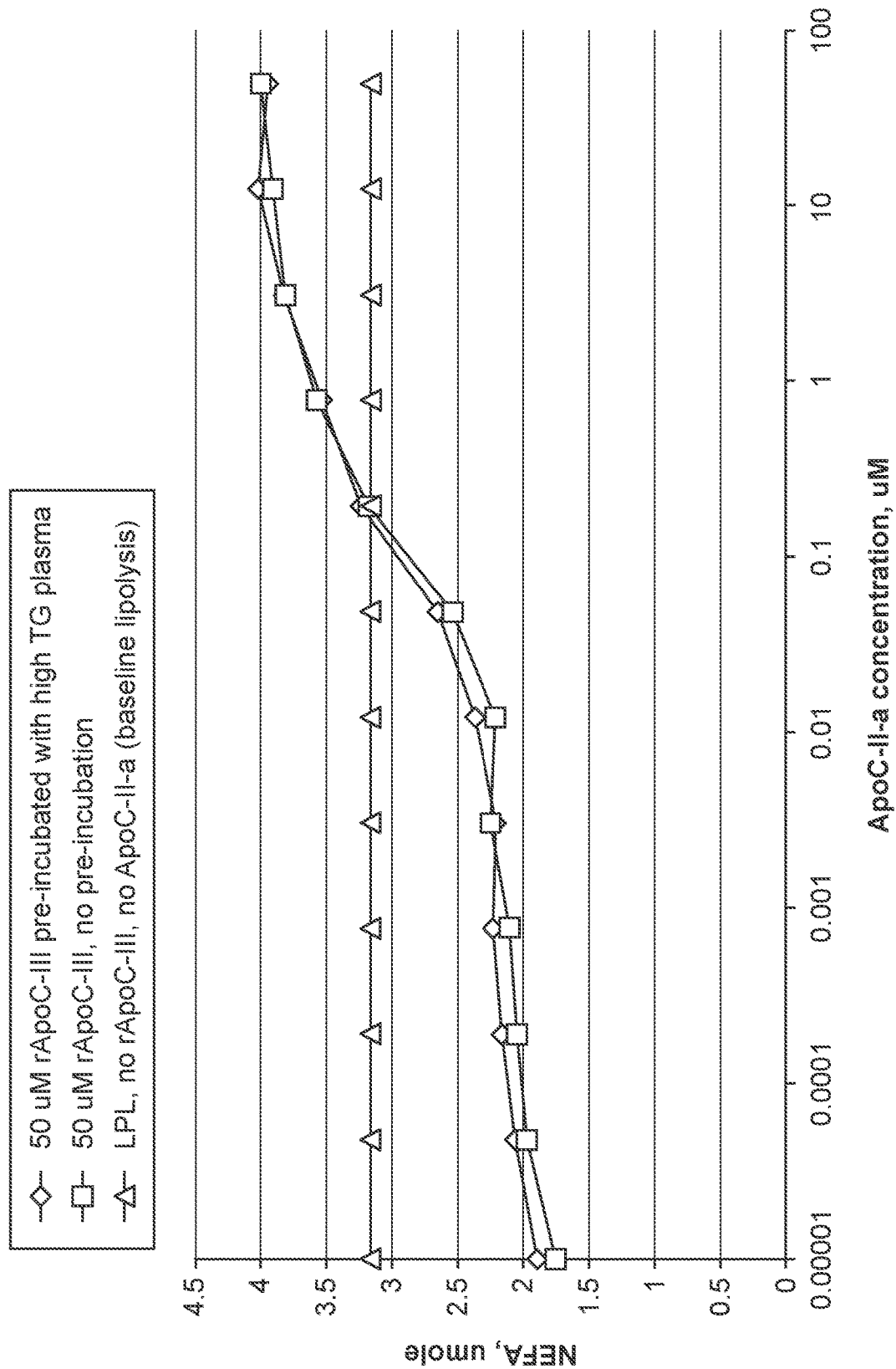
FIG. 32 presents results from an LPL activation assay with high TG human plasma as substrate and recombinant apoC-III as an inhibitor. ApoC-II-a peptide overcomes the inhibition by apoC-III.

LPL assay was also performed using high TG human plasma as a substrate in a 1:50 dilution. The results are shown on FIG. 32. When 50 µM apoC-III recombinant protein was added, the free fatty acid (NEFA) production dropped from about 3.2 µM to about 1.7 µM. ApoC-II-a peptide was added in various concentrations. At a concentration of 0.01 µM, it started to affect lipolysis. At a concentration of about 0.2 µM, it overcame the inhibitory effect of apoC-III. Higher concentrations of apoC-II-a further facilitated lipolysis. Pre-incubation of apoC-III with human plasma did not change the effect of apoC-II-a peptide.

Figure 33:
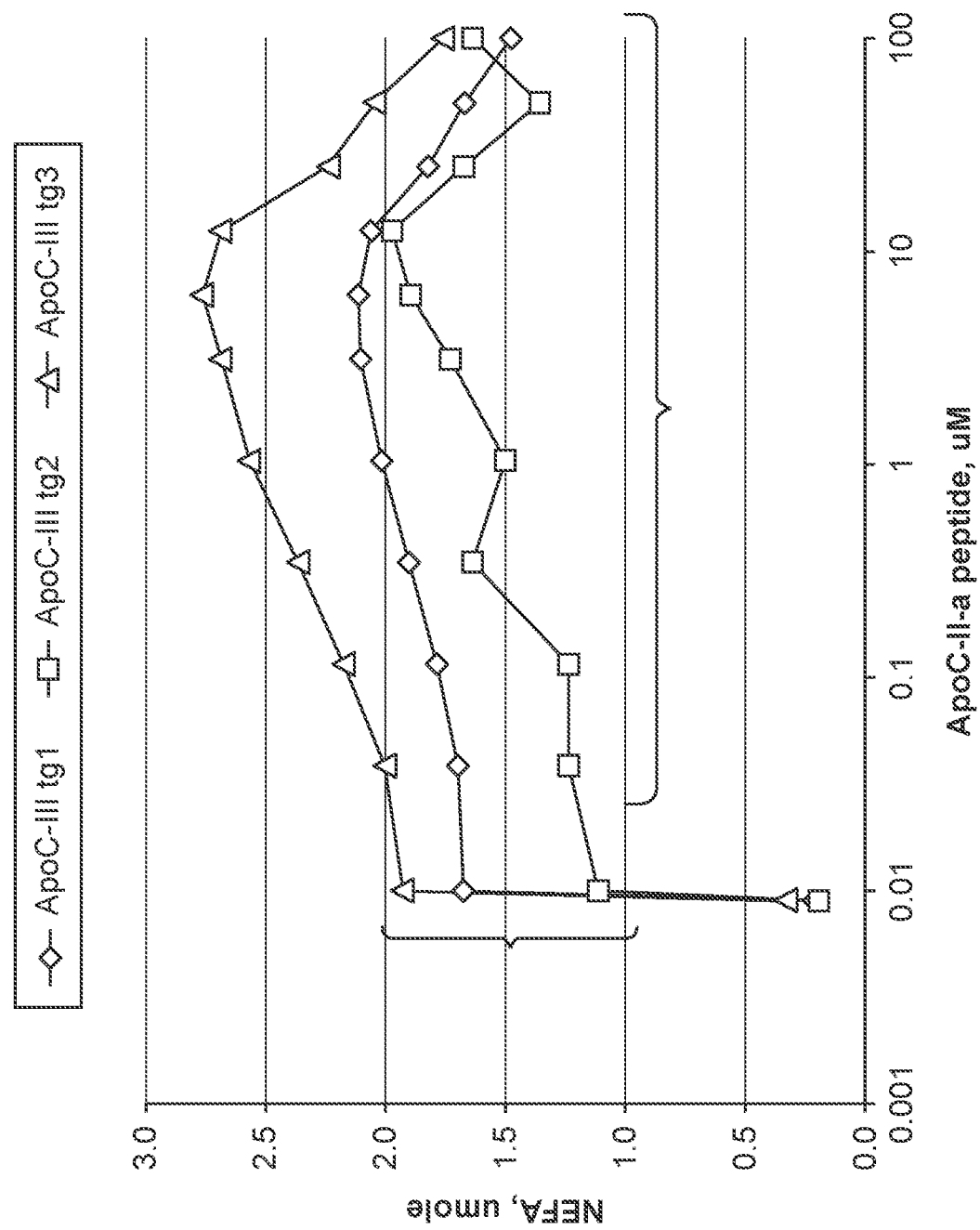
FIG. 33 graphs results from an LPL activation assay using apoC-III transgenic (tg) mice plasma as substrate. The TG concentrations of ApoC-III tg1, tg2, and ApoC-III tg3 mice are 323 mg/dL, 497 mg/dL, and 478 mg/dL, respectively. ApoC-II-a peptide overcomes the inhibitory effect of elevated expression of apoC-III in all three transgenic mice plasma samples.

We also tested plasma from transgenic mice over-expressing human apoC-III. The apoC-III in the plasma suppressed lipolysis, consistent with the known ability of high concentrations of apoC-III to cause hypertriglyceridemia. In the LPL assay using the plasma from apoC-III transgenic mice, apoC-II-a peptide overcame the inhibitory effect of elevated expression of apoC-III in all three transgenic mice plasma samples (FIG. 33).

Example 10: ApoC-II-a Blunts Post-Prandial Hypertriglyceridemia in Mice by Mechanisms Additional to Lipoprotein Lipase Activation Post-prandial hypertriglyceridemia is an important cardiovascular disease (CVD) risk factor. We recently described an apoC-II mimetic peptide (apoC-II-a) that activates LPL and lowers serum TG in apoC-II-KO mice. To investigate apoC-II-a as a therapy for post-prandial hypertriglyceridemia, we investigated its effect on several mouse models after a fat challenge test.

Figure 34A:
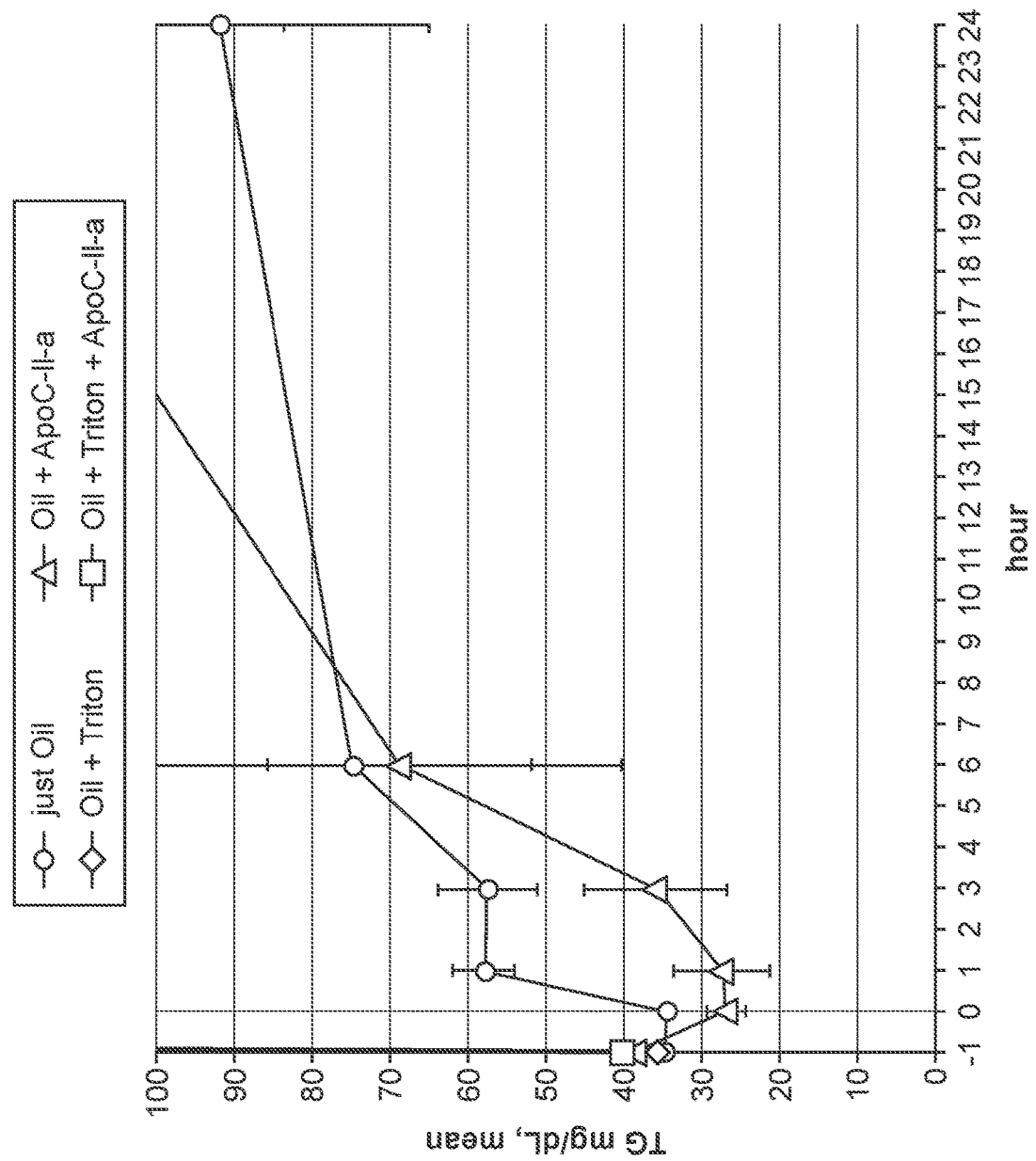
FIG. 34A and FIG. 34B show 24 hour serum post-prandial TG levels in mice after an oral gavage with vegetable oil in the presence or absence of the LPL inhibitor Triton WR1339, and in the presence or absence of apoC-II-a peptide, with FIG. 34A focusing on the TG concentration range of 0-100 mg/dL, and FIG. 34B showing the TG concentration range of 0-4500 mg/dL.
Figure 34B:
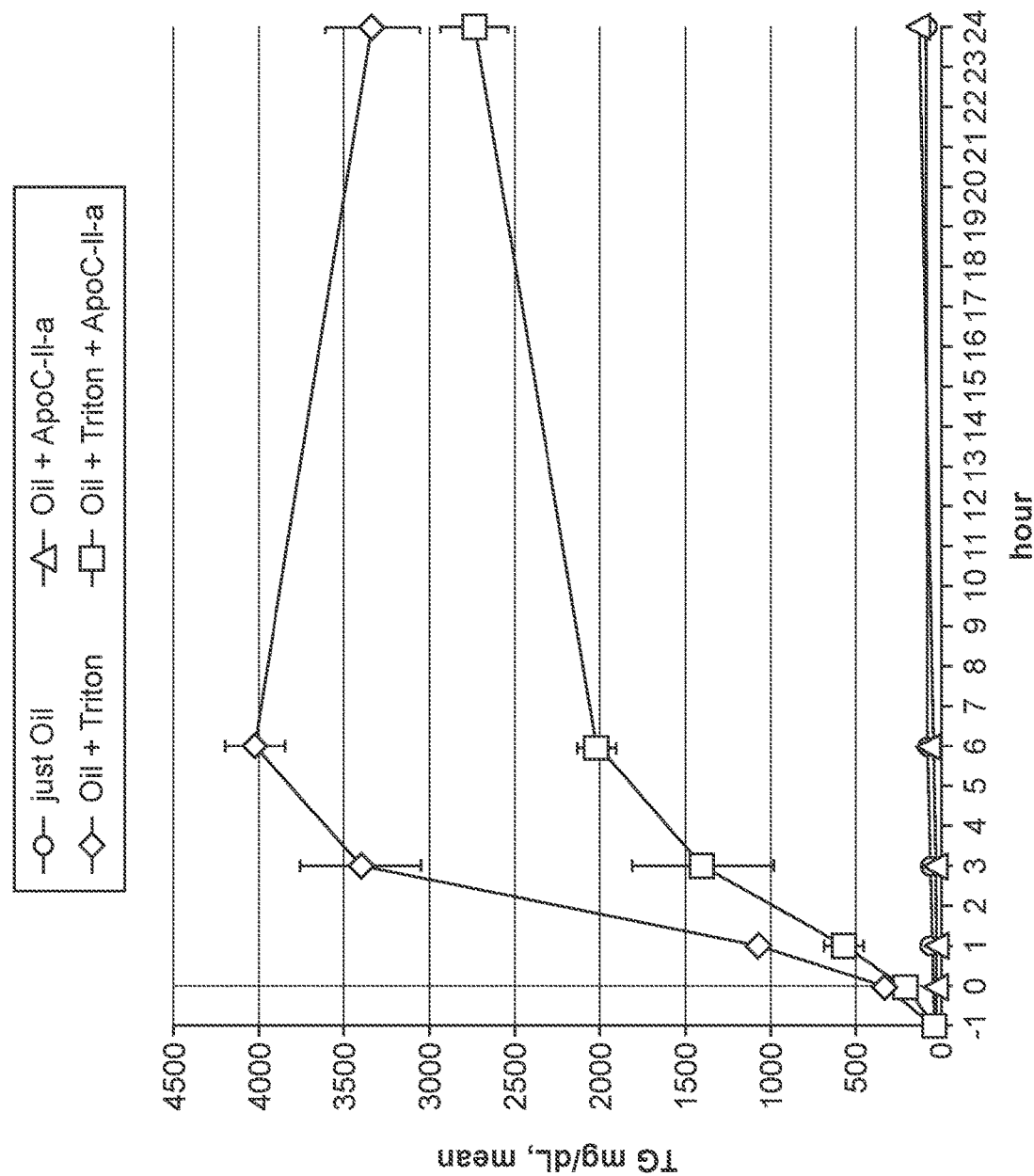

After an oral gavage with vegetable oil (10 µL/gram), serum TG increased by 3 h in C57BL/6 mice by at least 5-fold but when mice were injected 30 min before gavage with apoC-II-a (1 µmoL/kg; IP or SQ), the post-prandial TG rise was almost completely blunted. The post-prandial TG level in mice serum is shown in FIGS. 34A and 34B. Similar results were found in apoE-KO mice, indicating that the effect of apoC-II-a is independent of apoE (not shown). ApoC-II-a did not appear to work at the level of TG absorption, because it also rapidly accelerated serum clearance of TG after IP injection of 20% Intralipid. Addition of exogenous LPL to serum samples collected after IP injection with Intralipid revealed that lipoprotein particles from mice treated with apoC-II-a were better substrates for LPL.

The rise in serum TG after IP injection of Intralipid was only partially blocked by about 50% when mice were co-injected with the LPL inhibitor Triton WR1339, indicating that apoC-II-a works additionally by an LPL-independent mechanism. FIGS. 34A and 34B show the comparison of the post-prandial TG in mice serum with or without the Triton co-injection. Incubation of human serum with exogenous apoC-II-a at doses comparable to that achieved in vivo in mice showed that apoC-II-a binds to all lipoproteins, including HDL and causes the displacement of apoC-I and apoC-III. Furthermore, the in vitro inhibition of LPL from the addition of exogenous apoC-III could be overcome by adding apoC-II-a at a molar ratio of at least 1:10 compared to apoC-III.

In summary, the apoC-II-a mimetic peptide at relatively low doses can accelerate the clearance of post-prandial TG after a fat load. It does so in part by activating LPL, as expected. Unexpectedly, however, we found that apoC-II-a also reduces triglyceride levels by relieving the inhibition of LPL by apoC-III, and possibly also by blocking the other known LPL-independent effects of apoC-III, and possibly apoC-I, in delaying the post-prandial clearance of TG.

Example 11: Delta6PV Enhanced In Vivo Lipolysis in Mouse Models (Single-Dose Studies)

The effect of the Delta6PV peptide on in vivo lipolysis was investigated in wild type, apoC-II knockout, and apoC-III transgenic mice with single-dose studies.

Figure 35A:
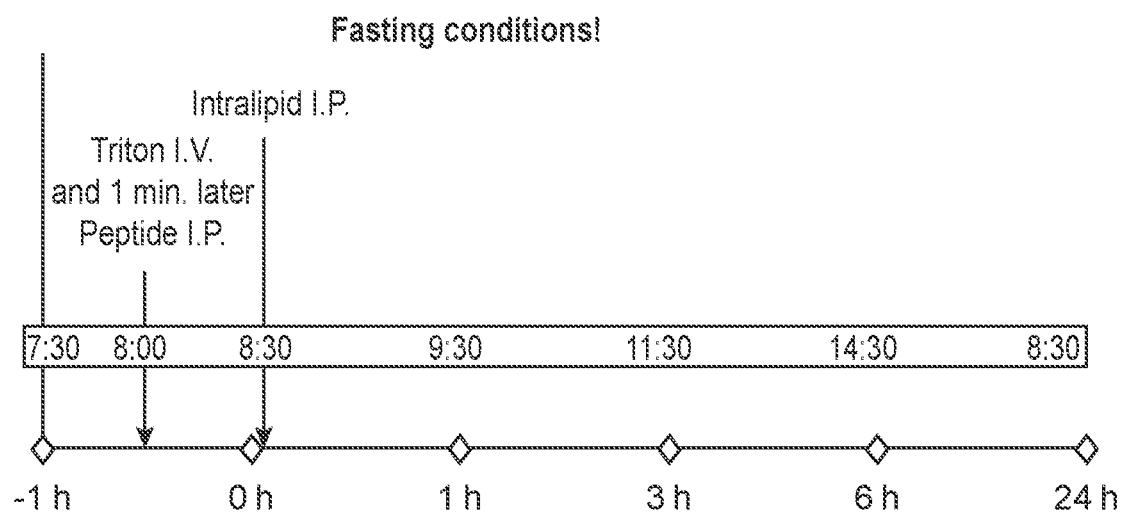
FIG. 35A and FIG. 35B show the percentage change of serum TG level of wild-type mice after Intralipid injection with or without the intraperitoneal injection of the Delta6PV peptide in the presence or absence of the LPL inhibitor Triton, with FIG. 35A showing the timeline of injection and FIG. 35B showing the percentage change of serum TG level after intraperitoneal injection of Delta6PV in the presence or absence of Triton. Saline was used as control.
Figure 35B:
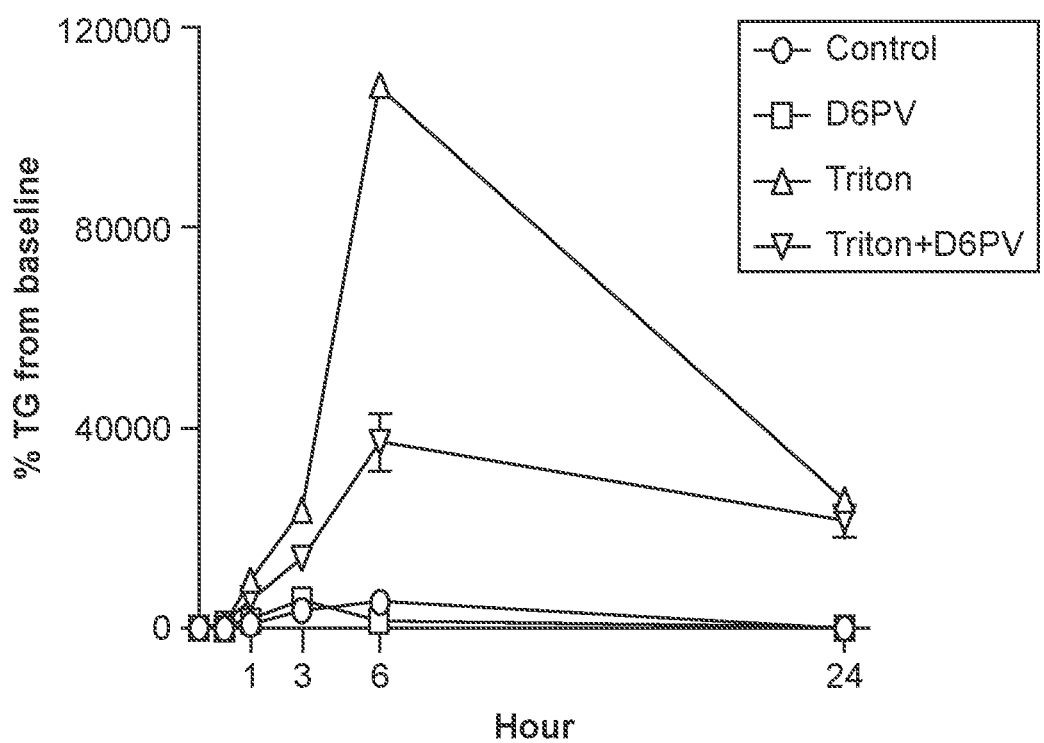

After an intraperitoneal injection of Intralipid, serum TG increased significantly in wild-type mice. Co-injection of LPL inhibitor Triton further increased the serum TG level to more than 1000-fold at the 6 h time point. When mice were intraperitoneally injected with the apoC-II mimetic peptide Delta6PV, the TG increase was significantly reduced (FIG. 35B). Delta6PV peptide reversed the inhibition of LPL by Triton.

The apoC-II mimetic peptide Delta6PV was injected intraperitoneally (FIG. 36B) or subcutaneously (FIG. 36C) into apoC-II knockout mice and the plasma TG level was monitored over time. Injection of Delta6PV resulted in a rapid and marked reduction of plasma TG.

Figure 37A:
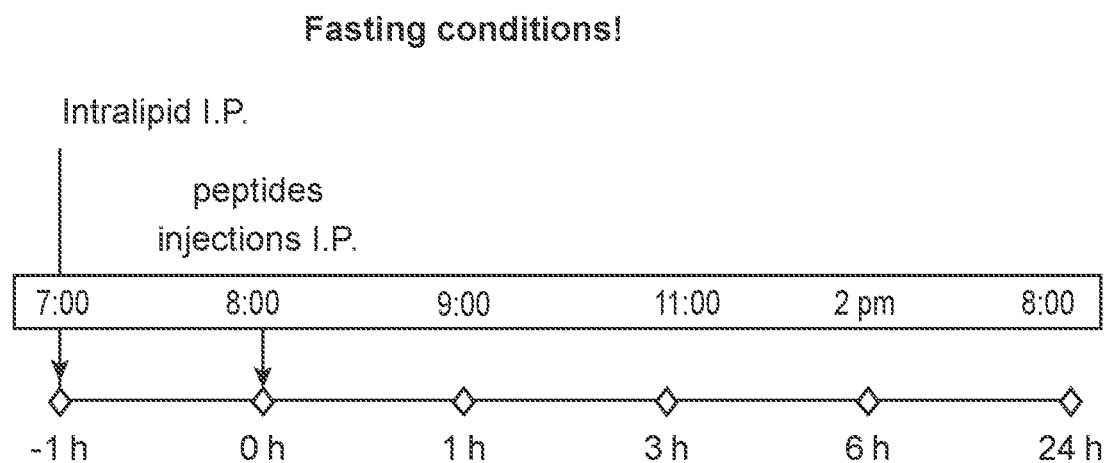
FIG. 37A and FIG. 37B show the percentage change of serum TG level of apoC-II knockout mice after Intralipid injection with or without the intraperitoneal injection of Delta6PV peptide, with FIG. 37A showing the timeline of injection and FIG. 37B showing the percentage change of serum TG level after intraperitoneal injection of Delta6PV at 5 µmole/kg and 10 µmole/kg (B. W.). Saline was used as control.
Figure 37B:
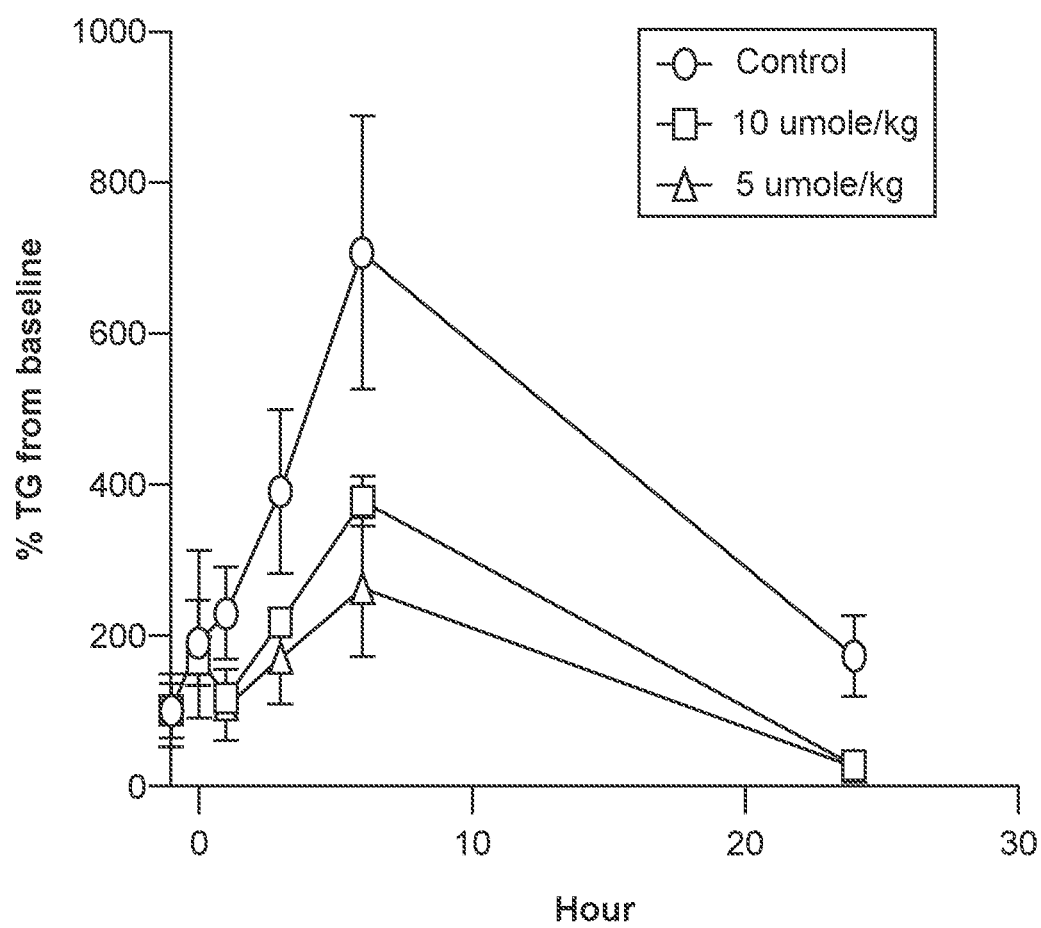

After an intraperitoneal injection with Intralipid, serum TG increased in apoC-II knockout mice by about 7-fold 6 hours after the injection. When mice were intraperitoneally injected with the Delta6PV peptide 1 hour after the injection of Intralipid, the TG increase was significantly reduced (FIG. 37B).

Figure 38A:
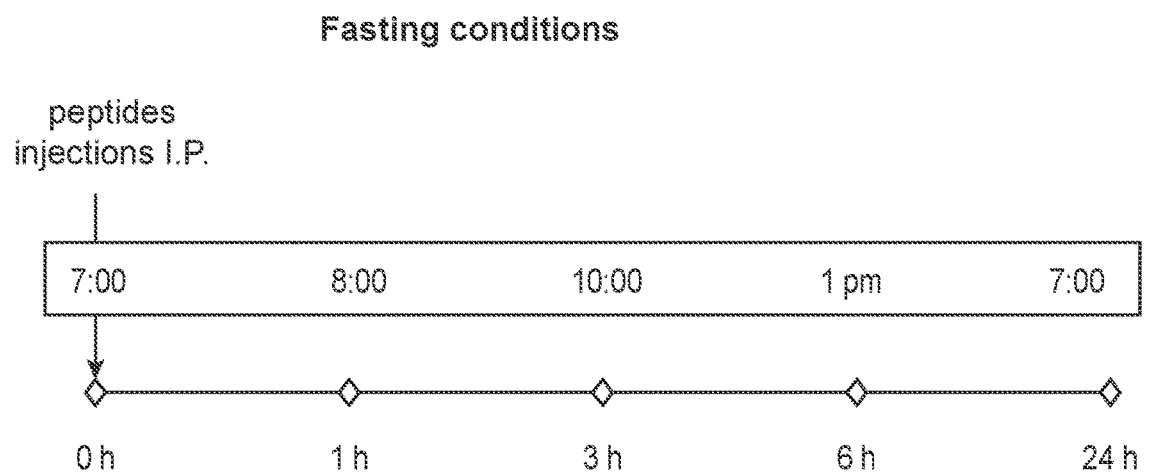
FIG. 38A, and FIG. 38B show the percentage change of serum TG level of apoC-III transgenic mice after injection of apoC-II mimetic peptide Delta6PV, with FIG. 38A showing the timeline of injection, FIG. 38B showing the percentage change of serum TG level after intraperitoneal injection of Delta6PV at 1 µmole/kg, 5 µmole/kg, and 10 µmole/kg (B. W.). Saline was used as control.
Figure 38B:
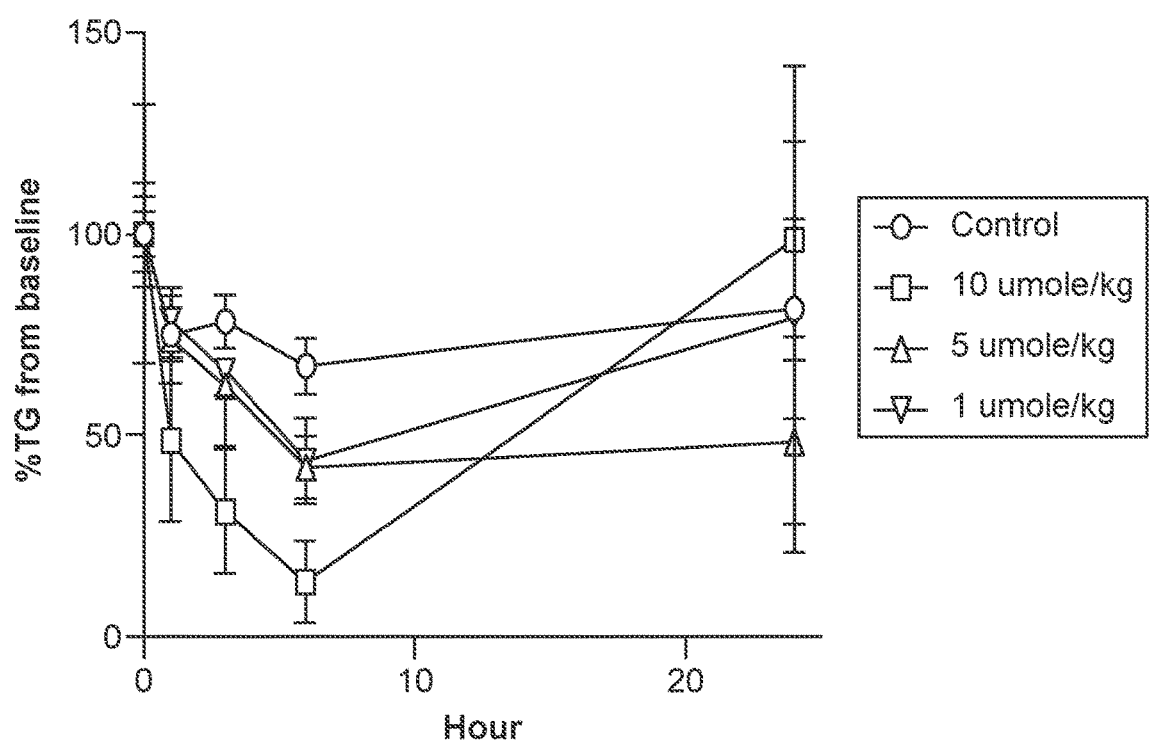

The Delta6PV peptide was injected intraperitoneally into apoC-III transgenic mice and the plasma TG level was monitored over time. Injection of Delta6PV resulted in a rapid and marked reduction of plasma TG with a maximum decrease after about 6 hours after the injection (FIG. 38B).

Figure 39:
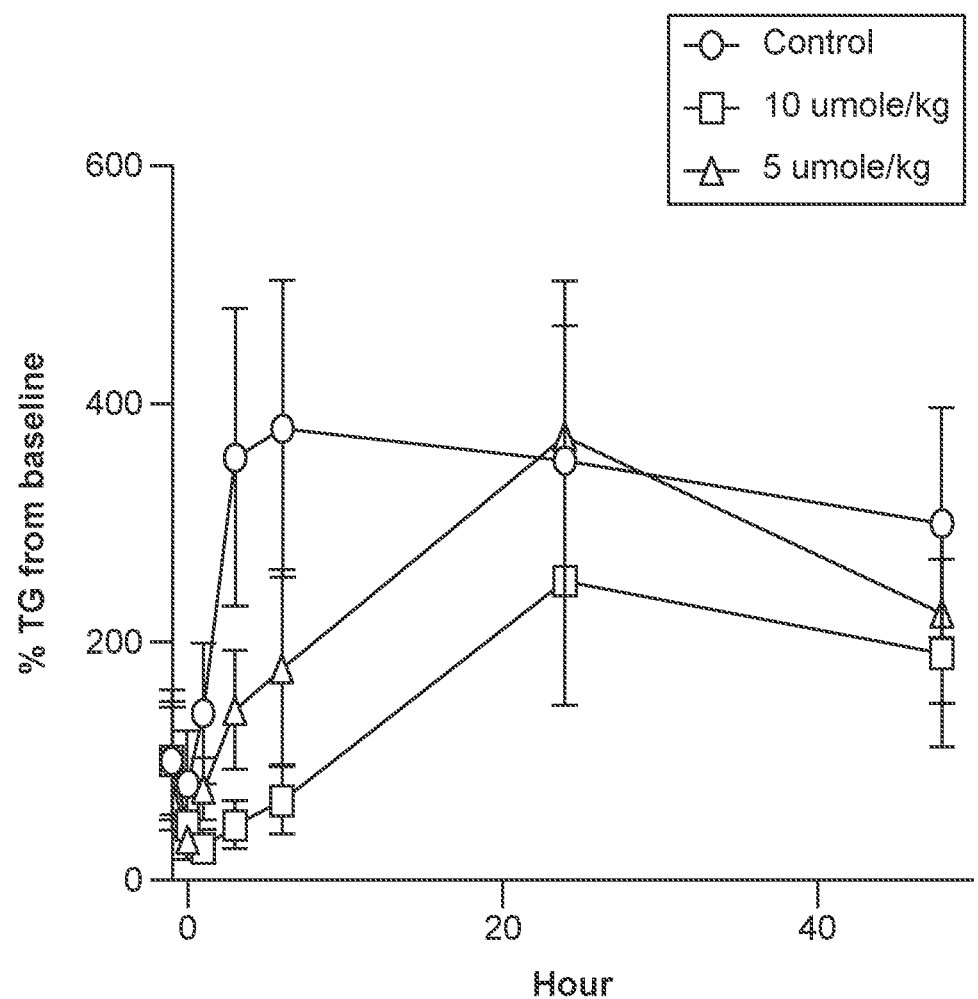
FIG. 39 shows the percentage change of serum TG level of apoC-III transgenic mice after Intralipid injection with or without the intraperitoneal injection of Delta6PV peptide at 5 µmole/kg and 10 µmole/kg (B. W.). Saline was used as control.

After an intraperitoneal injection with Intralipid, serum TG increased in apoC-III transgenic mice by about 4-fold 6 hours after the injection. When mice were intraperitoneally injected with the Delta6PV peptide 1 hour after the injection of Intralipid, the TG increase was significantly reduced (FIG. 39).

The single-dose studies show that the apoC-II mimetic peptide Delta6PV has the ability to enhance in vivo lipolysis in mouse models.

Example 12: Delta6PV Enhanced In Vivo Lipolysis in Mouse Models (Repeat-Dose Studies)

Wild-type mice, apoC-II knockout mice, and apoC-III transgenic mice were injected with the apoC-II mimetic peptide Delta6PV multiple times by intraperitoneal injection.

Figure 40:
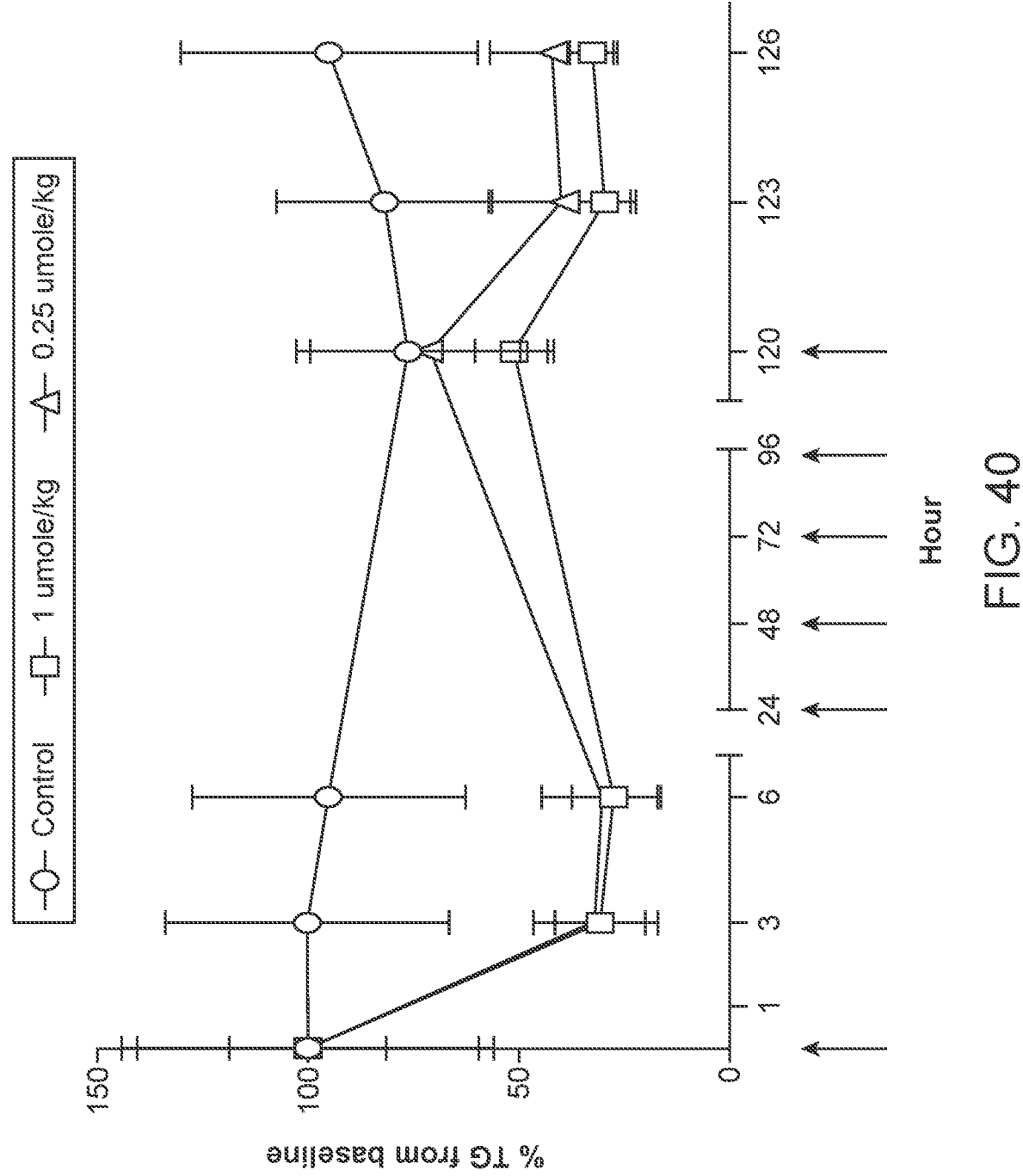
FIG. 40 shows the percentage change of serum TG level of apoC-II knockout mice after multiple injections of apoC-III mimetic peptide Delta6PV at 0.25 µmole/kg and 1 µmole/kg (B. W.). The arrows indicate the time points of Delta6PV injection. Saline was used as control.
Figure 41:
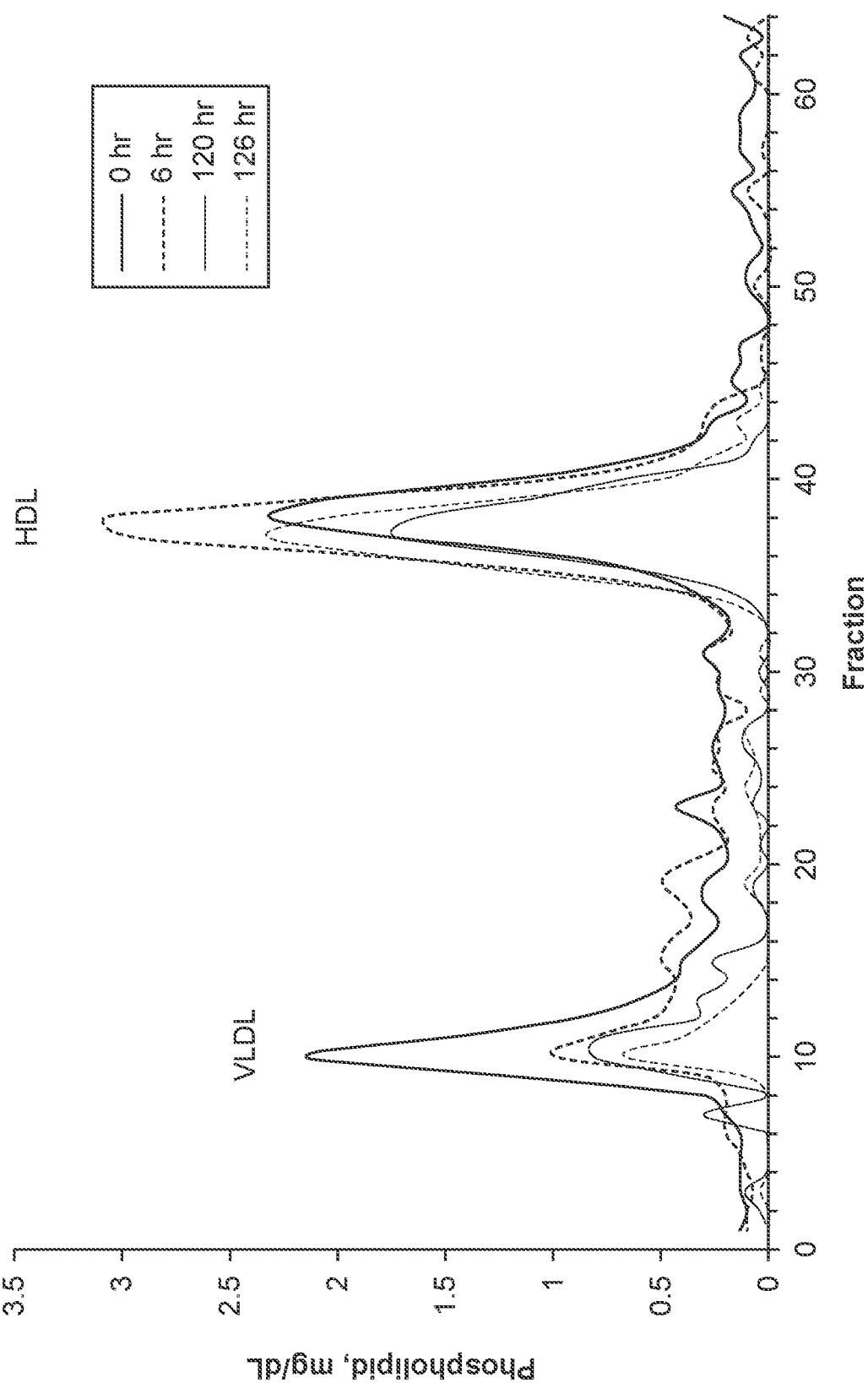
FIG. 41 presents the results of SEC-FPLC separation of various lipid fractions in the 1 µmole/kg (B. W.) Delta6PV administered apoC-II knockout mice. The level of lipoprotein particles is represented by phospholipid.
Figure 42:
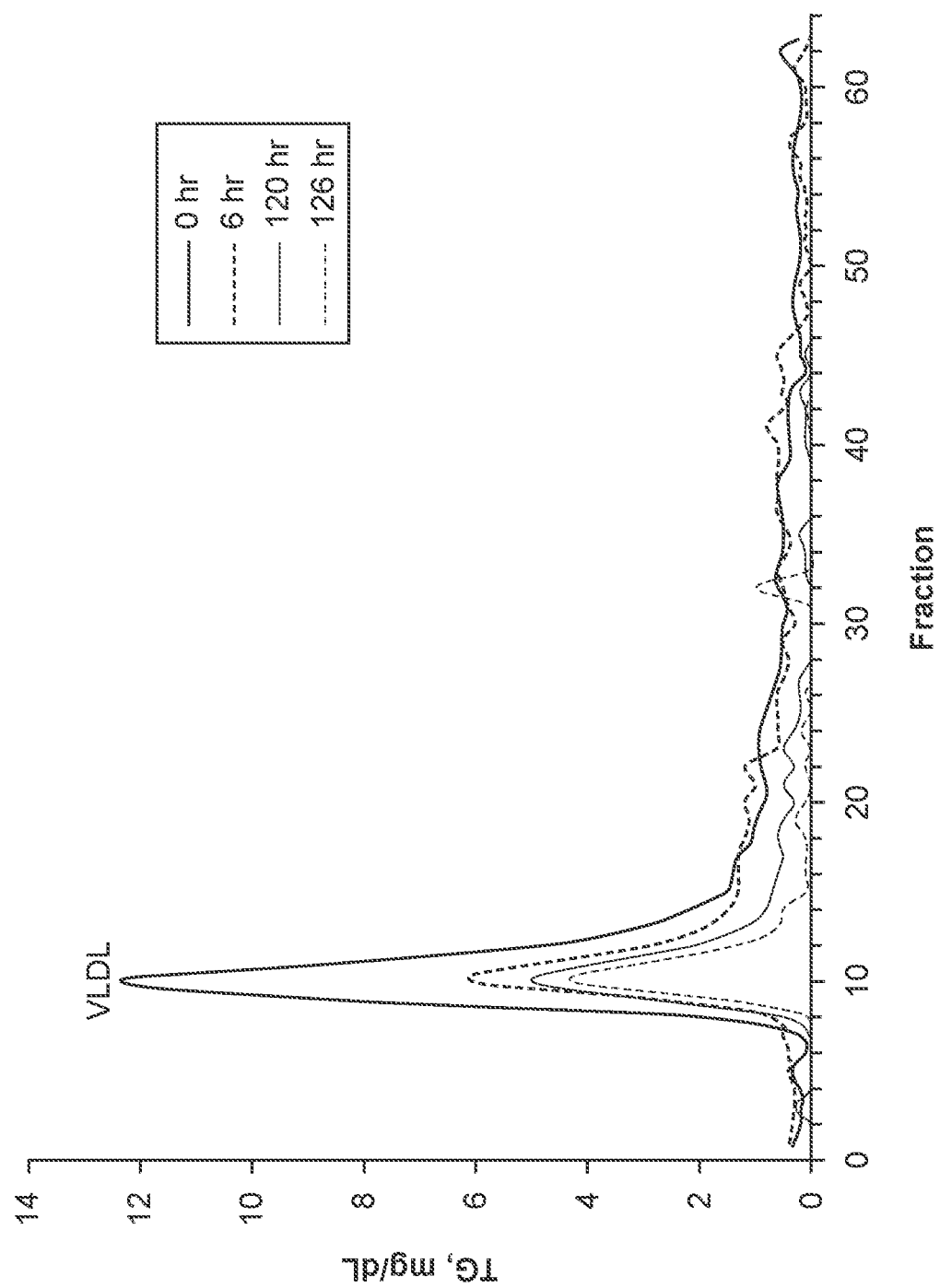
FIG. 42 presents the results of SEC-FPLC separation of various lipid fractions in the 1 µmole/kg Delta6PV administered apoC-II knockout mice. The level of lipoprotein particles is represented by TG.

The Delta6PV peptide was injected intraperitoneally into apoC-II knockout mice at 24 h intervals for 6 days and the plasma TG level was measured at 0 h, 3 h and 6 h on Day 1 and 0 h, 3 h, and 6 h on Day 6. Repeat injection of Delta6PV resulted in a marked and lasting reduction of plasma TG (FIG. 40). SEC-FPLC (size exclusion chromatography—fast protein liquid chromatography) were run on the pooled plasma samples of 0 h and 6 h on Day 1 and 0 h and 6 h on Day 6 from mice treated with Delta6PV peptide at 1 µmole/kg (B. W.). As shown in FIG. 41, the level VLDL decreased 6 hours after injection of the Delta6PV peptide, while the level of HDL increased, as measured by the phospholipid level. The level of TG also decreased in the VLDL pool (FIG. 42).

Figures 43A, 43B:
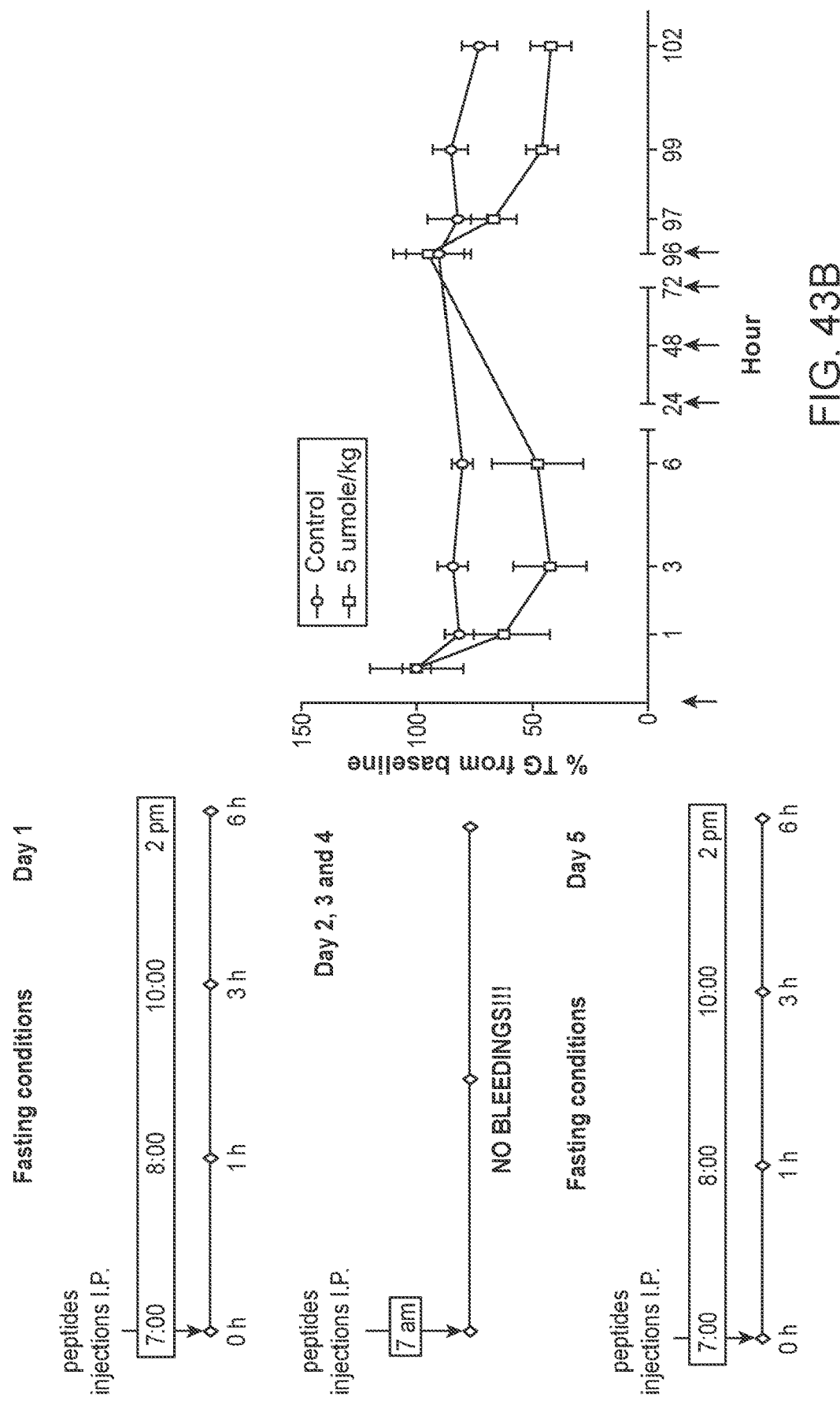
FIG. 43A and FIG. 43B show the percentage change of serum TG level of apoC-III transgenic mice after multiple injections of apoC-II mimetic peptide Delta6PV, with FIG. 43A showing the timeline of injections and FIG. 43B showing the percentage change of serum TG level after intraperitoneal injection of Delta6PV at 5 µmole/kg (B. W.). The arrows indicate the time points of Delta6PV injection. Saline was used as control.
Figure 44:
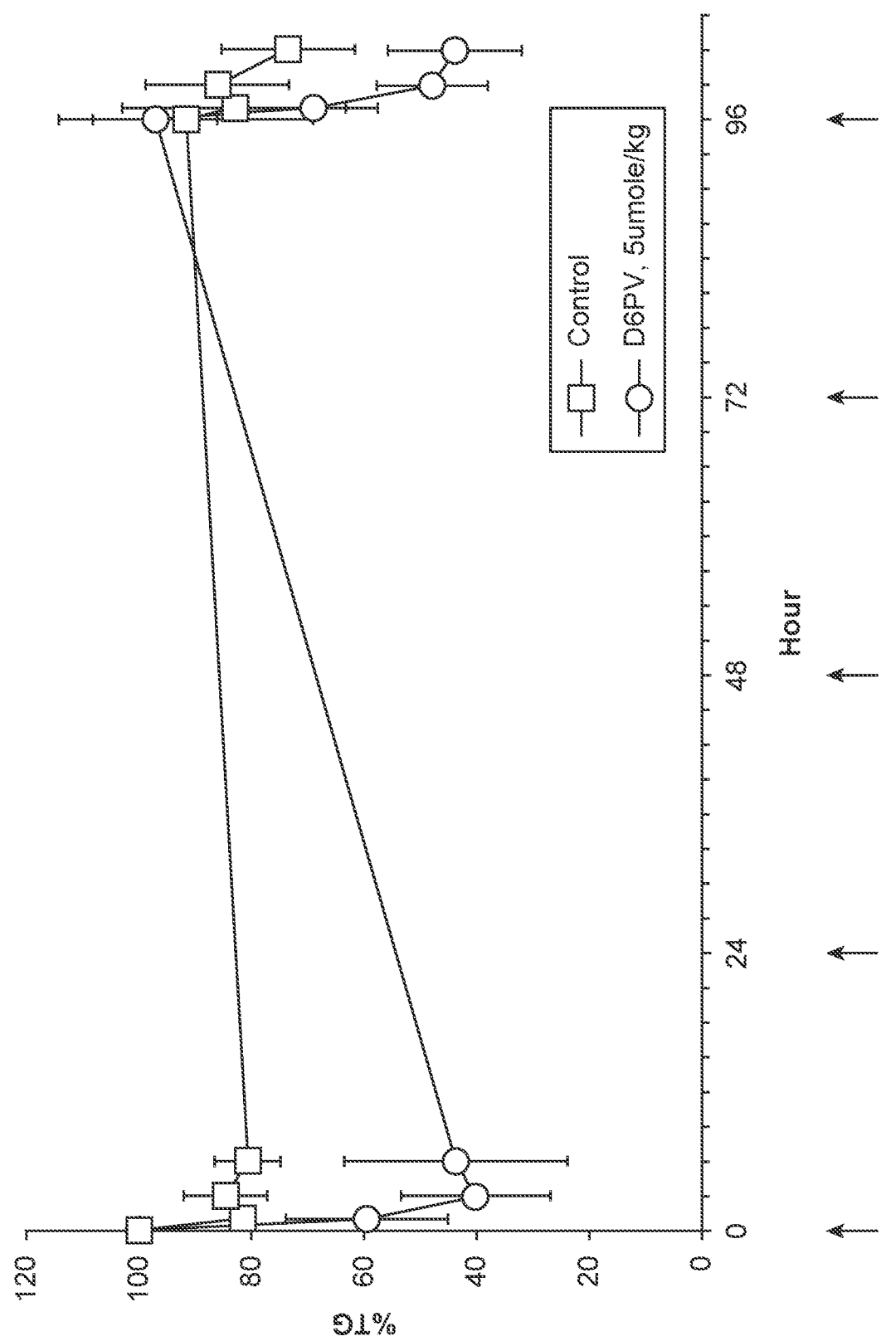
FIG. 44 shows the percentage change of serum TG level of apoC-III transgenic mice after multiple injections of apoC-II mimetic peptide Delta6PV at 5 µmole/kg (B. W.). The arrows indicate the time points of Delta6PV injection. Saline was used as control.
Figure 45A:
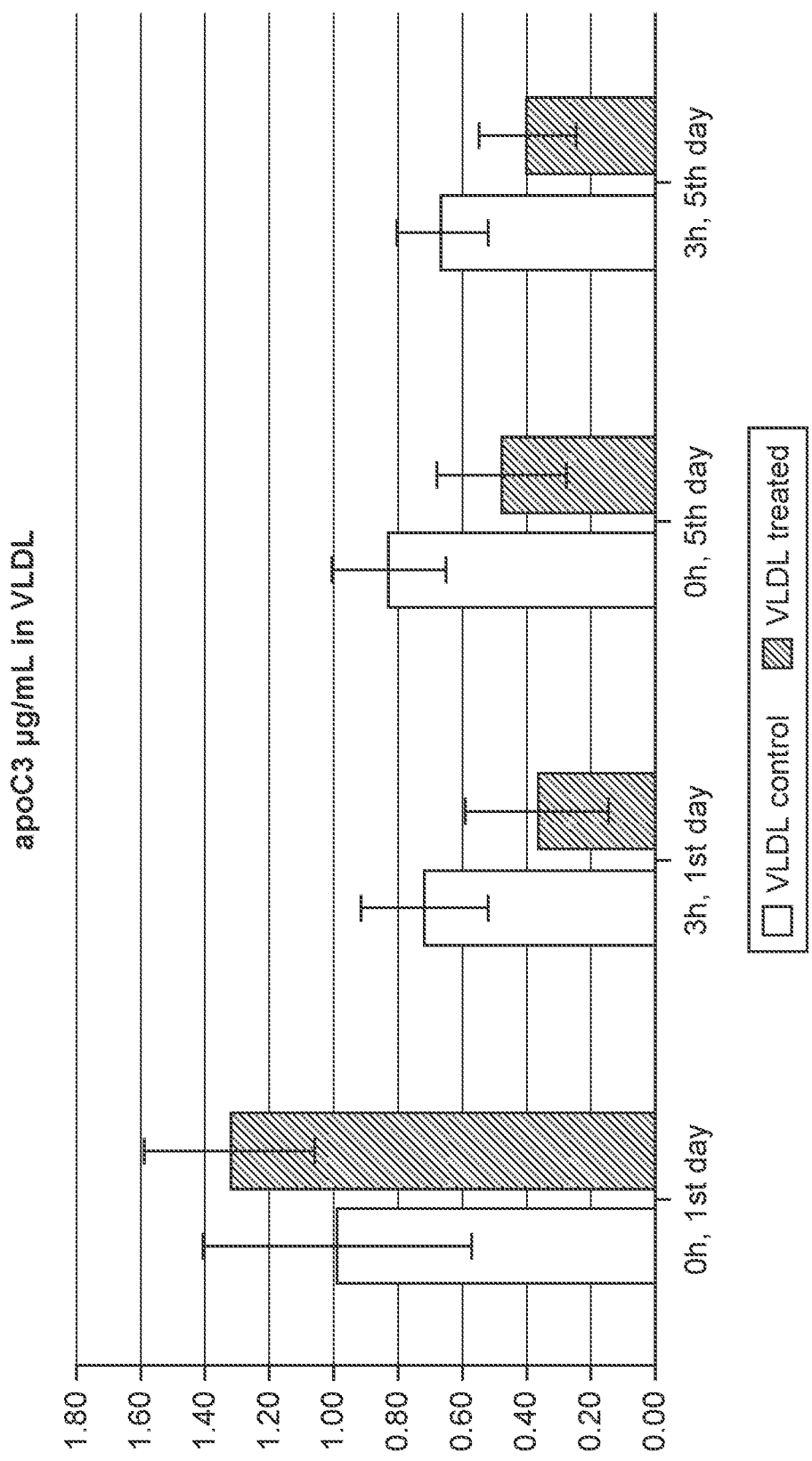
FIG. 45A and FIG. 45B show the apoC-III level after Delta6PV injections in apoC-III mice, as measured by ELISA, with FIG. 45A showing the apoC-III level in VLDL particles on Day 1 and Day 5 before and 3 hours after injection and FIG. 45B showing the apoC-III level in HDL particles on Day 1 and Day 5 before and 3 hours after injection.
Figure 45B:
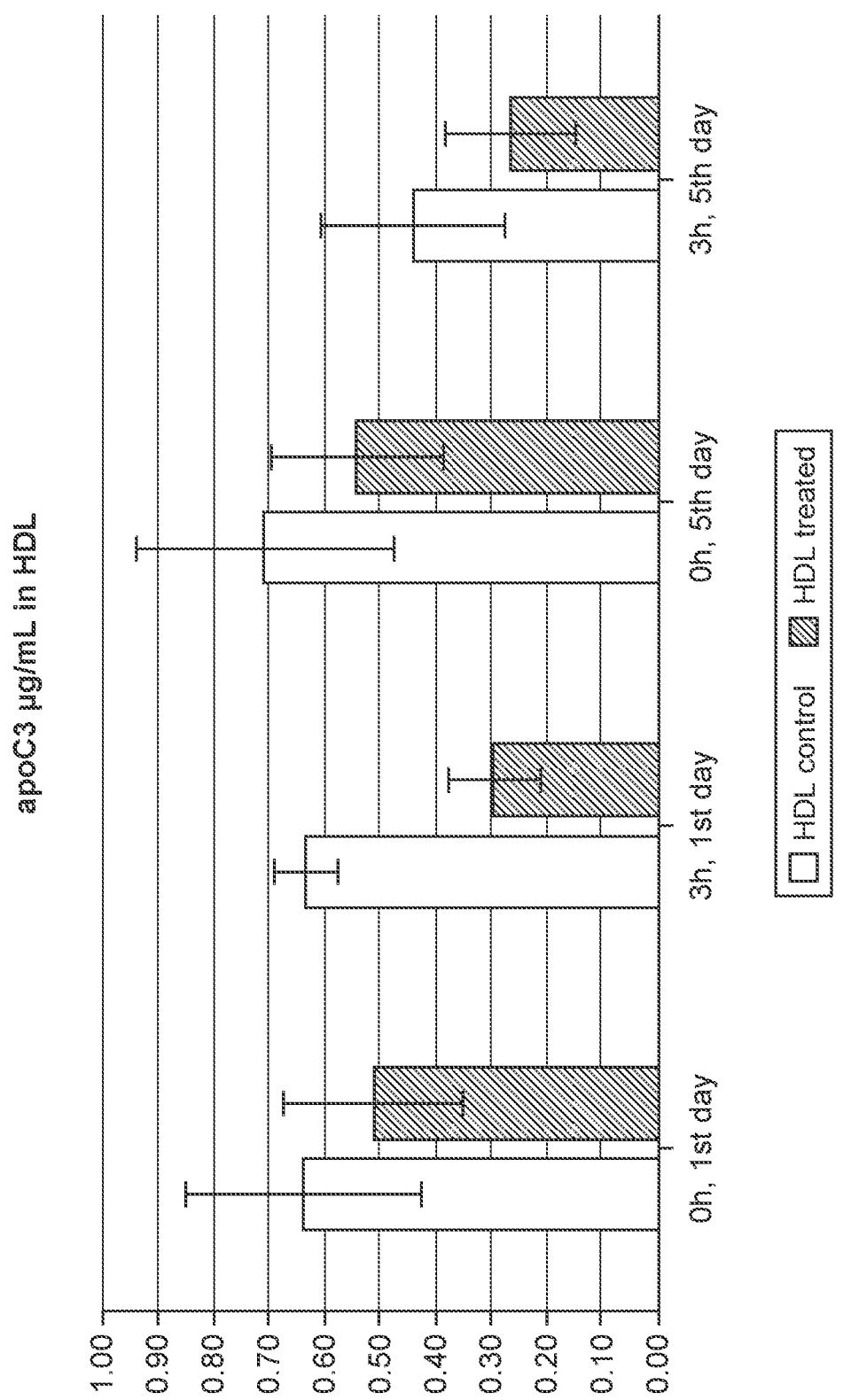

The Delta6PV peptide was injected intraperitoneally into apoC-III transgenic mice at 24 h intervals for 5 days and the plasma lipids were monitored on Day 1 and Day 5 as indicated on FIG. 43A. Repeat injection of Delta6PV resulted in lower plasma TG 1 h, 3 h, and 6 h after the peptide injection on Day 1 and Day 5 as compared to the control conditions (FIG. 43B and FIG. 44). The plasma samples of 0 h and 3 h on Day 1 and Day 5 from mice treated with 5 µmole/kg (B. W.) Delta6PV peptide were applied to SEC-FPLC to separate VLDL and HDL populations. The level of apoC-III on VLDL and HDL were measured by ELISA. The apoC-III decreased on both VLDL and HDL in the Delta6PV-treated mice (FIG. 45A and FIG. 45B). This result indicates that Delta6PV reduced the apoC-III level on VLDL and HDL by displacement.

Figure 46B:
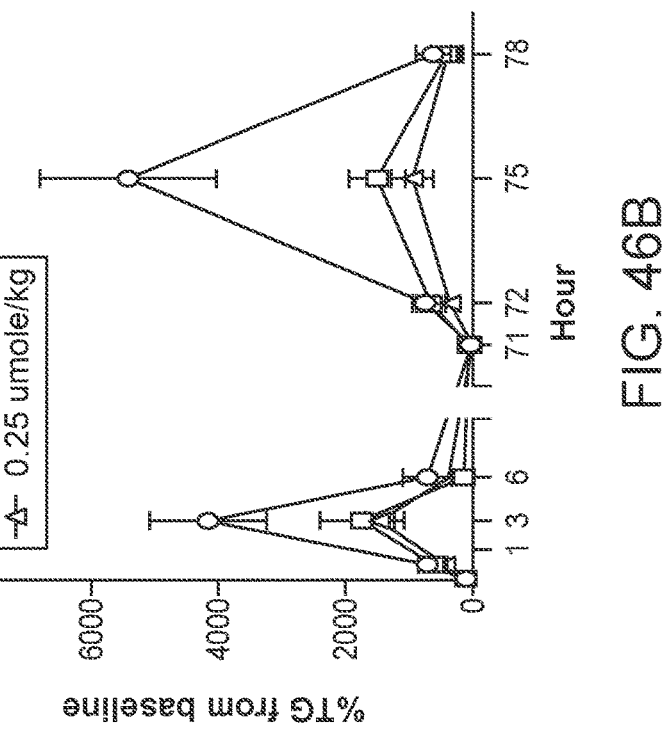
FIG. 46A and FIG. 46B show the percentage change of serum TG level of wild-type mice after Intralipid injection with or without multiple intraperitoneal injections of Delta6PV peptide, with FIG. 46A showing the timeline of injection and FIG. 46B showing the percentage change of serum TG level after intraperitoneal injection of Delta6PV at 0.25 μmole/kg and 1 μmole/kg (B. W.). Saline was used as control.
Figure 46A:
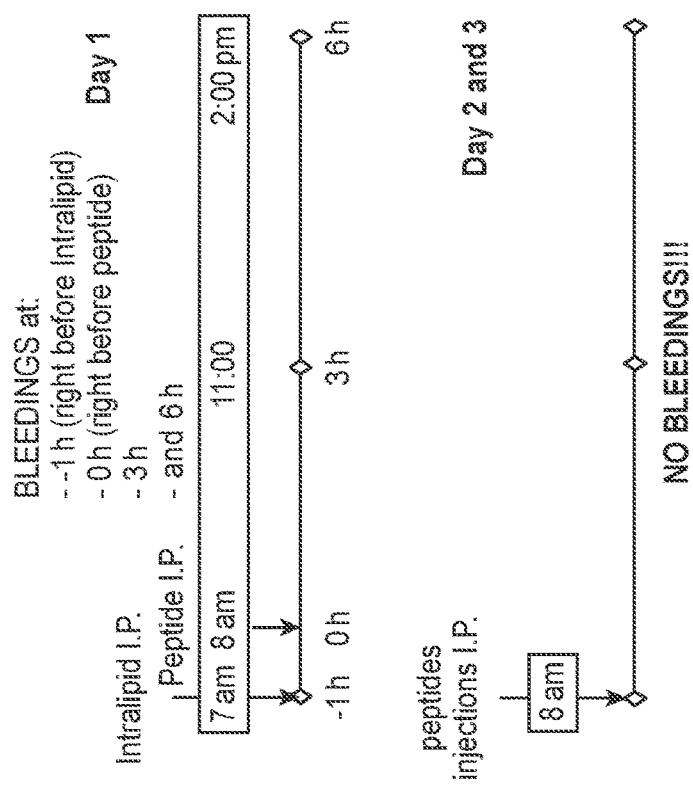

After an intraperitoneal injection with Intralipid, serum TG increased in wild-type mice by more than 40-fold by 3 hours after the injection. When mice were intraperitoneally injected with the Delta6PV peptide 1 hour after the injection of Intralipid, the TG increase was significantly reduced (FIG. 46B).

The repeat-dose studies show that the apoC-II mimetic peptide Delta6PV has the ability to enhance in vivo lipolysis in mouse models.

Example 13: Delta6PV Enhanced In Vivo Lipolysis in the Obese Monkey Model

Figure 47:
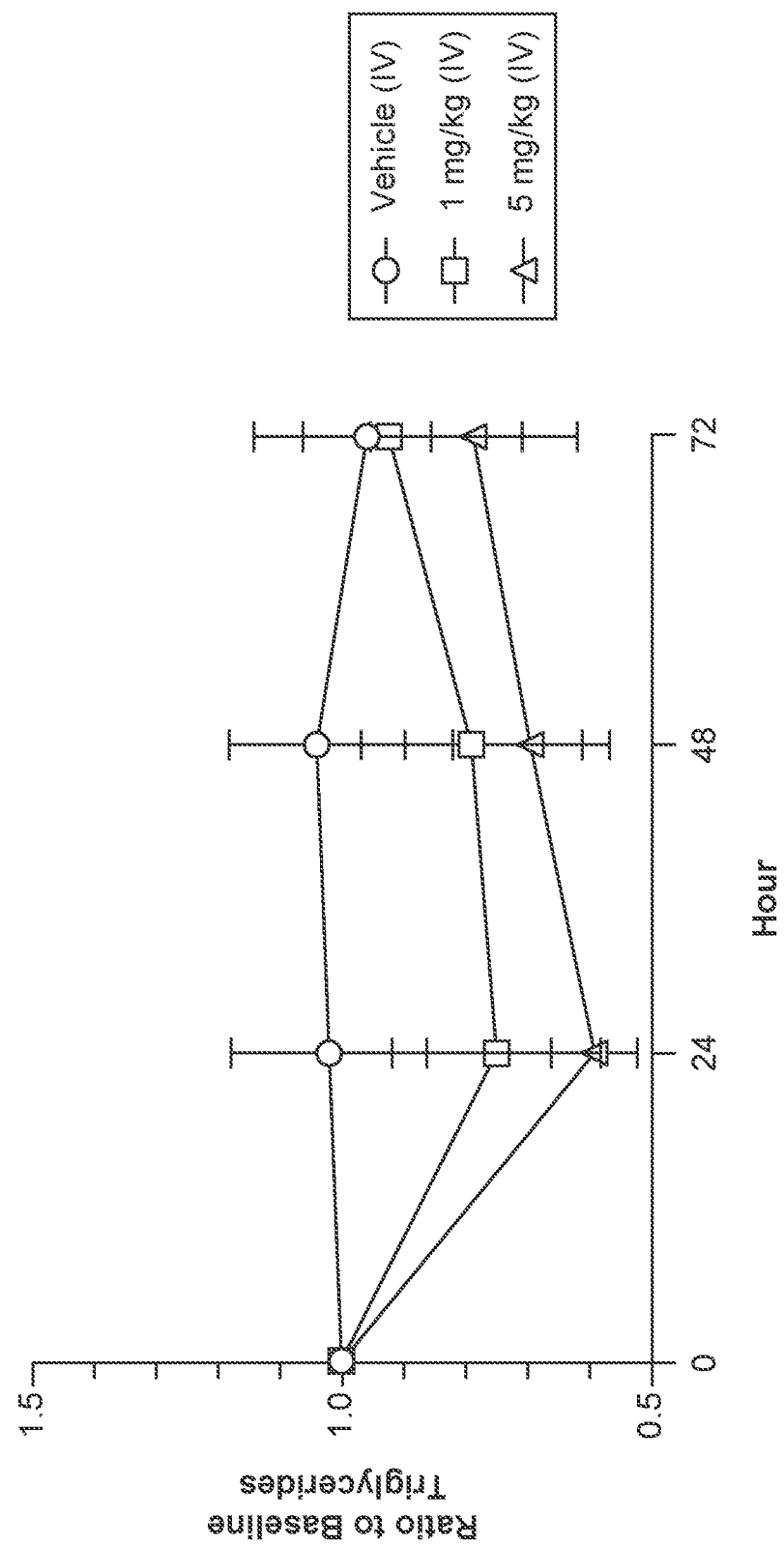
FIG. 47 shows the ratio of serum TG in the obese monkey model with or without intravenous injection of Delta6PV peptide at 1 mg/kg and 5 mg/kg (B. W.) as compared to the baseline level. Saline was used as control.

ApoC-II mimetic peptide Delta6PV was injected intravenously into obese monkeys with a plasma TG level of greater than 2 mmol/L and the plasma lipids were monitored over time. A single injection of Delta6PV peptide led to a significant reduction of plasma TG level measured at 24 h, 48 h, and 72 h after the injection (FIG. 47). The effect of the Delta6PV peptide in the obese monkey model is dose-dependent.

Figure 48A:
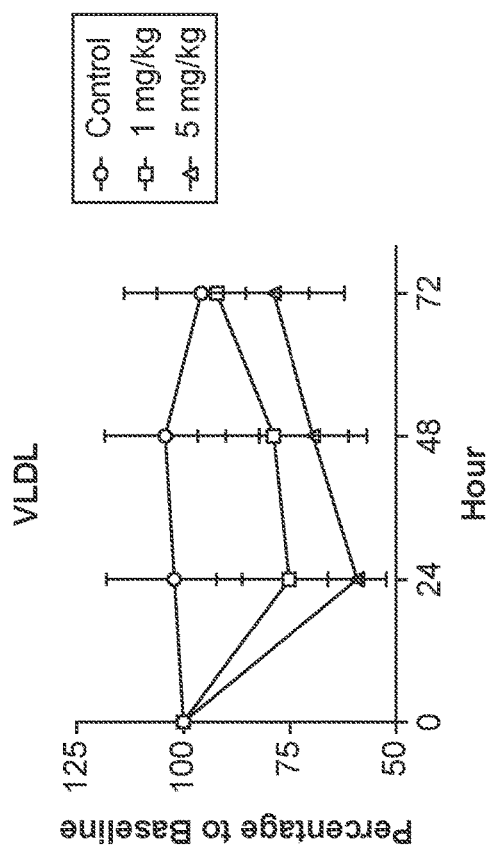
FIG. 48A, FIG. 48B, and FIG. 48C show the percentages of VLDL, LDL, and HDL in the obese monkey model with or without intravenous injection of Delta6PV peptide at 1 mg/kg and 5 mg/kg (B. W.) as compared to the baseline levels, with FIG. 48A showing the percentage of VLDL in the obese monkey model as compared to the baseline level, FIG. 48B showing the percentage of LDL in the obese monkey model as compared to the baseline level, and FIG. 48C showing the percentage of HDL in the obese monkey model as compared to the baseline level.
Figure 48C:
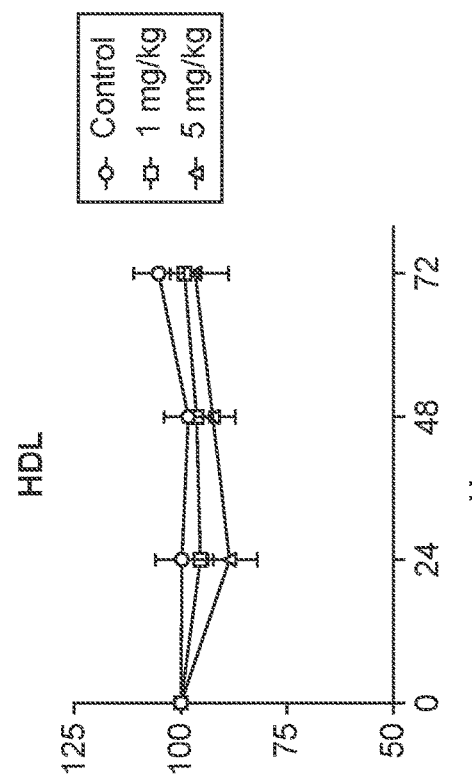
Figure 48B:
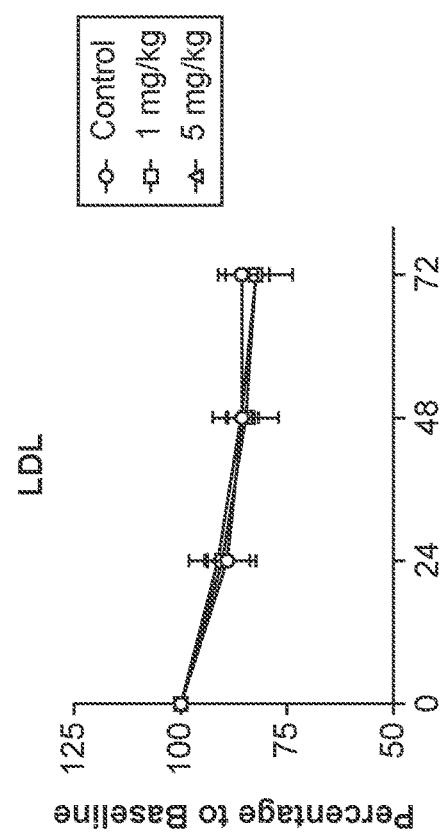

The injection of Delta6PV peptide also led to a marked reduction of the VLDL level (FIG. 48A), although the levels of LDL and HDL did not change significantly (FIG. 48B and FIG. 48C).

In summary, the apoC-II mimetic peptide Delta6PV has the ability to enhance in vivo lipolysis and reduce the VLDL level the obese monkey model.

Example 14: ApoC-III Displacement by Delta6PV Peptide

We investigated the effect of Delta6PV peptide on displacement of apoC-III.

Figure 49:
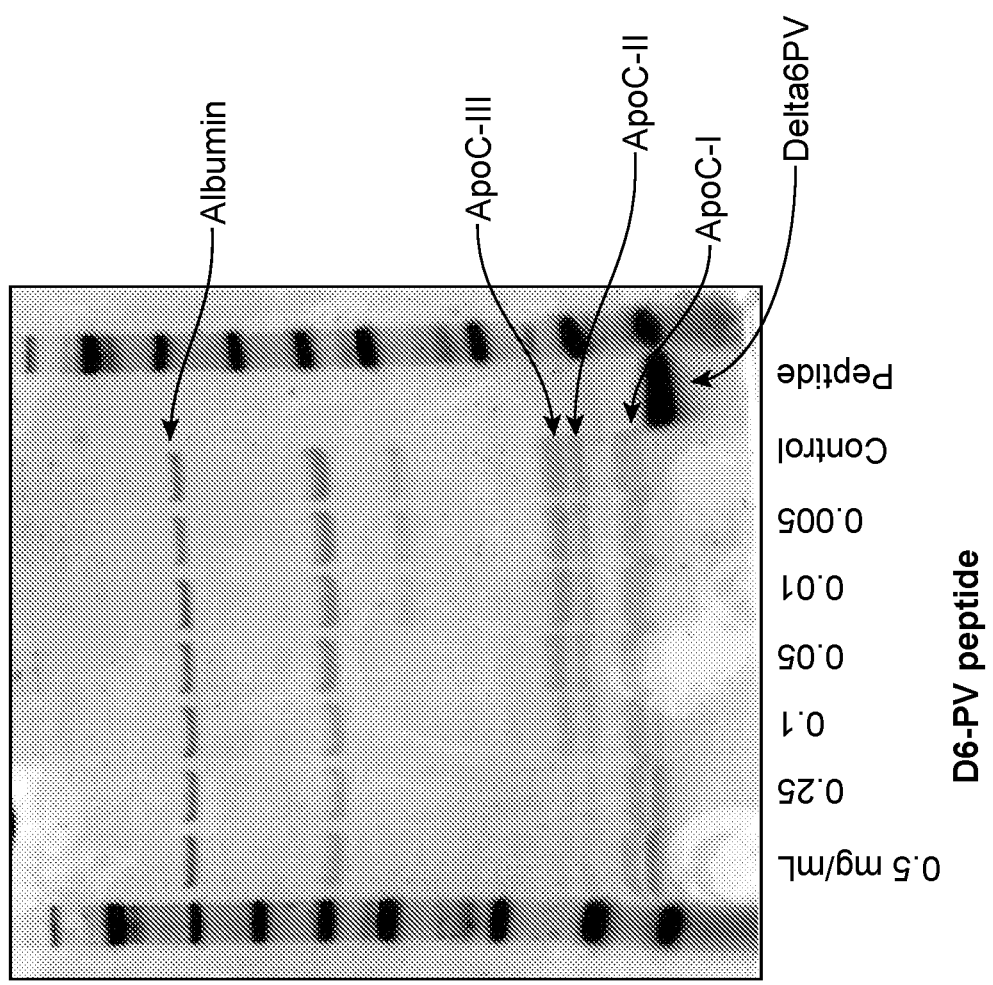
FIG. 49 shows apoC-III displacement by Delta6PV peptide in VLDL isolated from human plasma.

Incubation of VLDL isolated from human plasma with Delta6PV peptide showed that Delta6PV peptide has a higher affinity for the VLDL than the apolipoproteins. As shown in FIG. 49, Delta6PV peptide displaced apoC-III in a dose-dependent matter. The apoC-II in VLDL was also displaced by the Delta6PV peptide.

Figure 50:
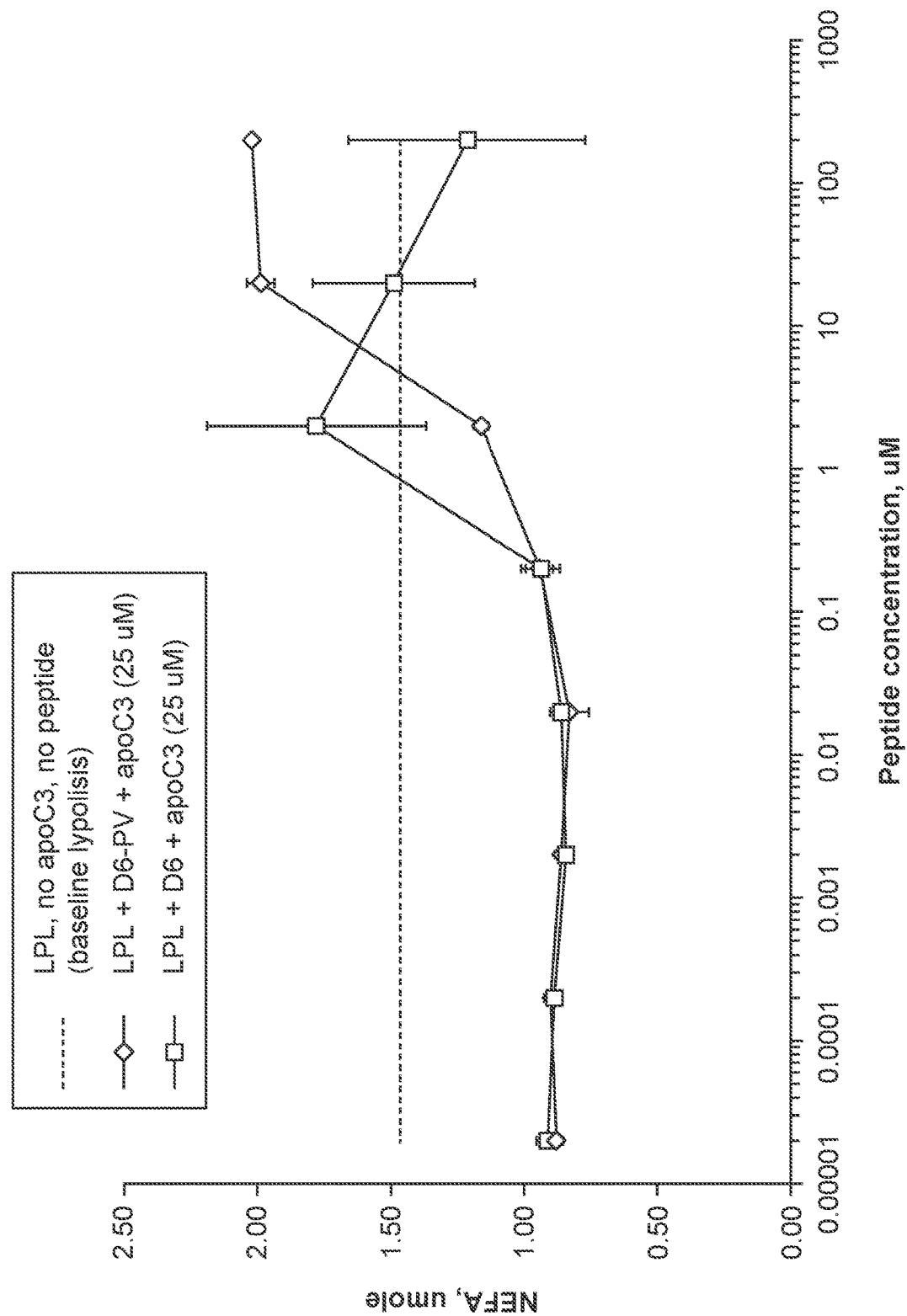
FIG. 50 presents results from an LPL activation assay with high TG human plasma as substrate and recombinant apoC-III as an inhibitor. Delta6PV peptide overcomes the inhibition of apoC-III.

LPL assay was also performed using human apoC-II deficient plasma as a substrate. The results are shown on FIG. 50. When 25 µM apoC-III recombinant protein was added, the free fatty acid (NEFA) production dropped from about 1.5 µM to about 0.8 µM. Delta6 and Delta6PV peptides were added in various concentrations. Addition of Delta6 and Delta6PV peptides overcame the inhibitory effect of apoC-III and facilitated lipolysis.

These results show that the Delta6PV peptide is capable of displacing apoC-III and enhancing in vitro lipolysis.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. An isolated apoC-II mimetic peptide of no more than 50 amino acids, comprising from N-terminus to C-terminus a first helical domain, a hinge region, and a second helical domain, wherein the first helical domain is amphipathic, and wherein the apoC-II mimetic peptide is not a peptide of SEQ ID NO: 56, wherein the hinge region comprises a valine.

2. An isolated apoC-II mimetic peptide comprising, from N-terminus to C-terminus, an amphipathic first helical domain, a hinge region, and a second helical domain, wherein the mimetic peptide has a sequence that differs from the full length of SEQ ID NO: 9 by substitution of 0, 1, 2, 3 or 4 residues.

3. An isolated apoC-II mimetic peptide comprising, from N-terminus to C-terminus, an amphipathic first helical domain, a hinge region, and a second helical domain, wherein the mimetic peptide has a sequence with at least 90% sequence identity to the full length of the sequence set forth in SEQ ID NO: 9.

4. The isolated apoC-II mimetic peptide of claim 3, wherein the mimetic peptide has a sequence with at least 95% sequence identity to the full length of the sequence set forth in SEQ ID NO: 9.

5. The isolated apoC-II mimetic peptide of claim 3, comprising the sequence set forth in SEQ ID NO: 9.

6. A pharmaceutical composition comprising the mimetic peptide of claim 3 and a pharmaceutically acceptable carrier.

7. The pharmaceutical composition of claim 6, wherein the pharmaceutical composition is suitable for subcutaneous injection.

8. A method of treating hypertriglyceridemia in a patient, the method comprising administering to the patient the mimetic peptide of claim 3 or the pharmaceutical composition of claim 6.

9. The method of claim 8, wherein the hypertriglyceridemia is associated with obesity.

10. The method of claim 8, wherein the hypertriglyceridemia is associated with diabetes mellitus.

11. The method of claim 8, wherein the hypertriglyceridemia is associated with alcohol consumption.

12. The method of claim 8, wherein the hypertriglyceridemia is associated with medication.

13. The method of claim 8, wherein the hypertriglyceridemia is caused by LPL deficiency.

14. The method of claim 13, wherein the hypertriglyceridemia is familial LPL deficiency.

15. The method of claim 13, wherein the LPL deficiency is caused by a mutation in the LPL gene.

16. The method of claim 15, wherein the mutation leads to reduced LPL enzyme activity.

17. The method of claim 15, wherein the mutation leads to absent LPL enzyme activity.

18. The method of claim 13, wherein the LPL deficiency is diagnosed by the absence of LPL activity in serum of the patient.

19. The method of claim 15, wherein the mutation is detected by DNA sequence analysis.

20. The method of claim 8, wherein the hypertriglyceridemia is caused by apoC-II deficiency.

21. The method of claim 8, wherein the hypertriglyceridemia is caused by elevated apoC-III.

22. The method of claim 8, wherein the pre-treatment serum triglyceride (TG) concentration of the patient is between 150 mg/dL and 199 mg/dL.

23. The method of claim 8, wherein the pre-treatment serum triglyceride (TG) concentration of the patient is between 200 mg/dL to 499 mg/dL.

24. The method of claim 8, wherein the pre-treatment serum triglyceride (TG) concentration of the patient is between 500 mg/dL to 999 mg/dL.

25. The method of claim 8, wherein the pre-treatment serum triglyceride (TG) concentration of the patient is between 1000 mg/dL and 1999 mg/dL.

26. The method of claim 8, wherein the pre-treatment serum triglyceride (TG) concentration of the patient is equal to or higher than 2000 mg/dL.

27. The method of claim 8, wherein the patient has developed or is at risk for acute pancreatitis.

28. The method of claim 8, wherein the patient has developed or is at risk for acute cardiovascular disease.

29. A method of making the mimetic peptide of claim 3, comprising producing the mimetic peptide recombinantly.

30. A method of making the mimetic peptide of claim 3, comprising producing the mimetic peptide by chemical synthesis.

\* \* \* \* \*